(12) United States Patent
Soma et al.

(10) Patent No.: US 12,358,999 B2
(45) Date of Patent: Jul. 15, 2025

(54) PROTEIN RECOGNIZING DRUG MOIETY OF ANTIBODY-DRUG CONJUGATE

(71) Applicant: DAIICHI SANKYO COMPANY, LIMITED, Tokyo (JP)

(72) Inventors: Masako Soma, Tokyo (JP); Hiroshi Kuga, Tokyo (JP); Takeshi Masuda, Tokyo (JP); Junko Kawamura, Tokyo (JP); Hiromi Ishibashi, Tokyo (JP); Satoru Yasuda, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 1145 days.

(21) Appl. No.: 17/263,322

(22) PCT Filed: Jul. 26, 2019

(86) PCT No.: PCT/JP2019/029379
§ 371 (c)(1),
(2) Date: Jan. 26, 2021

(87) PCT Pub. No.: WO2020/022475
PCT Pub. Date: Jan. 30, 2020

(65) Prior Publication Data
US 2021/0169852 A1 Jun. 10, 2021

(30) Foreign Application Priority Data

Jul. 27, 2018 (JP) .................. 2018-140912

(51) Int. Cl.
| | | |
|---|---|---|
| C07K 16/44 | (2006.01) | |
| A61K 31/407 | (2006.01) | |
| A61K 39/00 | (2006.01) | |
| A61K 47/68 | (2017.01) | |
| A61P 35/00 | (2006.01) | |
| G01N 33/68 | (2006.01) | |
| G01N 33/94 | (2006.01) | |

(52) U.S. Cl.
CPC ............ *C07K 16/44* (2013.01); *A61K 31/407* (2013.01); *A61K 47/68037* (2023.08); *A61P 35/00* (2018.01); *G01N 33/6854* (2013.01); *G01N 33/94* (2013.01); *A61K 2039/505* (2013.01)

(58) Field of Classification Search
CPC .... C07K 16/44; C07K 16/2827; C07K 16/32; C07K 2317/24; C07K 16/46; C07K 17/00; C07K 16/28; C07K 16/30; C07K 2317/565; A61K 31/407; A61K 47/68037; A61K 2039/505; A61K 2039/53; A61K 39/395; A61K 47/68; A61K 31/4738; A61K 47/6801; A61K 47/6889; A61P 35/00; G01N 33/6854; G01N 33/94; G01N 33/5308; G01N 33/53; C12N 5/10; C12N 15/63; C12Q 1/00
See application file for complete search history.

(56) References Cited

U.S. PATENT DOCUMENTS

| | | |
|---|---|---|
| 5,480,968 A | 1/1996 | Kraus et al. |
| 5,677,171 A | 10/1997 | Hudziak et al. |
| 5,821,337 A | 10/1998 | Carter et al. |
| 5,834,476 A | 11/1998 | Terasawa et al. |
| 5,837,673 A | 11/1998 | Tsujihara et al. |
| 5,892,043 A | 4/1999 | Tsujihara et al. |
| 5,968,511 A | 10/1999 | Akita et al. |
| 6,071,719 A | 6/2000 | Halsey et al. |
| 6,096,868 A | 8/2000 | Halsey et al. |
| 6,214,345 B1 | 4/2001 | Firestone et al. |
| 6,291,671 B1 | 9/2001 | Inoue et al. |
| 6,835,807 B1 | 12/2004 | Susaki et al. |
| 7,041,818 B2 | 5/2006 | Susaki et al. |

(Continued)

FOREIGN PATENT DOCUMENTS

| | | |
|---|---|---|
| CA | 2927832 A1 | 11/2011 |
| CA | 2815154 A1 | 2/2012 |

(Continued)

OTHER PUBLICATIONS

Sharma, et al., Clin. Canc. Research 2001 7:3963 (Year: 2001).*

(Continued)

*Primary Examiner* — Julie Wu
*Assistant Examiner* — Sydney Van Druff
(74) *Attorney, Agent, or Firm* — Foley & Lardner LLP

(57) ABSTRACT

A protein that recognizes a drug moiety of an antibody-drug conjugate in which a drug represented by the following formula is conjugated to an antibody via a linker, and a method for quantifying the concentration in plasma of an antibody-drug conjugate in a mammal to which the antibody-drug conjugate has been administered, by using the protein, and a method for identifying a tissue distribution of an antibody-drug conjugate.

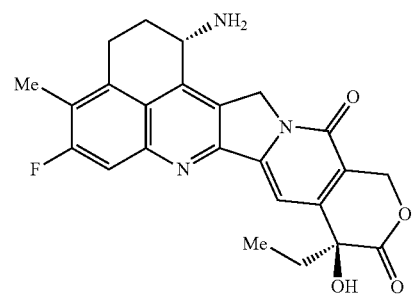

23 Claims, 33 Drawing Sheets
Specification includes a Sequence Listing.

(56) References Cited

U.S. PATENT DOCUMENTS

| | | |
|---|---|---|
| 7,449,184 B2 | 11/2008 | Allison et al. |
| 7,585,491 B2 | 9/2009 | Govindan |
| 7,833,979 B2 | 11/2010 | Sullivan et al. |
| 7,837,980 B2 | 11/2010 | Alley et al. |
| 7,999,083 B2 | 8/2011 | Govindan et al. |
| 8,226,945 B2 | 7/2012 | Ebens et al. |
| 8,268,319 B2 | 9/2012 | Govindan |
| 8,394,607 B2 | 3/2013 | Ebens et al. |
| 8,425,912 B2 | 4/2013 | Govindan |
| 8,524,865 B2 | 9/2013 | Ebens et al. |
| 8,741,291 B2 | 6/2014 | Bhat et al. |
| 8,802,820 B2 | 8/2014 | Chamberlain et al. |
| 8,907,071 B2 | 12/2014 | Sullivan et al. |
| 8,968,741 B2 | 3/2015 | Ebens et al. |
| 9,808,537 B2 | 11/2017 | Masuda et al. |
| 9,850,312 B2 | 12/2017 | Agatsuma et al. |
| 9,872,924 B2 | 1/2018 | Naito et al. |
| 10,195,288 B2 | 2/2019 | Masuda et al. |
| 10,227,417 B2 | 3/2019 | Agatsuma et al. |
| 10,383,878 B2 | 8/2019 | Hettmann et al. |
| 2003/0018989 A1 | 1/2003 | Brennan et al. |
| 2003/0148931 A1 | 8/2003 | Takahashi et al. |
| 2003/0166513 A1 | 9/2003 | Imura et al. |
| 2004/0185053 A1 | 9/2004 | Govindan |
| 2005/0123536 A1 | 6/2005 | Law et al. |
| 2005/0228007 A1 | 10/2005 | Jagtap et al. |
| 2005/0271671 A1 | 12/2005 | Griffiths |
| 2005/0276812 A1 | 12/2005 | Ebens, Jr. et al. |
| 2006/0018899 A1 | 1/2006 | Kao et al. |
| 2006/0134109 A1 | 6/2006 | Gaitanaris et al. |
| 2006/0193865 A1 | 8/2006 | Govindan |
| 2007/0071764 A1 | 3/2007 | Sullivan et al. |
| 2008/0050310 A1 | 2/2008 | Ebens et al. |
| 2008/0131363 A1 | 6/2008 | Govindan et al. |
| 2008/0161245 A1 | 7/2008 | Kratz et al. |
| 2008/0260744 A1 | 10/2008 | Gaitanaris et al. |
| 2008/0305044 A1 | 12/2008 | McDonagh et al. |
| 2009/0178153 A1 | 7/2009 | Gaitanaris et al. |
| 2009/0274713 A1 | 11/2009 | Chari et al. |
| 2009/0286258 A1 | 11/2009 | Kaur et al. |
| 2009/0291093 A1 | 11/2009 | Govindan |
| 2010/0068181 A1 | 3/2010 | Paliwal et al. |
| 2010/0120816 A1 | 5/2010 | Fontana et al. |
| 2010/0303802 A1 | 12/2010 | Zoffmann Jensen et al. |
| 2011/0045587 A1 | 2/2011 | Sullivan et al. |
| 2011/0059076 A1 | 3/2011 | Mcdonagh et al. |
| 2011/0070248 A1 | 3/2011 | Ichikawa et al. |
| 2011/0185439 A1 | 7/2011 | Gaitanaris et al. |
| 2011/0229406 A1 | 9/2011 | Hettmann et al. |
| 2011/0293513 A1 | 12/2011 | Govindan et al. |
| 2012/0121615 A1 | 5/2012 | Flygare et al. |
| 2012/0171201 A1 | 7/2012 | Sapra |
| 2012/0201809 A1 | 8/2012 | Bhat et al. |
| 2012/0328634 A1 | 12/2012 | Govindan |
| 2013/0089872 A1 | 4/2013 | Nakamura et al. |
| 2013/0123178 A1 | 5/2013 | Dimarchi et al. |
| 2013/0216561 A1 | 8/2013 | Govindan |
| 2013/0247233 A1 | 9/2013 | Gaitanaris et al. |
| 2014/0004078 A1 | 1/2014 | Govindan |
| 2015/0297748 A1 | 10/2015 | Masuda et al. |
| 2015/0352224 A1 | 12/2015 | Naito et al. |
| 2016/0219845 A1 | 8/2016 | Gaitanaris et al. |
| 2016/0279259 A1 | 9/2016 | Masuda et al. |
| 2016/0282365 A1 | 9/2016 | Gaitanaris et al. |
| 2016/0287722 A1 | 10/2016 | Govindan |
| 2016/0297890 A1 | 10/2016 | Agatsuma et al. |
| 2017/0021031 A1 | 1/2017 | Hettmann et al. |
| 2017/0188555 A1 | 7/2017 | Gaitanaris et al. |
| 2018/0036423 A1 | 2/2018 | Hu |
| 2018/0147292 A1 | 5/2018 | Noguchi et al. |
| 2019/0151328 A1 | 5/2019 | Hettmann et al. |

FOREIGN PATENT DOCUMENTS

| | | |
|---|---|---|
| CA | 2859255 A1 | 6/2013 |
| CA | 2895869 A1 | 6/2014 |
| CN | 1227499 A | 9/1999 |
| CN | 1764478 A | 4/2006 |
| CN | 101023100 A | 8/2007 |
| CN | 101490087 A | 7/2009 |
| CN | 102481364 A | 5/2012 |
| CN | 104744560 A | 7/2015 |
| CN | 105829346 A | 8/2016 |
| CN | 107922477 A | 4/2018 |
| EP | 0 495 432 A1 | 7/1992 |
| EP | 0 737 686 A1 | 10/1996 |
| EP | 0 916 348 A1 | 5/1999 |
| EP | 1 155 702 A1 | 11/2001 |
| EP | 2 594 589 A1 | 5/2013 |
| EP | 2 799 452 A1 | 11/2014 |
| EP | 2 907 824 A1 | 8/2015 |
| EP | 2 910 573 A1 | 8/2015 |
| EP | 3 101 032 A1 | 12/2016 |
| EP | 3 315 512 A1 | 5/2018 |
| JP | H05-059061 A | 3/1993 |
| JP | H06-087746 A | 3/1994 |
| JP | H08-337584 A | 12/1996 |
| JP | H10-095802 A | 4/1998 |
| JP | H11-071280 A | 3/1999 |
| JP | H11-092405 A | 4/1999 |
| JP | 2002-060351 A | 2/2002 |
| JP | 2005-511627 A | 4/2005 |
| JP | 2006-511526 A | 4/2006 |
| JP | 2007-527872 A | 10/2007 |
| JP | 2008-521828 A | 6/2008 |
| JP | 2009-538629 A | 11/2009 |
| JP | 2010-513524 A | 4/2010 |
| JP | 2011-519864 A | 7/2011 |
| JP | 2011-524001 A | 8/2011 |
| JP | 2012-509259 A | 4/2012 |
| JP | 2012-100671 A | 5/2012 |
| JP | 2013-500253 A | 1/2013 |
| JP | 2013-534535 A | 9/2013 |
| JP | 2013-534906 A | 9/2013 |
| JP | 2017-503784 A | 2/2017 |
| KR | 10-2001-0052385 A | 6/2001 |
| KR | 10-2011-0044808 A | 4/2011 |
| RU | 2404810 C2 | 7/2008 |
| RU | 2450008 C2 | 7/2010 |
| TW | I232930 B | 5/2005 |
| TW | 200817434 A | 4/2008 |
| WO | WO-97/46260 A1 | 12/1997 |
| WO | WO-99/46296 A1 | 9/1999 |
| WO | WO-00/25825 A1 | 5/2000 |
| WO | WO-01/00244 A2 | 1/2001 |
| WO | WO-02/00734 A1 | 1/2002 |
| WO | WO-03/013602 A1 | 2/2003 |
| WO | WO-03/015826 A1 | 2/2003 |
| WO | WO-03/043583 A2 | 5/2003 |
| WO | WO-03/074566 A2 | 9/2003 |
| WO | WO-2004/040000 A2 | 5/2004 |
| WO | WO-2005/040825 A2 | 5/2005 |
| WO | WO-2005/112919 A2 | 12/2005 |
| WO | WO-2006/065533 A2 | 6/2006 |
| WO | WO-2006/092230 A2 | 9/2006 |
| WO | WO-2007/077028 A2 | 7/2007 |
| WO | WO-2008/100624 A2 | 8/2008 |
| WO | WO-2008/116219 A2 | 9/2008 |
| WO | WO-2008/144891 A1 | 12/2008 |
| WO | WO-2011/011474 A1 | 1/2011 |
| WO | WO-2011/021397 A1 | 2/2011 |
| WO | WO-2011/050071 A2 | 4/2011 |
| WO | WO-2011/068845 A1 | 6/2011 |
| WO | WO-2011/145744 A1 | 11/2011 |
| WO | WO-2011/155579 A1 | 12/2011 |
| WO | WO-2012/019024 A2 | 2/2012 |
| WO | WO-2012/064733 A2 | 5/2012 |
| WO | WO-2013/068946 A2 | 5/2013 |
| WO | WO-2013/077458 A1 | 5/2013 |
| WO | WO-2013/163229 A1 | 10/2013 |
| WO | WO-2013/188740 A1 | 12/2013 |

(56) References Cited

FOREIGN PATENT DOCUMENTS

| WO | WO-2014/057687 A1 | 4/2014 |
|----|-------------------|--------|
| WO | WO-2014/061277 A1 | 4/2014 |
| WO | WO-2014/107024 A1 | 7/2014 |
| WO | WO-2015/098099 A1 | 7/2015 |
| WO | WO-2015/115091 A1 | 8/2015 |
| WO | WO-2015/142675 A2 | 9/2015 |
| WO | WO-2015/146132 A1 | 10/2015 |
| WO | WO-2015/155976 A1 | 10/2015 |
| WO | WO-2015/155998 A1 | 10/2015 |
| WO | WO-2016/024195 A1 | 2/2016 |
| WO | WO-2017/002776 A1 | 1/2017 |
| WO | WO-2018/066626 A1 | 4/2018 |
| WO | WO-2018/185618 A1 | 10/2018 |
| WO | WO-2018/212136 A1 | 11/2018 |

OTHER PUBLICATIONS

Sela-Culang, et al., Front. In Immunol. 2013; vol. 4 Article 302 (Year: 2013).*
Ahmad, et al., Adv Med, Den and Health Sci, 2021 4(4):37 (Year: 2021).*
Nitiss, et al., Curr Protoc Pharmacol. Jun. 2012; Chapter: Unit 3.3 (Year: 2012).*
"Appeal for Reposition against Resolution 12260 of Feb. 21 of 2018, by which a patent of invention is granted," filed in Colombian Patent Office in connection with Colombian Patent Application No. NC2016/0000187.
Abstract of Davoli, et al., "Progression and treatment of HER2-positive breast cancer", Cancer Chemother Pharmacol. 65(4): 611-23 (2010).
Acchione et al., "Impact of linker and conjugation chemistry on antigen binding, Fc receptor binding and thermal stability of model antibody-drug conjugates," mAbs, vol. 4, No. 3, May/Jun. 2012, pp. 362-372.
Adams et al., "Humanization of a recombinant monoclonal antibody to produce a therapeutic HER dimerization inhibitor, pertuzumab," Cancer Immunol. Immunother. 55:717-727 (2006).
Alimandi et al., "Cooperative signaling of ErbB3 and ErbB2 in neoplastic transformation and human mammary carcinomas," Oncogene 10:1813-1821 (1995)—9 Pages.
Allander et al., "Gastrointestinal Stromal Tumors with KIT Mutations Exhibit a Remarkably Homogeneous Gene Expression Profile," Cancer Research, vol. 61, pp. 8624-8628, Dec. 15, 2001.
Allowance issued in connection with Taiwanese Patent Application No. 104103127, dated Apr. 11, 2018.
Australian Intellectual Property Office, "Examination Report No. 2 for Standard Patent Application," Australian Patent Application No. 2014371934, dated Sep. 13, 2019.
Barginear et al., "Trastuzumab-DM1: A Review of the Novel Immuno-Conjugate for HER2-Overexpressing Breast Cancer," The Open Breast Cancer Journal, vol. 1, 2009, pp. 25-30.
Barok et al., "Trastuzumab-DM1 is highly effective in preclinical models of HER2-positive gastric cancer," Cancer Letters, vol. 306, 2011, pp. 172-179.
Baselga et al., "Phase II Study of Weekly Intravenous Recombinant Humanized Anti-p185HER2 Monoclonal Antibody in Patients with HER2/neu-Overexpressing Metastatic Breast Cancer," J. Clin. Oncol. 14(3):737-744 (Mar. 1996).
Basu et al., "The Epithelial/Carcinoma Antigen EGP-1 Recognized by Monoclonal Antibody RS7-3G11, is Phosphorylated on Serine 303," Int. J. Cancer 62(4):472-479 (1995).
Bauer et al., "Emerging Agents for the Treatment of Advanced, Imatinib-Resistant Gastrointestinal Stromal Tumors: Current Status and Future Directions," Drugs, vol. 75, 2015, pp. 1323-1334.
Beck, Alain, "The Next Generation of Antibody-drug Conjugates Comes of Age," Discovery Medicine, vol. 10, No. 53, Oct. 16, 2010 (8 pages).
Behrens et al., "Methods for site-specific drug conjugation to antibodies," mAbs, vol. 6, No. 1, 2014, pp. 46-53.

Blok et al., "Cytoplasmic Overexpression of HER2: a Key Factor in Colorectal Cancer," Clinical Medicine Insights: Oncology, vol. 7, 2013, pp. 41-51.
Bouchard et al., "Antibody-drug conjugates—A new wave of cancer drugs," Bioorganic & Medicinal Chemistry Letters, vol. 24, 2014, pp. 5357-5363.
Burke et al., "Design, Synthesis, and Biological Evaluation of Antibody-Drug Conjugates Comprised of Potent Camptothecin Analogues", Bioconjugate Chemistry, vol. 20, No. 6, 2009, pp. 1242-1250.
Calabrese et al., "Assignment of TACSTD1 (alias TROP1, M4S1) to human chromosome 2p21 and refinement of mapping of TACSTD2 (alias TROP2, M1S1) to human chromosome 1p32 by in situ hybridization," Cytogenet Cell Genet. 92(1-2):164-165 (2001).
Callahan and Hurvitz, "HER2-Positive Breast Cancer: Current Management of Early, Advanced, and Recurrent Disease", Curr Opin Obstet Gynecol. 23(1): 37-43 (2011).
Canadian Intellectual Property Office, "Interview Summary," issued in connection with Canadian Patent Application No. 2,885,800, dated Mar. 28, 2017.
Canadian Intellectual Property Office, "Office Action," issued in connection with Canadian Patent Application No. 2,939,802, dated Apr. 13, 2018.
Cardillo, T., "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research 17(10): 3157-3169 (2011).
Carl U. Bialucha et al: "Discovery and Optimization of HKT288, a Cadherin-6-Targeting ADC for the Treatment of Ovarian and Renal Cancers", Cancer Discovery, vol. 7, No. 9, Sep. 1, 2017 (Sep. 1, 2017), pp. 1030-1045, XP055484340.
Chi et al., "ETV1 is a lineage survival factor that cooperates with KIT in gastrointestinal stromal tumours," Nature, vol. 467, Oct. 14, 2010, pp. 849-855.
Chinese Office Action dated Nov. 1, 2016 in corresponding application No. 201380053256.2.
Chinese Office Action dated Nov. 8, 2019 for corresponding Application No. 201580019138.9—4 pages.
Chinese Search Report dated Jun. 24, 2020 for corresponding Application No. 108114649.
Cho et al., "Differential expression and function of cadherin-6 during renal epithelium development," Development, vol. 125, 1998, pp. 803-812.
Colombian Reconsideration Petition dated Mar. 15, 2018 in corresponding application No. NC2016/0000187.
Corada M et al: "Monoclonal antibodies directed to different regions of vascular endothelial cadherin extracellular domain affect adhesion and clustering of the protein and modulate endothelial permeability", Blood, The American Society of Hematology, US, vol. 97, No. 6, Mar. 15, 2001 (Mar. 15, 2001), pp. 1679-1684, XP002187985.
Corless et al., "Gastrointestinal stromal tumours: origin and molecular oncology," Nature Reviews, Cancer, vol. 11, Dec. 2011, pp. 865-878.
Coussens et al., "Tyrosine Kinase Receptor with Extensive Homology to EGF Receptor Shares Chromosomal Location with neu Oncogene," Science 230(4730):1132-1139 (Dec. 1985).
De Jager et al., "DX-8951f: Summary of Phase I Clinical Trials," Ann. N.Y. Acad. Sci., vol. 922, 2000, pp. 260-273.
Defazio et al., "Expression of c-erbB Receptors, Heregulin and Oestrogen Receptor in Human Breast Cell Lines," Int. J. Cancer 87:487-498 (2000)—12 Pages.
Demetri et al., "NCCN Task Force Report: Update on the Management of Patients with Gastrointestinal Stromal Tumors," Journal of the National Comprehensive Cancer Network, vol. 8, Supplement 2, Apr. 2010, pp. S-1-S-41.
Di Fiore et al., "erbB-2 Is a Potent Oncogene When Overexpressed in NIH/3T3 Cells," Science 237:178-182 (Jul. 1987).
Donaghy, Heather, "Effects of antibody, drug and linker on the preclinical and clinical toxicities of antibody-drug conjugates," mAbs, vol. 8, No. 4, 2016, pp. 659-671.
Dosio et al., "Antibody-targeted leucinostatin A", Journal of Controlled Release, No. 32, (1994), pp. 37-44.

(56) References Cited

OTHER PUBLICATIONS

El Sewedy et al., "Cloning of the Murine Trop2 Gene: Conservation of a PIP2-Binding Sequence in the Cytoplasmic Domain of Trop-2," Int. J. Cancer 75(2):324-330 (1998).
English-language translation of International Search Report issued in International Patent Application No. PCT/JP2015/002020 mailed Jul. 20, 2015.
Esteva et al., "A Phase II Study of Intravenous Exatecan Mesylate (DX-8951f) Administered Daily for 5 Days Every 3 Weeks to Patients with Metastatic Breast Carcinoma", American Cancer Society,2003,900-907.
European Patent Office, "Extended European Search Report," issued in connection with European Patent Application No. 19206764.3., dated Feb. 4, 2020.
European Patent Office, "Communication with extended European Search Report," issued in connection with European Patent Application No. 13845596.9, dated May 6, 2016.
European Patent Office, "Communication with extended European Search Report," issued in connection with European Patent Application No. 13847461.4, dated May 13, 2016.
European Search Report issued in corresponding application No. 14874745.4 dated May 10, 2017.
Extended European Search Report dated Jan. 19, 2021 for corresponding European Patent Application No. 18802536.5.
Extended European Search Report dated Nov. 30, 2020 for corresponding European Patent Application No. 18742022.9.
Extended European Search Report issued in European Patent Application No. 15743738.5 dated Aug. 9, 2017.
Extended European Search Report issued in European Patent Application No. 15776810.2 dated Aug. 11, 2017.
Faulk et al., "Antigens of human trophoblasts: A working hypothesis for their role in normal and abnormal pregnancies," Proc. Natl. Acad. Sci. USA 75(4):1947-1951 (1978).
Fendly et al., "Characterization of Murine Monoclonal Antibodies Reactive to Either the Human Epidermal Growth Factor Receptor or HER2/neu Gene Product," Cancer Research 50:1550-1558 (1990).
Final Office Action issued in U.S. Appl. No. 15/221,851 mailed Nov. 13, 2017.
Fong et al., "High expression of TROP2 correlates with poor prognosis in pancreatic cancer," Br. J. Cancer 99(8):1290-1295 (2008).
Fong et al., "TROP2: a novel prognostic marker in squamous cell carcinoma of the oral cavity," Mod. Pathol. 21(2):186-191 (2008).
Fornaro et al., "Cloning of the Gene Encoding Trop-2, a Cell-Surface Glycoprotein Expressed by Human Carcinomas," Int. J. Cancer 62(5):610-618 (1995).
Fukushige et al., "Localization of a Novel v-erbB-Related Gene, c-erbB-2, on Human Chromosome 17 and Its Amplification in a Gastric Cancer Cell Line," Mol. Cell. Biol. 6(3):955-958 (1986).
Giridhar, "HER2-positive breast cancer: What is it?", Mayo Clinic, Mayo Foundation for Medical Education and Research (2020).
Goeppert et al., "Cadherin-6 is a putative tumor suppressor and target of epigenetically dysregulated miR-429 in cholangiocarcinoma," Epigenetics, vol. 11, No. 11, 2016, pp. 780-790.
Gomez-Monterrey et al., "Design, Synthesis, and Cytotoxic Evaluation of Acyl Derivatives of 3-Aminonaphtho[2,3-b]thiophene-4,9-dione, a Quinone-Based System," Journal of Medicinal Chemistry, 2011, 54(12):4077-4091, abstract.
Graus-Porta et al., "ERbB-2, the preferred heterodimerization partner of all ErbB receptors, is a mediator of lateral signaling," EMBO J. 16(7):1647-1655 (1997).
Gravalos et al., "HER2 in gastric cancer: a new prognostic factor and a novel therapeutic target," Ann. Oncol. 19:1523-1529 (2008).
Gugnoni et al., "Cadherin-6 promotes EMT and cancer metastasis by restraining autophagy," Oncogene, vol. 36, 2017, pp. 667-677.
Haasen Dorothea et al: "G protein-coupled receptor internalization assays in the high-content screening format", Biomembranes: Transport Theory: Cells and Model Membranes; [Methods in Enzymology, ISSN 0076-6879], Elsevier, Academic Press, NL, vol. 414, Jan. 1, 2006 (Jan. 1, 2006), pp. 121-139.

Hardwick et al., "Immunohistochemical detection of p53 and c-erbB-2 in oesophageal carcinoma; no correlation with prognosis," Eur. J. Surg. Oncol. 23:30-35 (1997).
Hase et al., "Characterization of an Orphan G Protein-coupled Receptor, GPR20, That Constitutively Activates Gi Proteins*," the Journal of Biological Chemistry, vol. 283, No. 19, May 9, 2008, pp. 12747-12755.
Hinrichs et al., "Antibody Drug Conjugates: Nonclinical Safety Considerations," the AAPS Journal, vol. 17, No. 5, Sep. 2015, pp. 1055-1064.
Hirata T: "Producing monoclonal antibody of extracellular domain of metabotropic glutamate receptor 1, by hybridizing spleen cell of non-human animal immunized by olfactory tract, with myeloma cell, culturing hybridoma, screening culture supernatant", WPI/Thomson,, vol. 2004, No. 36, Apr. 22, 2004 (Apr. 22, 2004).
Howard A., et al., " Phase II Study of the Antibody Drug Conjugate Trastuzumab-DM1 for the Treatment of Human Epidermal Growth Factor Receptor 2 (HER2)-Positive Breast Cancer After Prior HER2-Directed Therapy ", Journal of Clinical Oncology, vol. 29, pp. 398-405, 2011 (8 pages).
Hudis, M.D., Clifford A., "Trastuzumab—Mechanism of Action and Use in Clinical Practice," N. Engl. J. Med. 357(1):39-51 (2007).
Hudziak et al., "Increased expression of the putative growth factor receptor p185HER2 causes transformation and tumorigenesis of NIH 3T3 cells," Proc. Natl. Acad. Sci. USA 84:7159-7163 (1987).
I. Sullivan, et al. "Osimertinib in the treatment of patients with epidermal growth factor receptor T790M mutation-positive metastatic non-small cell lung cancer: clinical trial evidence and experience", Therapeutic Advances in Respiratory Disease, vol. 10(6), pp. 549-565, 2016 (17 pages).
IN Office Action issued in the corresponding Indian Patent Application Ser. No. 201647013640, dated Jul. 19, 2019.
Inoue et al., "Cadherin-6 Expression Transiently Delineates Specific Rhombomeres, Other Neural Tube Subdivisions, and Neural Crest Subpopulations in Mouse Embryos," Developmental Biology, vol. 183, 1997, pp. 183-194.
Inoue et al., "CM-Dextran-Polyalcohol-Camptothecin Conjugate: DE-310 with A Novel Carrier System and Its Preclinical Data," Polymer Drugs in the Clinical Stage, 2003, pp. 145-153.
Intellectual Property Office of Singapore, "Invitation to Respond to Written Opinion," issued in connection with Singaporean Patent Application No. 11201502887W, dated Apr. 22, 2016.
International Search Report and Written Opinion for correspondence Application No. PCT/JP2018/007152 dated Apr. 24, 2018.
International Search Report for corresponding Application No. PCT/JP2014/006421 mailed Mar. 17, 2015.
International Search Report issued in International Patent Application No. PCT/JP2015/000355 mailed Apr. 21, 2015.
International Searching Authority, "International Search Report," issued in connection with International Patent Application No. PCT/JP2013/006069, dated Dec. 17, 2013.
International Searching Authority, "International Search Report," issued in connection with International Patent Application No. PCT/JP2013/006178, dated Dec. 17, 2013.
International Searching Authority, "International Search Report," issued in connection with International Patent Application No. PCT/JP2018/001065, dated Apr. 17, 2018.
International Searching Authority, "International Search Report," issued in connection with International Patent Application No. PCT/JP2018/018572, dated Aug. 7, 2018.
International Searching Authority, "Written Opinion," issued in connection with International Patent Application No. PCT/JP2018/001065, dated Apr. 17, 2018.
International Searching Authority, "Written Opinion," issued in connection with International Patent Application No. PCT/JP2018/018572, dated Aug. 7, 2018.
Janne, P., et al., "Phase 1 study of the Anti-HER3 Antibody Drug Conjugate U3-1402 in Metastic or Unresectable EGFR-mutant NSCLC.", Journal of Thoracic Oncology, vol. 12, No. 11, Supp. Supplement 2, pp. S2290, abstract No. P3.04-013, Nov. 2017 (3 pages).
Japanese Notice Of Allowance dated Oct. 18, 2016 in corresponding application No. 2016-166850.

(56) References Cited

OTHER PUBLICATIONS

Japanese Patent Office, "Decision to Grant a Patent," in connection with Japanese Patent Application No. 2016-166850, dated Oct. 18, 2016.
Japanese Patent Office, "Decision to Grant Patent," issued in connection with Japanese Patent Application No. 2016-117096, dated Jul. 4, 2017.
Japanese Patent Office, "Notification of Reasons for Refusal," in connection with Japanese Patent Application No. 2016-540705, dated Dec. 6, 2016.
Joto et al., "DX-8951F, A Water-Soluble Camptothecin Analog, Exhibits Potent Antitumor Activity Against a Human Lung Cancer Cell Line and its SN-38-Resistant Variant," Int. J. Cancer, vol. 72, 1997, pp. 680-686.
Kamath et al., "Challenges and advances in the assessment of the disposition of antibody-drug conjugates," Biopharmaceutics & Drug Disposition, 2015, 9 pages.
Kang et al, "Engineering multivalent antibodies to target heregulin-induced HER3 signaling in breast cancer cells, mAbs", Mar./Apr. 2014, vol. 6, No. 2, pp. 340-353.
Kaptain et al., "Her-2/neu and Breast Cancer," Diagn. Mol. Pathol. 10(3):139-152 (2001).
Karunagaran et al., "ErbB-2 is a common auxiliary subunit of NDF and EGF receptors: implications for breast cancer," EMBO J. 15(2):254-264 (1996).
Kawakami et al—"The anti-HER3 antibody patritumab abrogates cetuximab resistance mediated by heregulin in colorectal cancer cells", Oncotarget, vol. 5, No. 23, Dec.-May 2014, 11847-11856—10 pages.
Kimio Yonesaka, "Anti-HER3 Antibody Patritumab Overcomes Resistance to EGFR Inhibitor in Non-small Cell Lung Cancer", The Japan Lung Cancer Society, vol. 55, pp. 948-955, 2015 (8 pages).
Koebel et al., "Ovarian Carcinoma Subtypes Are Different Diseases: Implications for Biomarker Studies," PLoS Medicine, vol. 5, Issue 12, e232, Dec. 2008, pp. 1749-1760.
Korkaya et al., "HER2 regulates the mammary stem/progenitor cell population driving tumorigenesis and invasion," Oncogene 27:6120-6130 (2008).
Kraus et al., "Demonstration of ligand-dependent signaling by the erbB-3 tyrosine kinase and its constitutive activation in human breast tumor cells," Proc. Natl. Acad. Sci. USA 90:2900-2904 (Apr. 1993)—5 Pages.
Kraus et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (Dec. 1989)—5 pages.
Kumazawa et al., "Antitumor activity of DX-8951f: a new camptothecin derivative," Exp. Opin. Invest. Drugs 7(4):625-632 (1998)—8 Pages.
Kumazawa et al., "DE-310, a novel macromolecular carrier system for the camptothecin analog DX-8951f: Potent antitumor activities in various murine tumor models," Cancer Sci., vol. 95, No. 2, Feb. 2004, pp. 168-175.
Kumazawa et al., "Potent and broad antitumor effects of DX-8951f, a water-soluble camptothecin derivative, against various human tumors xenografted in nude mice," Cancer Chemother. Pharmacol., vol. 42, 1998, pp. 210-220.
Linnenbach et al., "Sequence investigation of the major gastrointestinal tumor-associated antigen gene family, GA733," Proc. Natl. Acad. Sci. 86(1):27-31 (Jan. 1989).
Lipinski et al., "Human trophoblast cell-surface antigens defined by monoclonal antibodies," Proc. Natl. Acad. Sci. 78(8):5147-5150 (Aug. 1981).
Loo et al., "Development of an Fc-Enhanced Anti-B7-H3 Monoclonal Antibody with Potent Antitumor Activity," Clinical Cancer Research, vol. 18, No. 4, Jul. 15, 2012, pp. 3834-3845.
Mah et al., "Kidney Development in Cadherin-6 Mutants: Delayed Mesenchyme-to-Epithelial Conversion and Loss of Nephrons," Developmental Biology, vol. 223, 2000, pp. 38-53.
Martin et al., "Constitutive Activity among Orphan Class-A G Protein Coupled Receptors," PLOS One, Sep. 18, 2015, pp. 1-12.
Masubuchi, N., "Pharmacokinetics of DE-310, a novel macromolecular carrier system for the camptothecin analog DX-8951f, in tumor-bearing mice," Pharmazie, vol. 59, No. 5, 2004, pp. 374-377.
McDonagh et al., "Engineered antibody-drug conjugates with defined sites and stoichiometries of drug attachment," Protein Engineering, Design & Selection, 2006, 19(7):299-307.
Mitsui et al., "A New Water-soluble Camptothecin Derivative, DX-8951f, Exhibits Potent Antitumor Activity against Human Tumors in vitro and in vivo," Jpn. J. Cancer Res, vol. 86, Aug. 1995, pp. 776-782.
Moghaddas et al., "Whether HER2-positive non-breast cancers are candidates for treatment with Ado-trastuzumab emtansine?" Journal of Research in Pharmacy Practice, vol. 5, No. 4, Oct.-Dec. 2016, pp. 227-233.
Momoko Hase et al: Characterization of an Orphan G Protein-coupled Receptor, GPR20, That Constitutively Activates G i Proteins:, Journal of Biological Chemistry, vol. 283, No. 19, May 9, 2008 (May 9, 2008), pp. 12747-12755.
Mühlmann et al., "TROP2 expression as prognostic marker for gastric carcinoma," J. Clin. Pathol. 62(2):152-158 (2009).
Naidu et al., "Expression of c-erbB3 protein in primary breast carcinomas," British Journal of Cancer 78(10): 1385-1390 (1998)—6 Pages.
Nakada et al., "Novel antibody drug conjugates containing exatecan derivative-based cytotoxic payloads," Bioorganic & Medicinal Chemistry Letters, vol. 26, 2016, pp. 1542-1545.
Ning et al., "TROP2 expression and its correlation with tumor proliferation and angiogenesis in human gliomas," Neurol. Sci. 34(10):1745-1750 (2013).
Non-Final Office Action issued in U.S. Appl. No. 14/435,114 mailed Jul. 21, 2016.
Non-Final Office Action issued in U.S. Appl. No. 14/436,458 mailed Jul. 19, 2016.
Non-Final Office Action issued in U.S. Appl. No. 15/180,203 mailed Jul. 25, 2016.
Non-Final Office Action issued in U.S. Appl. No. 15/187,179 mailed Oct. 21, 2016.
Non-Final Office Action issued in U.S. Appl. No. 15/221,851 mailed Jul. 7, 2017.
Notice of Allowance issued in U.S. Appl. No. 15/221,851 mailed Jun. 13, 2018.
Notice of Allowance issued in U.S. Appl. No. 15/187,179 mailed Aug. 25, 2017.
Notice of Allowance issued in U.S. Appl. No. 15/187,179 mailed May 18, 2017.
Notice of Grounds for Rejection issued in connection with Korean Patent Application No. 10-2016-7015961, dated May 1, 2018.
O'Dowd et al., "Cloning and chromosomal mapping of four putative novel human G-protein-coupled receptor genes," Gene. vol. 187, 1997, pp. 75-81.
Ochi et al., "A possible mechanism for the long-lasting antitumor effect of the macromolecular conjugate DE-310: mediation by cellular uptake and drug release of its active camptothecin analog DX-8951," Cancer Chemother Pharmacol, vol. 55, 2005, pp. 323-332.
Office Action dated Apr. 16, 2021 for corresponding Brazilian Patent Application No. BR112015006521-0.
Office Action in corresponding application No. PCT/JP2017/036215 dated Nov. 21, 2017.
Office Action issued on Oct. 7, 2020 for corresponding Japanese Patent Application No. 2019-518773.
Office Action with Search Report dated Aug. 29, 2017, in RU 2015113767.
Ogitani et al., "Wide application of a novel topoisomerase I inhibitor-based drug conjugation technology," Bioorganic & Medicinal Chemistry Letters, vol. 26, 2016, 5069-5072.
Oguma et al., "Validation study of a method for assaying DE-310, a macromolecular carrier conjugate containing an anti-tumor camptothecin derivative, and the free drug in tumor tissue by high

(56) References Cited

OTHER PUBLICATIONS performance liquid chromatography/atmospheric pressure chemical ionization tandem mass spectrometry," Biomedical Chromatography, vol. 19, 2005, pp. 19-26.
Ohmachi et al., "Clinical Significance of TROP2 Expression in Colorectal Cancer," Clin. Cancer Res. 12(10):3057-3063 (May 15, 2006).
Opposition dated May 9, 2017, against CO NC2016/0000187, with partial English translation.
Osterhout et al., "Cadherin-6 Mediates Axon-Target Matching in a Non-Image-Forming Visual Circuit," Neuron Report, vol. 71, Aug. 25, 2011, pp. 632-639.
Paul et al., "Cadherin-6, a Cell Adhesion Molecule Specifically Expressed in the Proximal Renal Tubule and Renal Cell Carcinoma," Cancer Research, vol. 57, Jul. 1, 1997, pp. 2741-2748.
Perez et al., "Antibody-drug conjugates: current status and future directions," Drug Discovery Today, vol. 19, No. 7, Jul. 2014, pp. 869-881.
Peters et al., "Antibody-drug conjugates as novel anti-cancer chemotherapeutics," Bioscience Reports, vol. 35, 2015, pp. 1-20.
Plowman et al., "Molecular cloning and expression of an additional epidermal growth factor receptor-related gene," Proc. Natl. Acad. Sci. USA 87:4905-4909 (Jul. 1990)—5 Pages.
Polakis, Paul, "Antibody Drug Conjugates for Cancer Therapy," Pharmacological Reviews, vol. 68, pp. 3-19, Jan. 2016.
Ripani et al., "Human Trop-2 is a Tumor-Associated Calcium Signal Transducer," Int. J. Cancer 76(5):671-676 (1998).
Rowinsky et al., "Preclinical and Clinical Development of Exatecan (DX-8951f), A Hexacyclic Camptothecin Analog," Camptothecins in Cancer Therapy, Chapter 14, 2005, pp. 317-341.
Russian Office Action dated Mar. 5, 2019 in corresponding application No. 2016143351.
Russian Office Action dated Oct. 11, 2018 in corresponding application No. 2016123597.
Scott et al., "Antibody therapy of cancer," Nature Reviews, vol. 12, Apr. 2012, pp. 278-287.
Search Report and Written Opinion dated Apr. 8, 2021 for corresponding Brazil Patent Application No. BR112016013482-6.
Search Report and Written Opinion dated Apr. 8, 2021 for corresponding Brazil Patent Application No. BR122020020973-9.
Sergina, N.V., et al. "Escape from HER-family tyrosine kinase inhibitor therapy by the kinase-inactive HER3", Nature, vol. 445, pp. 437-441, 2007 (6 pages).
Shen et al., "Conjugation site modulates the in vivo stability and therapeutic activity of antibody-drug conjugates," Nature Biotechnology, vol. 30, Jan. 22, 2012, pp. 184-189.
Shimazui et al., "The Level of Cadherin-6 mRNA in Peripheral Blood Is Associated with the Site of Metastasis and with the Subsequent Occurrence of Metastases in Renal Cell Carcinoma," Cancer, vol. 101, No. 5, Sep. 1, 2004, pp. 963-968.
Shimoyama et al., "Isolation and Sequence Analysis of Human Cadherin-6 Complementary DNA for the Full Coding Sequence and Its Expression in Human Carcinoma Cells," Cancer Research, vol. 55, May 15, 1995, pp. 2206-2211.
Shiose et al., "Systematic Research of Peptide Spacers Controlling Drug Release from Macromolecular Prodrug System, Carboxymethyldextran Polyalcohol-Peptide-Drug Conjugates," Bioconjugate Chem., vol. 20, 2009, pp. 60-70.
Shiose et al., "Relationship between Drug Release of DE-310, Macromolecular Prodrug of DX-8951f, and Cathepsins Activity in Several Tumors," Biol. Pharm. Bull., 2007, 30(12):2365-2370.
Sievers et al., "Antibody-Drug Conjugates in Cancer Therapy," Annual Review of Medicine, vol. 64, 2013, pp. 15-29.
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Sliwkowski et al., "Nonclinical Studies Addressing the Mechanism of Action of Trastuzumab (Herceptin)," Semin. Oncol. 26(4) Suppl. 12: 60-70 (Aug. 1999).
Sliwkowski et al., "Coexpression of erbB2 and erbB3 Proteins Reconstitutes a High Affinity Receptor for Heregulin." J. Biol. Chem. 269(20):14661-14665 (1994).
Soepenberg et al., "Liquid chromatographic assays for DE-310, a novel camptothecin analog, and two major enzymatic products in human matrices," Journal of Chromatography B, vol. 799, 2004, pp. 15-22.
Soepenberg et al., "Phase I and Pharmacokinetic Study of DE-310 in Patients with Advanced Solid Tumors," Clin. Cancer Res. 11:703-711 (Jan. 15, 2005)—9 Pages.
Stepan et al., "Expression of Trop2 Cell Surface Glycoprotein in Normal and Tumor Tissues: Potential Implications as a Cancer Therapeutic Target," Journal of Histochemistry & Cytochemistry vol. 59, No. 7, pp. 701-710.
Taiwanese Office Action dated Jul. 30, 2018 in corresponding application No. 104111534.
Taiwanese Office Action dated May 15, 2017 in corresponding application No. 102136742.
Takiguchi et al., "Antitumor Effect of DX-8951, a Novel Camptothecin Analog, on Human Pancreatic Tumor Cells and Their CPT-11-resistant Variants Cultured in vitro and Xenografted in Nude Mice," Jpn. J. Cancer Res., vol. 88, Aug. 1997, pp. 760-769.
The State Intellectual Property Office of People's Republic of China, "The First Office Action," issued in connection with Chinese Patent Application No. 201380053256.2, dated Nov. 1, 2016.
The State Intellectual Property Office of People's Republic of China, "The First Office Action," issued in connection with Chinese Patent Application No. 201480071134.0, dated Aug. 20, 2019.
Tsuchikama et al., "Antibody-drug conjugates: recent advances in conjugation and linker chemistries," Protein & Cell, Oct. 14, 2016, 14 pages.
United States Office Action dated Apr. 5, 2019 in U.S. Appl. No. 15/821,697.
US Patent and Trademark Office, "Non-Final Office Action," issued in connection with U.S. Appl. No. 15/821,662, dated Jan. 17, 2018.
US Patent and Trademark Office, "Notice of Allowance," issued in connection with U.S. Appl. No. 15/821,662, dated Nov. 2, 2018.
Velez et al., "APOE*E2 allele delays age of onset in PSEN1 E280A Alzheimer's disease," Molecular Psychiatry, 2015, pp. 1-9.
Vogel et al., "Efficacy and Safety of Trastuzumab as a Single Agent in First-Line Treatment of HER2-Overexpressing Metastatic Breast Cancer," J. Clin. Oncol. 20(3):719-726 (Feb. 2002).
Wang et al., "Identification of Trop-2 as an oncogene and an attractive therapeutic target in colon cancers," Mol. Cancer Ther. 7(2):280-285 (Feb. 2008).
Wente et al., "DE-310, a macromolecular prodrug of the topoisomerase-I-inhibitor exatecan (DX-8951), in patients with operable solid tumors," Investigational New Drugs, vol. 23, 2005, pp. 339-347.
Yamaguchi, Teruhide, "Current situations and the future prospect of monoclonal antibody products," Report of the National Institute of Health, vol. 132, 2014, pp. 36-46.
Yano et al., "Comparison of HER2 gene amplification assessed by fluorescence in situ hybridization and HER2 protein expression assessed by immunohistochemistry in gastric cancer," Oncol. Rep. 15:65-71 (2006).
Yokoi et al., "A Novel Target Gene, SKP2, within the 5p13 Amplicon That Is Frequently Detected in Small Cell Lung Cancers," The American Journal of Pathology, vol. 161, Issue 1, Jul. 2002, pp. 207-216.
Yonesaka, K., et al., "Anti-HER3 monoclonal antibody patritumab sensitizes refractory non-small cell lung cancer to the epidermal growth factor receptor inhibitor erlotinib", Oncogene vol. 35, pp. 878-886, 2016 (10 pages).
European Extended Search Report issued in corresponding European Patent Application No. 19842020.0 dated Mar. 22, 2022 (8 pages).
Office Action issued in corresponding Chinese Patent Application No. 201980049551.8 dated Feb. 22, 2024 (13 pages).
Office Action issued in corresponding Chinese Patent Application No. 201980049551.8 dated Sep. 1, 2023 (11 pages).

(56) References Cited

OTHER PUBLICATIONS

Office Action issued in corresponding Indian Patent Application No. 202117007610 dated Apr. 19, 2021 (6 pages).
Office Action issued in corresponding Israeli Patent Application No. 280,295 dated Jul. 3, 2023 (9 pages).
Office Action issued in corresponding Japanese Patent Application No. 2020-532431 dated May 30, 2023 (5 pages).
Office Action issued in corresponding Singaporean Patent Application No. 11202100653Y dated Oct. 3, 2022 (10 pages).
Office Action issued in corresponding Taiwanese Patent Application No. 108126115 dated Jul. 11, 2023 (10 pages).
International Searching Authority, "International Search Report," issued in connection with International Patent Application No. PCT/JP2019/029379, dated Oct. 21, 2019.
International Searching Authority, "Written Opinion," issued in connection with International Patent Application No. PCT/JP2019/029379, dated Oct. 21, 2019.
Agatsuma, Toshinori, "Antibody drugs and antibody-drug conjugates (ADCs) and Daiichi Sankyo's efforts," (Mar. 29, 2017), URL: https://www.daiichisankyo.co.jp/ir/calendar/files/005347/DS.pdf, (Sep. 20, 2019).
Alley et al., "Antibody-drug conjugates: targeted drug delivery for cancer," Current Opinion in Chemical Biology, vol. 14, 2010, pp. 529-537.
Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," Journal of Clinical Oncology, vol. 29, No. 4, Feb. 1, 2011, pp. 398-405.
Damle, Nitin K., "Tumour-targeted chemotherapy with immunoconjugates of calicheamicin," Expert Opin. Biol. Ther., vol. 4, No. 9, 2004, pp. 1445-1452.
Dere et al., PK assays for antibody-drug conjugates: case study with ado-trastuzumab emtansine, Bioanalysis, vol. 5, No. 9, May 2013, pp. 1025-1040.
Doi et al., "Safety, pharmacokinetics, and antitumour activity of trastuzumab deruxtecan (DS-8201), a HER2-targeting antibody-drug conjugate, in patients with advanced breast and gastric or gastro-oesophageal tumours: a phase 1 dose-escalation study," The Lancet Oncology, vol. 18, Issue 11, Nov. 1, 2017, pp. 1512-1522.
Ducry et al., "Antibody-Drug Conjugates: Linking Cytotoxic Payloads to Monoclonal Antibodies," Bioconjugate Chem, vol. 21, 2010, pp. 5-13.
Kaur et al., Bioanalytical assay strategies for the development of antibody-drug conjugate biotherapeutics, Bioanalysis, vol. 5, No. 2, Jan. 2013, pp. 201-226.
Nakayama et al., "FY2016 financial results Management briefing," online, (Sep. 20, 2019), URL: https://www.daiichisankyo.co.jp/ir/calendar/files/005344/pdf.
Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, vol. 107, 2016, pp. 1039-1046.
Ogitani et al., "DS-8201a, A Novel HER2-Targeting ADC with a Novel DNA Topoisomerase I Inhibitor, Demonstrates a Promising Antitumor Efficacy with Differentiation from T-DM1," Clinical Cancer Research, vol. 22, No. 20, Oct. 15, 2016, pp. 5097-5108.
Sanderson et al., "In vivo Drug-Linker Stability of an Anti-CD30 Dipeptide-Linked Auristatin Immunoconjugate," Clinical Cancer Research, vol. 11, No. 2, Jan. 2005, pp. 843-852.
Senter et al., "The discovery and development of brentuximab vedotin for use in relapsed Hodgkin lymphoma and systemic anaplastic large cell lymphoma," Nature Biotechnology, vol. 30, No. 7, Jul. 2012, pp. 631-637.
Stephan et al., "Anti-CD22-MCC-DM1 and MC-MMAF conjugates: impact of assay format on pharmacokinetic parameters determination," Bioconjugate Chemistry, vol. 19, No. 8, Aug. 2008, pp. 1673-1683.
Stephan et al., "Challenges in developing bioanalytical assays for characterization of antibody-drug conjugates," Bioanalysis, vol. 3, No. 6, Mar. 2011, pp. 677-700.
Takegawa et al., "DS-8201a, a new HER2-targeting antibody-drug conjugate incorporating a novel DNA topoisomerase I inhibitor, overcomes HER2-positive gastric cancer T-DM1 resistance," International Journey of Cancer, vol. 141, 2017, pp. 1682-1689.
Xie et al., "Pharmacokinetics and Biodistribution of the Antitumor Immunoconjugate, Cantuzumab Mertansine (huC242-DM1), and Its Two Components in Mice," Journal of Pharmacology and Experimental Therapeutics, vol. 308, No. 3, Apr. 2004, pp. 1073-1082.

\* cited by examiner

[Figure 1]

SEQ ID NO: 15 - Amino acid sequence of a heavy chain of mouse antibody 1A3

MKHLWFFLLLVAAPRWVLSEVKLVESGGGLVQPGGSRK
LSCAASGFTFSDYGMVWIRQAPGRGLEWVAYISSGSSA
IYYADTVKGRFTISRDNPKNTLFLQMNSLRSEDSAMYF
CARPPRYDVYSAWFAYWGQGTLVTVSAAKTTPPSVYPL
APGCGDTTGSSVTSGCLVKGYFPEPVTVTWNSGSLSSS
VHTFPALLQSGLYTMSSSVTVPSSTWPSQTVTCSVAHP
ASSTTVDKKLEPSGPISTINPCPPCKECHKCPAPNLEG
GPSVFIFPPNIKDVLMISLTPKVTCVVVDVSEDDPDVQ
ISWFVNNVEVHTAQTQTHREDYNSTIRVVSTLPIQHQD
WMSGKEFKCKVNNKDLPSPIERTISKIKGLVRAPQVYT
LPPPAEQLSRKDVSLTCLVVGFNPGDISVEWTSNGHTE
ENYKDTAPVLDSDGSYFIYSKLNMKTSKWEKTDSFSCN
VRHEGLKNYYLKKTISRSPGK

Signal sequence (1-19), Heavy chain variable region (20-141), Heavy chain constant region (142-477)

[Figure 2]

SEQ ID NO: 16 - Amino acid sequence of a light chain of mouse antibody 1A3

MVLQTQVFISLLLWISGAYGDIVMTQSHKFMSTSVGDRVS
ITCKASQDVGSAVVWYQQKPGHSPDLLIYWASTRHTGVPD
RFTGSGSGTDFTLTIGNVQSEDLADYFCQQYSSYPVTFGG
GTKLEIKRADAAPTVSIFPPSSEQLTSGGASVVCFLNNFY
PKDINVKWKIDGSERQNGVLNSWTDQDSKDSTYSMSSTLT
LTKDEYERHNSYTCEATHKTSTSPIVKSFNRNEC

Signal sequence (1-20), Light chain variable region (21-127), Light chain constant region (128-234)

[Figure 3]

SEQ ID NO: 17 - Nucleotide sequence encoding the amino acid sequence of a heavy chain variable region of mouse antibody 1A3 atggactccaggctcaatttagttttccttgtccttat
tttaaaaggtgtccagtgtGAGGTGAAGCTGGTGGAGT
CTGGGGGAGGCTTAGTGCAGCCTGGAGGGTCCCGGAAA
CTCTCCTGTGCAGCCTCTGGATTCACTTTCAGTGACTA
CGGAATGGTGTGGATTCGACAGGCTCCAGGGAGGGGGC
TGGAGTGGGTTGCATACATTAGTAGTGGCAGTAGTGCC
ATCTACTATGCAGACACAGTGAAAGGCCGATTCACCAT
CTCCAGAGACAATCCCAAGAACACCCTGTTCCTGCAAA
TGAACAGTCTAAGGTCTGAGGACTCGGCCATGTATTTC
TGTGCAAGGCCCCCCGTTATGATGTTTACTCTGCCTG
GTTTGCTTACTGGGGCCAAGGGACTCTGGTCACTGTCT
CTGCAgccaaaacaacacccccatcagtctatccactg
gcccctgggtgtggagatacaactggttcctccgtgac
tctgggatgc Signal sequence (1-57), Heavy chain variable region (58-423)

[Figure 4]

SEQ ID NO: 18 - Nucleotide sequence encoding the amino acid sequence of a light chain variable region of mouse antibody 1A3 atggagacacattctcaggtctttgtatacatgttgct
gtggttgtctgatgttgaaggaGACATTGTGATGACCC
AGTCTCACAAATTCATGTCCACATCTGTAGGAGACAGG
GTCAGCATCACCTGCAAGGCCAGTCAGGATGTGGGTAG
TGCTGTAGTCTGGTATCAACAGAAACCTGGGCACTCTC
CTGACCTACTGATTTACTGGGCATCCACCCGGCACACT
GGAGTCCCTGATCGCTTCACAGGCAGTGGATCTGGGAC
AGATTTCACGCTCACCATTGGCAATGTGCAGTCTGAAG
ACTTGGCAGATTATTTCTGTCAGCAATATAGCAGCTAT
CCTGTCACGTTCGGAGGGGGGACCAAGCTGGAAATAAA
Acgggctgatgctgcaccaactgtatccatcttcccac
catccagtgagcagttaacatctggaggtgcctcagtc
gtg Signal sequence (1-60), Light chain variable region (61-381)

[Figure 5]

SEQ ID NO: 19 - Amino acid sequence of a heavy chain of rabbit chimeric antibody 1A3

MKHLWFFLLLVAAPRWVLSEVKLVESGGGLVQPGGSRKLS
CAASGFTFSDYGMVWIRQAPGRGLEWVAYISSGSSAIYYA
DTVKGRFTISRDNPKNTLFLQMNSLRSEDSAMYFCARPPR
YDVYSAWFAYWGQGTLVTVSAGQPKAPSVFPLAPCCGDTP
SSTVTLGCLVKGYLPEPVTVTWNSGTLTNGVRTFPSVRQS
SGLYSLSSVVSVTSSSQPVTCNVAHPATNKVDKTVAPST
CSKPTCPPPELLGGPSVFIFPPKPKDTLMISRTPEVTCVV
VDVSQDDPEVQFTWYINNEQVRTARPPLREQQFNSTIRVV
STLPITHQDWLRGKEFKCKVHNKALPAPIEKTISKARGQP
LEPKVYTMGPPREELSSRSVSLTCMINGFYPSDISVEWEK
NGKAEDNYKTTPAVLDSDGSYFLYNKLSVPTSEWQRGDVF
TCSVMHEALHNHYTQKSISRSPGK

Signal sequence (1-19), Heavy chain variable region (20-141), Heavy chain constant region (142-464)

[Figure 6]

SEQ ID NO: 20 - Amino acid sequence of a light chain of rabbit chimeric antibody 1A3

MVLQTQVFISLLLWISGAYGDIVMTQSHKFMSTSVGDRVS
ITCKASQDVGSAVVWYQQKPGHSPDLLIYWASTRHTGVPD
RFTGSGSGTDFTLTIGNVQSEDLADYFCQQYSSYPVTFGG
GTKLEIKRDPVAPSVLLFPPSKEELTTGTATIVCVANKFY
PSDITVTWKVDGTTQQSGIENSKTPQSPEDNTYSLSSTLS
LTSAQYNSHSVYTCEVVQGSASPIVQSFNRGDC

Signal sequence (1-20), Light chain variable region (21-127), Light chain constant region (128-233)

[Figure 7]

SEQ ID NO: 21 - Amino acid sequence of a heavy chain of the anti-HER2 antibody

EVQLVESGGGLVQPGGSLRLSCAASGFNIKDTYIHWVR
QAPGKGLEWVARIYPTNGYTRYADSVKGRFTISADTSK
NTAYLQMNSLRAEDTAVYYCSRWGGDGFYAMDYWGQGT
LVTVSSASTKGPSVFPLAPSSKSTSGGTAALGCLVKDY
FPEPVTVSWNSGALTSGVHTFPAVLQSSGLYSLSSVVT
VPSSSLGTQTYICNVNHKPSNTKVDKKVEPKSCDKTHT
CPPCPAPELLGGPSVFLFPPKPKDTLMISRTPEVTCVV
VDVSHEDPEVKFNWYVDGVEVHNAKTKPREEQYNSTYR
VVSVLTVLHQDWLNGKEYKCKVSNKALPAPIEKTISKA
KGQPREPQVYTLPPSREEMTKNQVSLTCLVKGFYPSDI
AVEWESNGQPENNYKTTPPVLDSDGSFFLYSKLTVDKS
RWQQGNVFSCSVMHEALHNHYTQKSLSLSPGK

[Figure 8]

SEQ ID NO: 22 - Amino acid sequence of a light chain of the anti-HER2 antibody

DIQMTQSPSSLSASVGDRVTITCRASQDVNTAVAWYQQ
KPGKAPKLLIYSASFLYSGVPSRFSGSRSGTDFTLTIS
SLQPEDFATYYCQQHYTTPPTFGQGTKVEIKRTVAAPS
VFIFPPSDEQLKSGTASVVCLLNNFYPREAKVQWKVDN
ALQSGNSQESVTEQDSKDSTYSLSSTLTLSKADYEKHK
VYACEVTHQGLSSPVTKSFNRGEC

[Figure 9]

SEQ ID NO: 23 - Amino acid sequence of a heavy chain of the anti-HER3 antibody

QVQLQQWGAGLLKPSETLSLTCAVYGGSFSGYYWSWIR
QPPGKGLEWIGEINHSGSTNYNPSLKSRVTISVETSKN
QFSLKLSSVTAADTAVYYCARDKWTWYFDLWGRGTLVT
VSSASTKGPSVFPLAPSSKSTSGGTAALGCLVKDYFPE
PVTVSWNSGALTSGVHTFPAVLQSSGLYSLSSVVTVPS
SSLGTQTYICNVNHKPSNTKVDKRVEPKSCDKTHTCPP
CPAPELLGGPSVFLFPPKPKDTLMISRTPEVTCVVVDV
SHEDPEVKFNWYVDGVEVHNAKTKPREEQYNSTYRVVS
VLTVLHQDWLNGKEYKCKVSNKALPAPIEKTISKAKGQ
PREPQVYTLPPSREEMTKNQVSLTCLVKGFYPSDIAVE
WESNGQPENNYKTTPPVLDSDGSFFLYSKLTVDKSRWQ
QGNVFSCSVMHEALHNHYTQKSLSLSPGK

[Figure 10]

SEQ ID NO: 24 - Amino acid sequence of a light chain of the anti-HER3 antibody

DIEMTQSPDSLAVSLGERATINCRSSQSVLYSSSNRNY
LAWYQQNPGQPPKLLIYWASTRESGVPDRFSGSGSGTD
FTLTISSLQAEDVAVYYCQQYYSTPRTFGQGTKVEIKR
TVAAPSVFIFPPSDEQLKSGTASVVCLLNNFYPREAKV
QWKVDNALQSGNSQESVTEQDSKDSTYSLSSTLTLSKA
DYEKHKVYACEVTHQGLSSPVTKSFNRGEC

[Figure 11]

SEQ ID NO: 25 - Amino acid sequence of a heavy chain of the anti-TROP2 antibody

MKHLWFFLLLVAAPRWVLSQVQLVQSGAEVKKPGASVK
VSCKASGYTFTTAGMQWVRQAPGQGLEWMGWINTHSGV
PKYAEDFKGRVTISADTSTSTAYLQLSSLKSEDTAVYY
CARSGFGSSYWYFDVWGQGTLVTVSSASTKGPSVFPLA
PSSKSTSGGTAALGCLVKDYFPEPVTVSWNSGALTSGV
HTFPAVLQSSGLYSLSSVVTVPSSSLGTQTYICNVNHK
PSNTKVDKRVEPKSCDKTHTCPPCPAPELLGGPSVFLF
PPKPKDTLMISRTPEVTCVVVDVSHEDPEVKFNWYVDG
VEVHNAKTKPREEQYNSTYRVVSVLTVLHQDWLNGKEY
KCKVSNKALPAPIEKTISKAKGQPREPQVYTLPPSREE
MTKNQVSLTCLVKGFYPSDIAVEWESNGQPENNYKTTP
PVLDSDGSFFLYSKLTVDKSRWQQGNVFSCSVMHEALH
NHYTQKSLSLSPGK

Signal sequence (1-19), Variable region (20-140), Constant region (141-470)

[Figure 12]

SEQ ID NO: 26 - Amino acid sequence of a light chain of the anti-TROP2 antibody

MVLQTQVFISLLLWISGAYGDIQMTQSPSSLSASVGDR
VTITCKASQDVSTAVAWYQQKPGKAPKLLIYSASYRYT
GVPSRFSGSGSGTDFTLTISSLQPEDFAVYYCQQHYIT
PLTFGQGTKLEIKRTVAAPSVFIFPPSDEQLKSGTASV
VCLLNNFYPREAKVQWKVDNALQSGNSQESVTEQDSKD
STYSLSSTLTLSKADYEKHKVYACEVTHQGLSSPVTKS
FNRGEC

Signal sequence (1-20), Variable region (21-129), Constant region (130-234)

[Figure 13]

SEQ ID NO: 27 - Amino acid sequence of a heavy chain of the anti-B7-H3 antibody

MKHLWFFLLLVAAPRWVLSQVQLVQSGAEVKKPGSSVK
VSCKASGYTFTNYVMHWVRQAPGQGLEWMGYINPYNDD
VKYNEKFKGRVTITADESTSTAYMELSSLRSEDTAVYY
CARWGYYGSPLYYFDYWGQGTLVTVSSASTKGPSVFPL
APSSKSTSGGTAALGCLVKDYFPEPVTVSWNSGALTSG
VHTFPAVLQSSGLYSLSSVVTVPSSSLGTQTYICNVNH
KPSNTKVDKRVEPKSCDKTHTCPPCPAPELLGGPSVFL
FPPKPKDTLMISRTPEVTCVVVDVSHEDPEVKFNWYVD
GVEVHNAKTKPREEQYNSTYRVVSVLTVLHQDWLNGKE
YKCKVSNKALPAPIEKTISKAKGQPREPQVYTLPPSRE
EMTKNQVSLTCLVKGFYPSDIAVEWESNGQPENNYKTT
PPVLDSDGSFFLYSKLTVDKSRWQQGNVFSCSVMHEAL
HNHYTQKSLSLSPGK

Signal sequence (1-19), Variable region (20-141), Constant region (142-471)

[Figure 14]

SEQ ID NO: 28 - Amino acid sequence of a light chain of the anti-B7-H3 antibody

MVLQTQVFISLLLWISGAYGEIVLTQSPATLSLSPGER
ATLSCRASSRLIYMHWYQQKPGQAPRPLIYATSNLASG
IPARFSGSGSGTDFTLTISSLEPEDFAVYYCQQWNSNP
PTFGQGTKVEIKRTVAAPSVFIFPPSDEQLKSGTASVV
CLLNNFYPREAKVQWKVDNALQSGNSQESVTEQDSKDS
TYSLSSTLTLSKADYEKHKVYACEVTHQGLSSPVTKSF
NRGEC

Signal sequence (1-20), Variable region (21-128), Constant region (129-233)

[Figure 15]
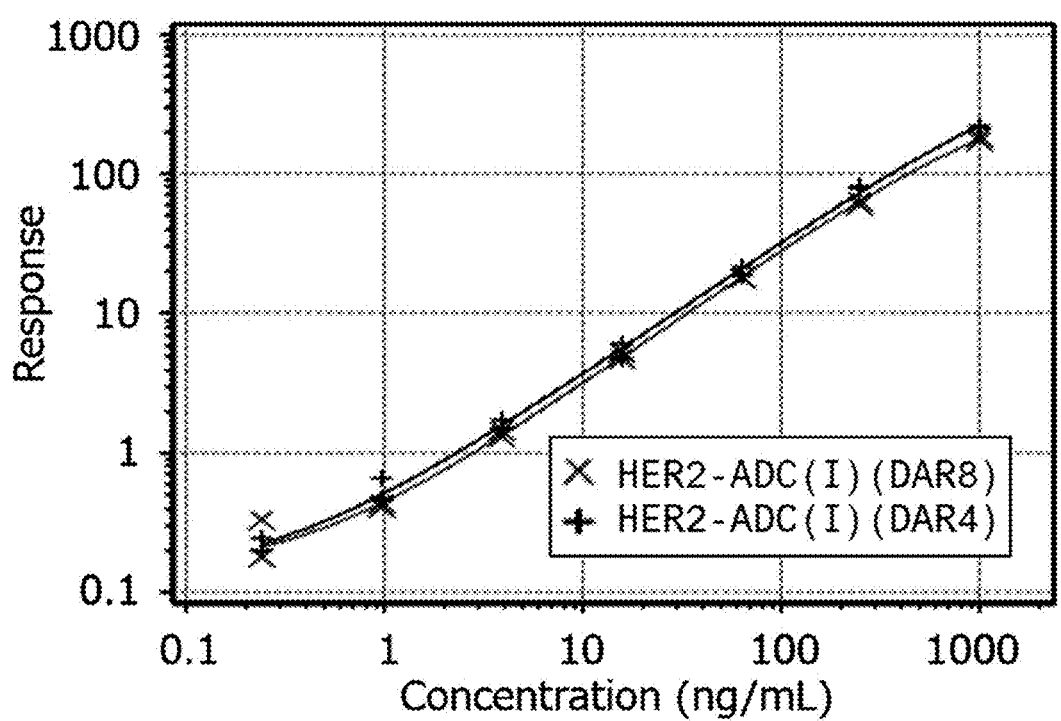

[Figure 16]
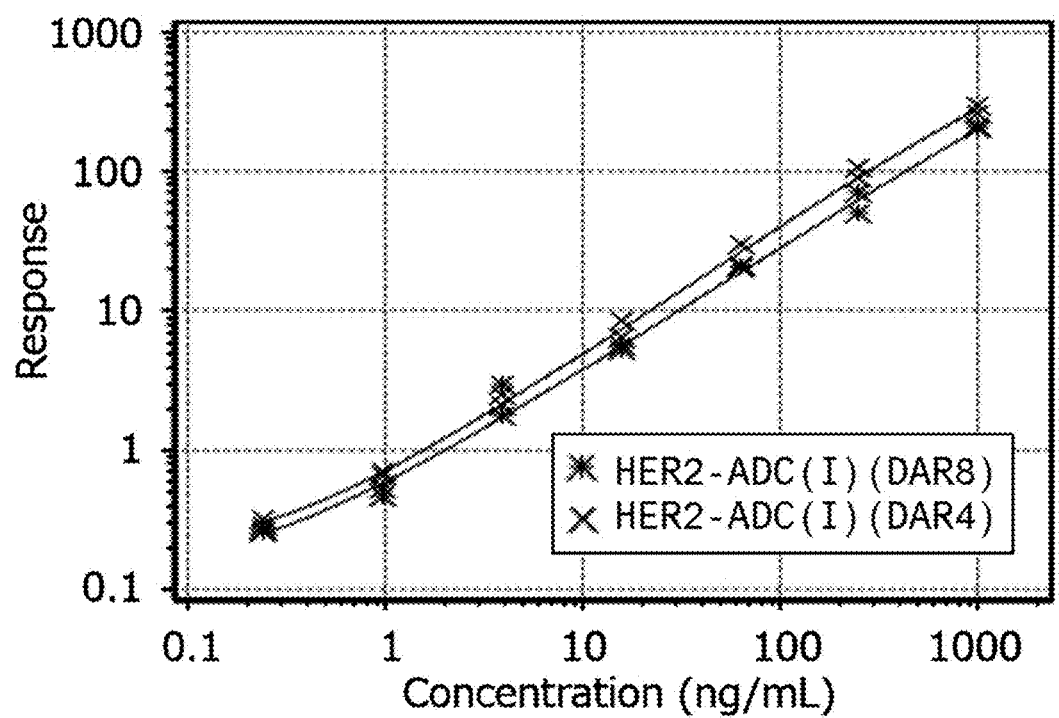

[Figure 17]
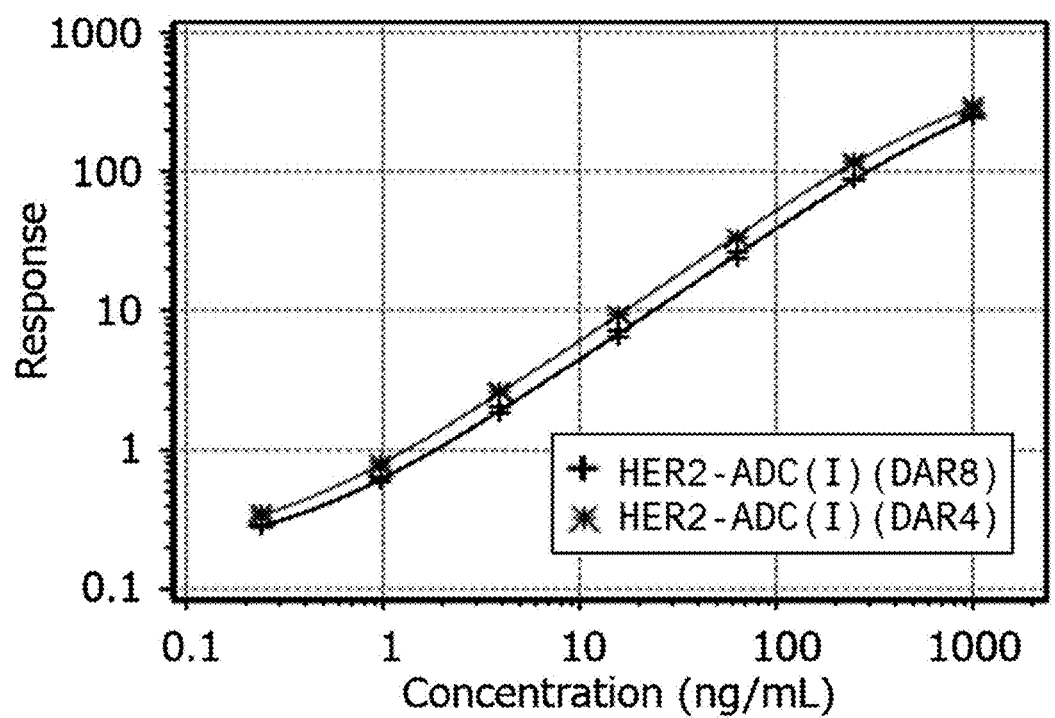

[Figure 18]
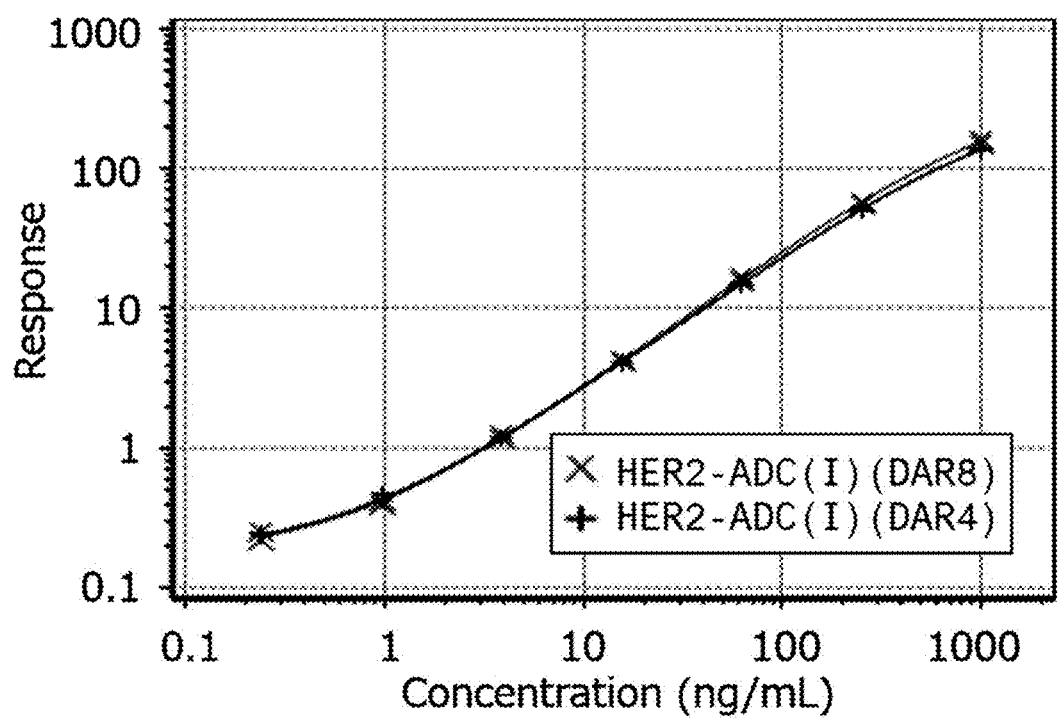

[Figure 19]
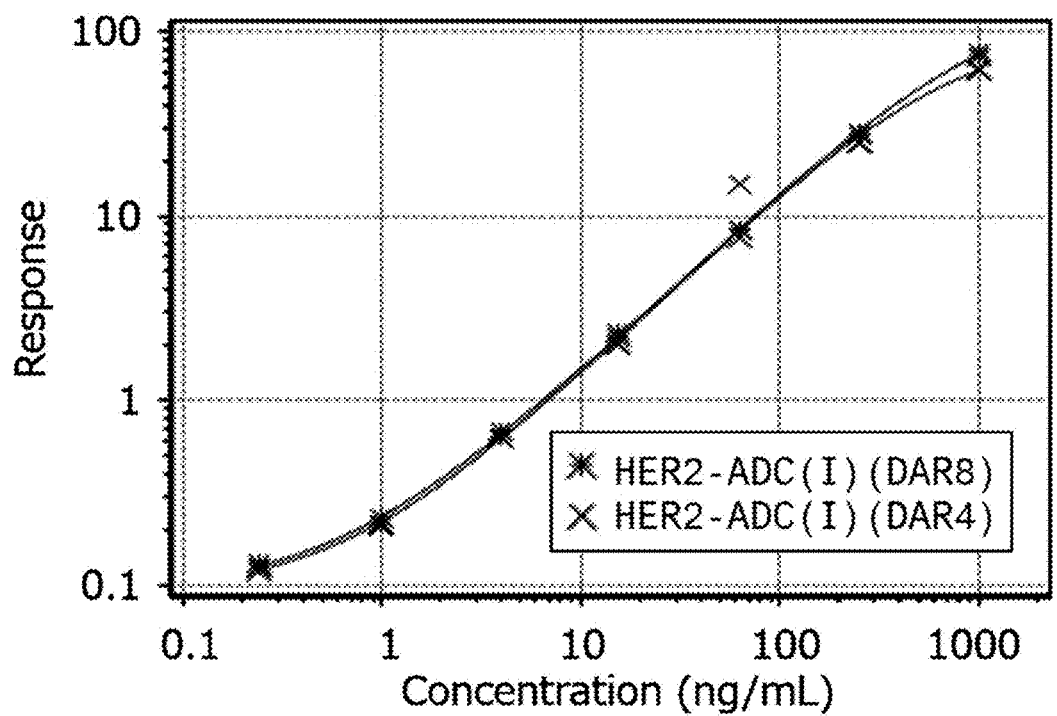

[Figure 20]
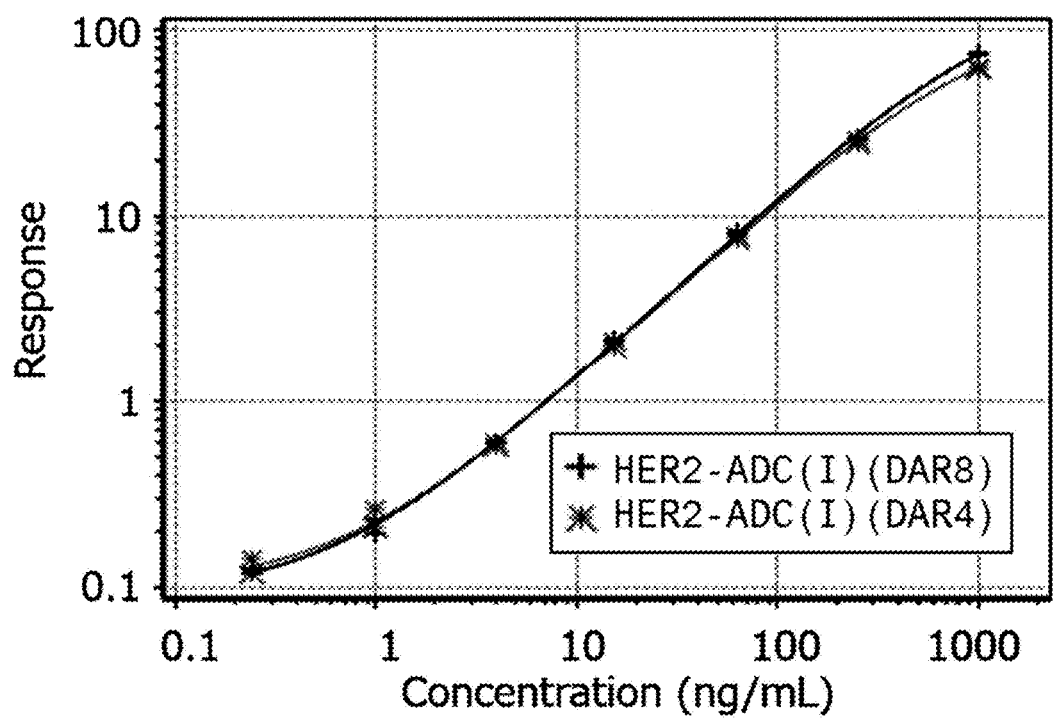

[Figure 21]
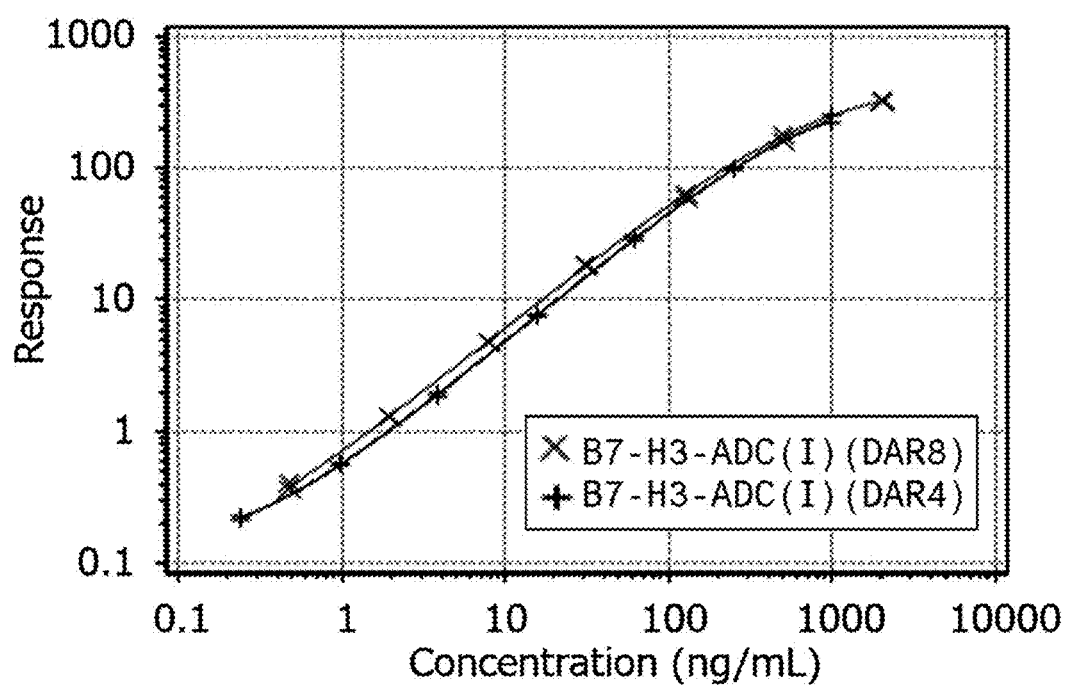

[Figure 22]
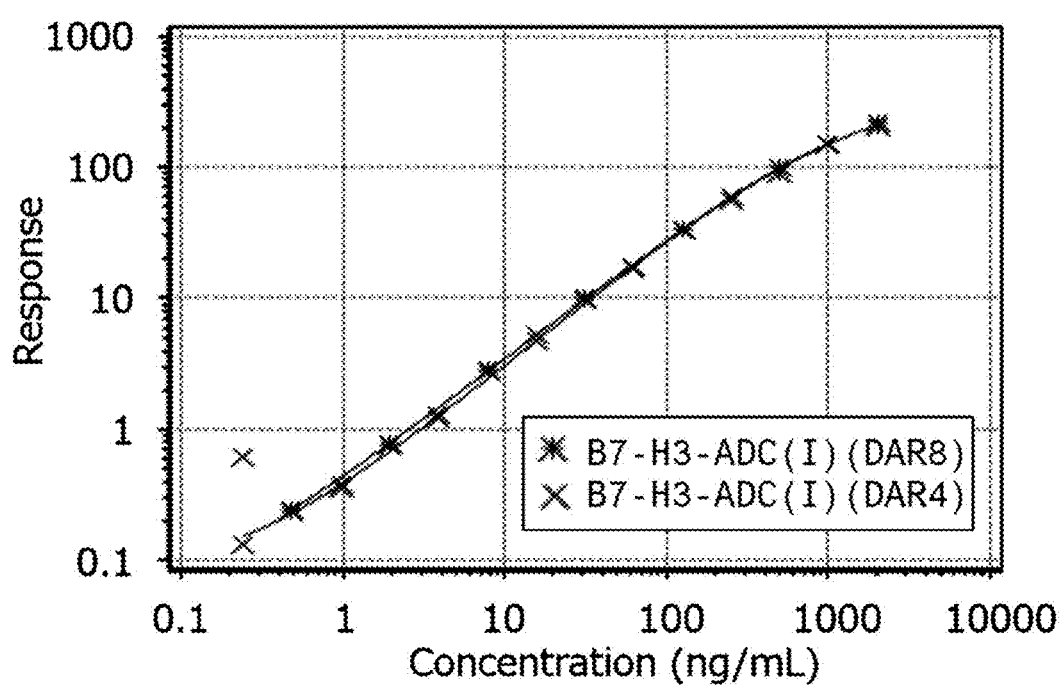

[Figure 23]
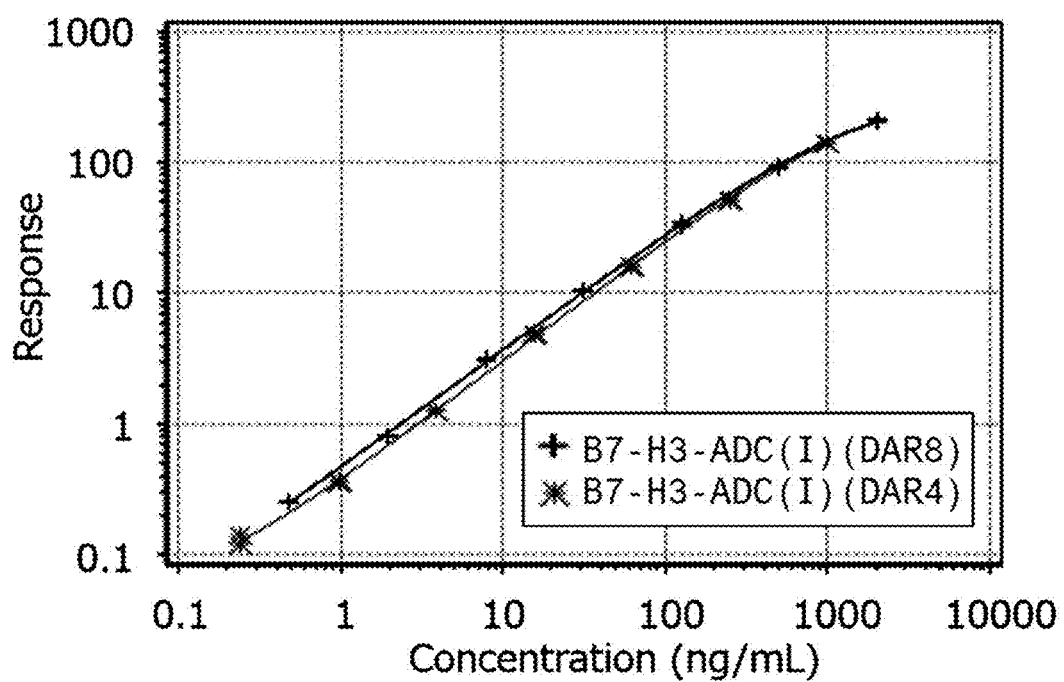

[Figure 24]
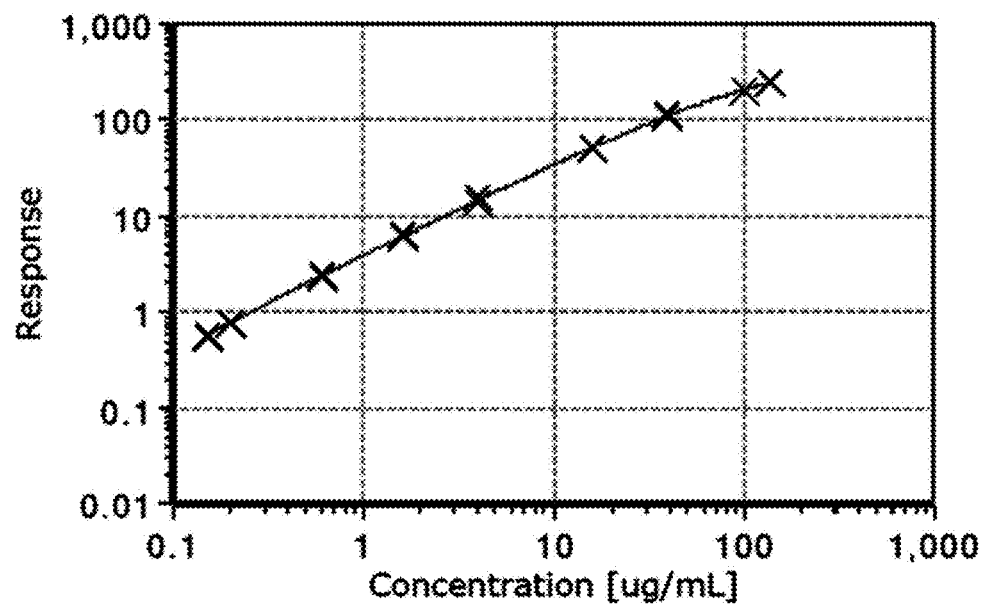

[Figure 25]
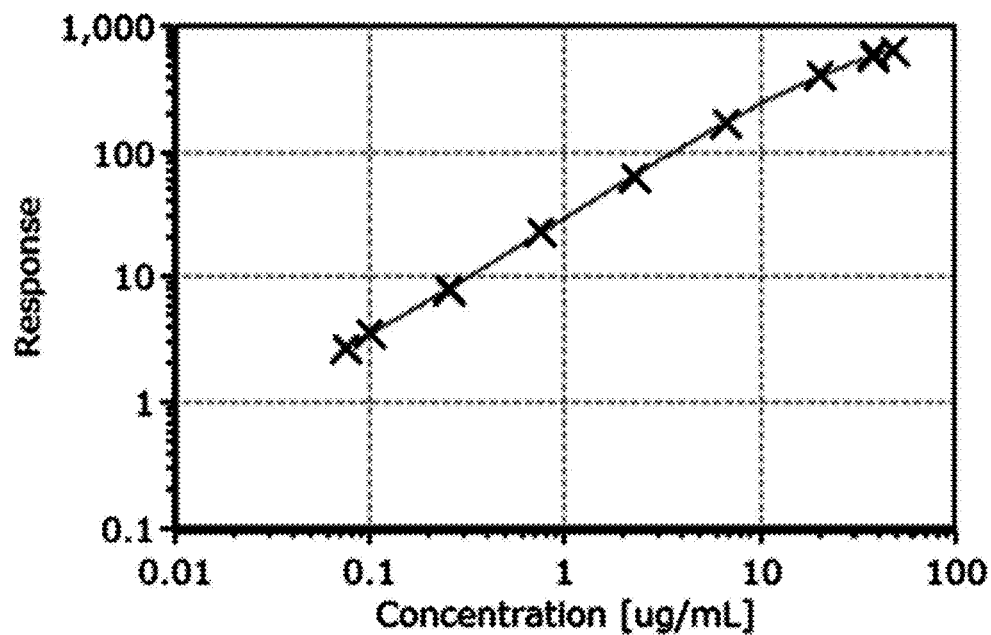

[Figure 26]
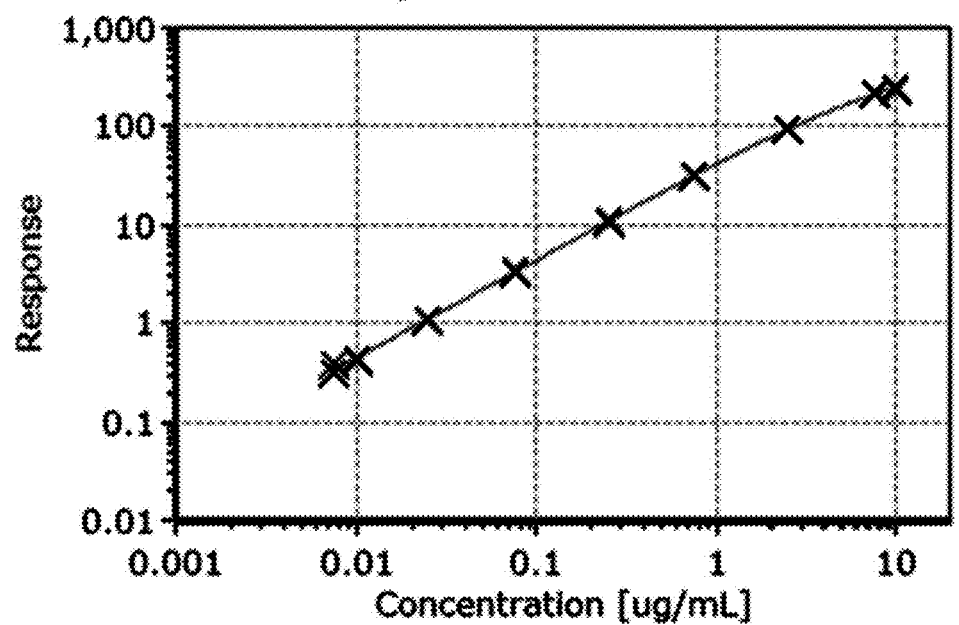

[Figure 27]
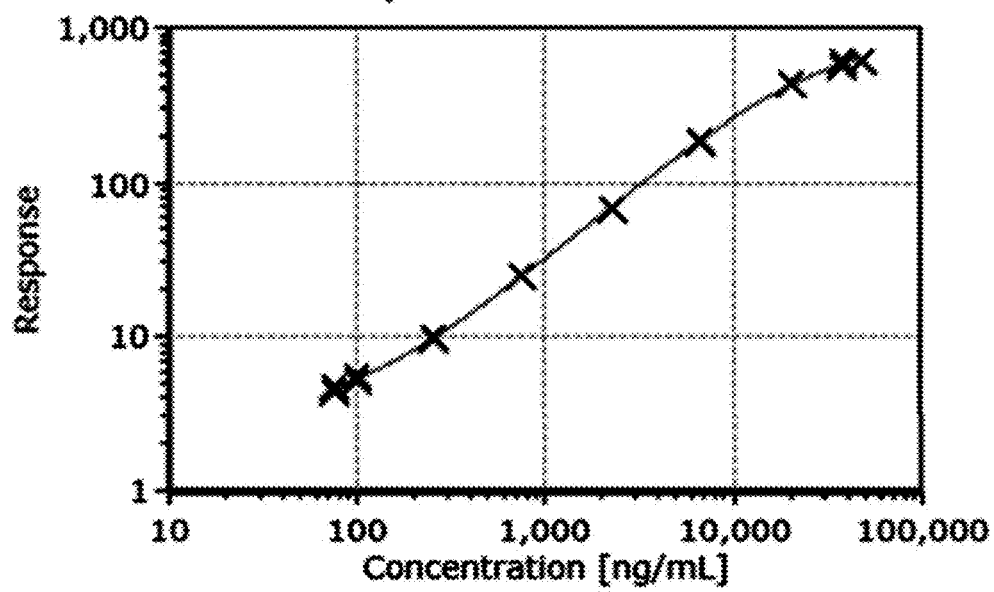

[Figure 28]

SEQ ID NO: 29 - Nucleotide sequence encoding the amino acid sequences of a human light chain signal sequence and a human κ chain constant region gcctccggactctagagccaccATGGTGCTGCAGACCC
AGGTGTTCATCTCCCTGCTGCTGTGGATCTCCGGCGCG
TACGGCGATATCGTGATGATTAAACGTACGGTGGCCGC
CCCCTCCGTGTTCATCTTCCCCCCTCCGACGAGCAGC
TGAAGTCCGGCACCGCCTCCGTGGTGTGCCTGCTGAAT
AACTTCTACCCAGAGAGGCCAAGGTGCAGTGGAAGGT
GGACAACGCCCTGCAGTCCGGGAACTCCCAGGAGAGCG
TGACCGAGCAGGACAGCAAGGACAGCACCTACAGCCTG
AGCAGCACCCTGACCCTGAGCAAAGCCGACTACGAGAA
GCACAAGGTGTACGCCTGCGAGGTGACCCACCAGGGCC
TGAGCTCCCCCGTCACCAAGAGCTTCAACAGGGGGGAG
TGTTAGgggcccgtttaaacggggaggcta Signal sequence (23-82), Light chain constant region (107-421)

[Figure 29]

SEQ ID NO: 30 - Nucleotide sequence encoding the amino acid sequence of a heavy chain of rabbit chimeric antibody 1A3 ccagcctcggactctagagccaccATGAAGCACCTGTGGTTCTTTC
TGCTGCTGGTGGCCGCTCCTAGATGGGTGCTGTCTGAAGTGAAGCTG
GTGGAATCTGGCGGCGGACTGGTTCAACCTGGCGGCTCTAGAAAGCT
GAGCTGTGCCGCCAGCGGCTTCACCTTTAGCGATTACGGCATGGTCT
GGATCCGGCAGGCTCCTGGAAGAGGCCTTGAGTGGGTCGCCTACATC
AGCTCTGGAAGCAGCGCCATCTACTACGCCGACACCGTGAAGGGCAG
ATTCACCATCAGCCGGGACAACGCCAAGAATACCCTGTTCCTGCAGA
TGAACAGCCTGCGGAGCGAGGACTCCGCCATGTACTTTGTGCCCGG
CCTCCTAGATACGACGTGTACAGCGCTTGGTTTGCCTACTGGGGCCA
GGGCACACTGGTTACAGTTTCTGCCGGACAGCCAAGGCTCCTCCG
TTTTCCACTGGCTCCCTGCTGTGGCGATACCCTAGCTCTACAGTG
ACCCTGGGCTGTCTGGTCAAGGGCTATCTGCCTGAGCCTGTGACCGT
GACCTGGAATAGCGGCACCCTGACCAACGGCGTGCGGACATTTCCTA
GCGTCAGACAGAGCAGCGGCCTGTACTCTCTGAGCAGCGTGGTGTCT
GTGACCAGCAGCTCTCAGCCAGTGACCTGCAATGTGGCCCATCCTGC
CACCAACACCAAGGTGGACAAAACCGTGGCTCCAGCACCTGTAGCA
AGCCCACATGTCCTCCAGCTGAGCTGCTCGGAGGCCCCAGCGTGTTC
ATCTTTCCACCTAAGCCTAAGGACACCCTGATGATCAGCAGAACCCC
TGAAGTGACCTGTGTGGTGGTGGACGTGTCCAGGATGATCCGAGG
TGCAGTTCACCTGGTACATCAACAACGAGCAAGTGCGGACCGCCAGA
CCTCCTCTGAGAGAGCAGCAGTTCAACAGCACCATCAGAGTGGTGTC
CACACTGCCCATCACACACCAGGATTGGCTGCGGGGCAAAGAATTCA
AGTGCAAGGTGCACAACAAGGCCCTGCCTGCTCCTATCGAGAAAACC
ATCAGCAAGGCCAGAGGCCAGCCACTGGAACCCAAGGTGTACACAAT
GGGCCCTCCAAGAGAGGAACTGAGCAGCAGATCCGTGTCTCTGACCT
GCATGATCAACGGCTTCTACCCCAGCGACATCAGCGTGGAATGGGAG
AAGAATGGCAAGGCCGAGGACAACTACAAGACAACCCCTGCCGTGCT
GGATAGCGACGGCAGCTACTTCCTGTACAACAAGCTGTCCGTGCCTA
CCAGCGAATGGCAGCGGGAGATGTGTTTACCTGCAGCGTGATGCAC
GAGGCCCTGCACAACCACTACACCCAGAAGTCCATCAGCAGGTCCCC
AGGCAAAtgagtttaaacggggaggctaact Signal sequence (26-82), Heavy chain variable region (83-448), Heavy chain constant region (449-1417)

[Figure 30]

SEQ ID NO: 31 - Nucleotide sequence encoding the amino acid sequence of a light chain of rabbit chimeric antibody 1A3 ccagcctcggactctagagccaccATGGTTCTGCAGACACAGGTGT
TCATCAGCCTGCTGCTGTGGATCTCTGGCGCCTACGGCGATATCGTG
ATGACCCAGAGCCACAAGTTCATGAGCACCAGCGTGGGCGACAGAGT
GTCCATCACCTGTAAAGCCAGCCAGGATGTGGGCTCTGCCGTCGTGT
GGTATCAGCAGAAGCCAGGCCACTCTCCTGACCTGCTGATCTACTGG
GCCAGCACCAGACATACCGGCGTGCCCGATAGATTCACAGGCTCTGG
CAGCGGCACCGACTTCACACTGACAATCGGCAACGTGCAGAGCGAGG
ACCTGGCCGATTACTTCTGCCAGCAGTACAGCAGCTACCCCGTGACA
TTTGGCGGAGGCACCAAGCTGGAAATCAAGAGGGATCCCGTGGCTCC
CTCCGTGCTGCTGTTTCCTCCAAGCAAAGAGGAACTGACCACCGGCA
CCGCCACCATTGTGTGTGTGGCCAACAAGTTCTACCCCAGCGACATC
ACCGTGACCTGGAAGGTGGACGGCACAACACAGCAGAGCGGCATCGA
GAACAGCAAGACCCTCAGAGCCCGAGGACAACACATACAGCCTGA
GCAGCACCCTGAGCCTGACAAGCGCCCAGTACAATAGCCACAGCGTG
TACACATGCGAGGTGGTGCAGGGAAGCGCCTCTCCTATCGTGCAGTC
CTTCAACAGAGGCGACTGCtgagtttaaacgggggaggctaact Signal sequence (26-85), Light chain variable region (86-406), Light chain constant region (407-724)

[Figure 31]

SEQ ID NO: 32 - Amino acid sequence of a heavy chain of the anti-GPR20 antibody

MKHLWFFLLLVAAPRWVLSEVQLVQSGAEVKKPGASVK
VSCKASGYTFTSYYISWIRQAPGQGLKYMGFINPGSGH
TNYNEKFKGRVTITADKSSTATMELSSLRSEDTAVYY
CARGAGGFLRIITKFDYWGQGTLVTVSSASTKGPSVFP
LAPSSKSTSGGTAALGCLVKDYFPEPVTVSWNSGALTS
GVHTFPAVLQSSGLYSLSSVVTVPSSSLGTQTYICNVN
HKPSNTKVDKRVEPKSCDKTHTCPPCPAPELLGGPSVF
LFPPKPKDTLMISRTPEVTCVVVDVSHEDPEVKFNWYV
DGVEVHNAKTKPREEQYNSTYRVVSVLTVLHQDWLNGK
EYKCKVSNKALPAPIEKTISKAKGQPREPQVYTLPPSR
EEMTKNQVSLTCLVKGFYPSDIAVEWESNGQPENNYKT
TPPVLDSDGSFFLYSKLTVDKSRWQQGNVFSCSVMHEA
LHNHYTQKSLSLSPGK

Signal sequence (1-19), Variable region (20-142), Constant region (143-472)

[Figure 32]

SEQ ID NO: 33 - Amino acid sequence of a light chain of the anti-GPR20 antibody

MVLQTQVFISLLLWISGAYGDTQLTQSPSSLSASVGDR
VTITCRASKSVSTYIHWYQQKPGKQPKLLIYSAGNLES
GVPSRFSGSGSGTDFTLTISSLQPEDFANYYCQQINEL
PYTFGQGTKVEIKRTVAAPSVFIFPPSDEQLKSGTASV
VCLLNNFYPREAKVQWKVDNALQSGNSQESVTEQDSKD
STYSLSSTLTLSKADYEKHKVYACEVTHQGLSSPVTKS
FNRGEC

Signal sequence (1-20), Variable region (21-129), Constant region (130-234)

[Figure 33]

SEQ ID NO: 34 - Amino acid sequence of a heavy chain of the anti-CDH6 antibody

MKHLWFFLLLVAAPRWVLSEVQLVQSGAEVKKPGASVK
VSCKASGYTFTRNFMHWVRQAPGQGLEWMGWIYPGDGE
TEYAQKFQGRVTITADTSTSTAYMELSSLRSEDTAVYY
CARGVYGGFAGGYFDFWGQGTLVTVSSASTKGPSVFPL
APSSKSTSGGTAALGCLVKDYFPEPVTVSWNSGALTSG
VHTFPAVLQSSGLYSLSSVVTVPSSSLGTQTYICNVNH
KPSNTKVDKRVEPKSCDKTHTCPPCPAPELLGGPSVFL
FPPKPKDTLMISRTPEVTCVVVDVSHEDPEVKFNWYVD
GVEVHNAKTKPREEQYNSTYRVVSVLTVLHQDWLNGKE
YKCKVSNKALPAPIEKTISKAKGQPREPQVYTLPPSRE
EMTKNQVSLTCLVKGFYPSDIAVEWESNGQPENNYKTT
PPVLDSDGSFFLYSKLTVDKSRWQQGNVFSCSVMHEAL
HNHYTQKSLSLSPGK

Signal sequence (1-19), Variable region (20-141), Constant region (142-471)

[Figure 34]

SEQ ID NO: 35 - Amino acid sequence of a light chain of the anti-CDH6 antibody

MVLQTQVFISLLLWISGAYGDIQMTQSPSSLSASVGDR
VTITCKASQNIYKNLAWYQQKPGKAPKLLIYDANTLQT
GVPSRFSGSGSGSDFTLTISSLQPEDFATYFCQQYYSG
WAFGQGTKVEIKRTVAAPSVFIFPPSDEQLKSGTASVV
CLLNNFYPREAKVQWKVDNALQSGNSQESVTEQDSKDS
TYSLSSTLTLSKADYEKHKVYACEVTHQGLSSPVTKSF
NRGEC

Signal sequence (1-20), Variable region (21-128), Constant region (129-233)

[Figure 35]
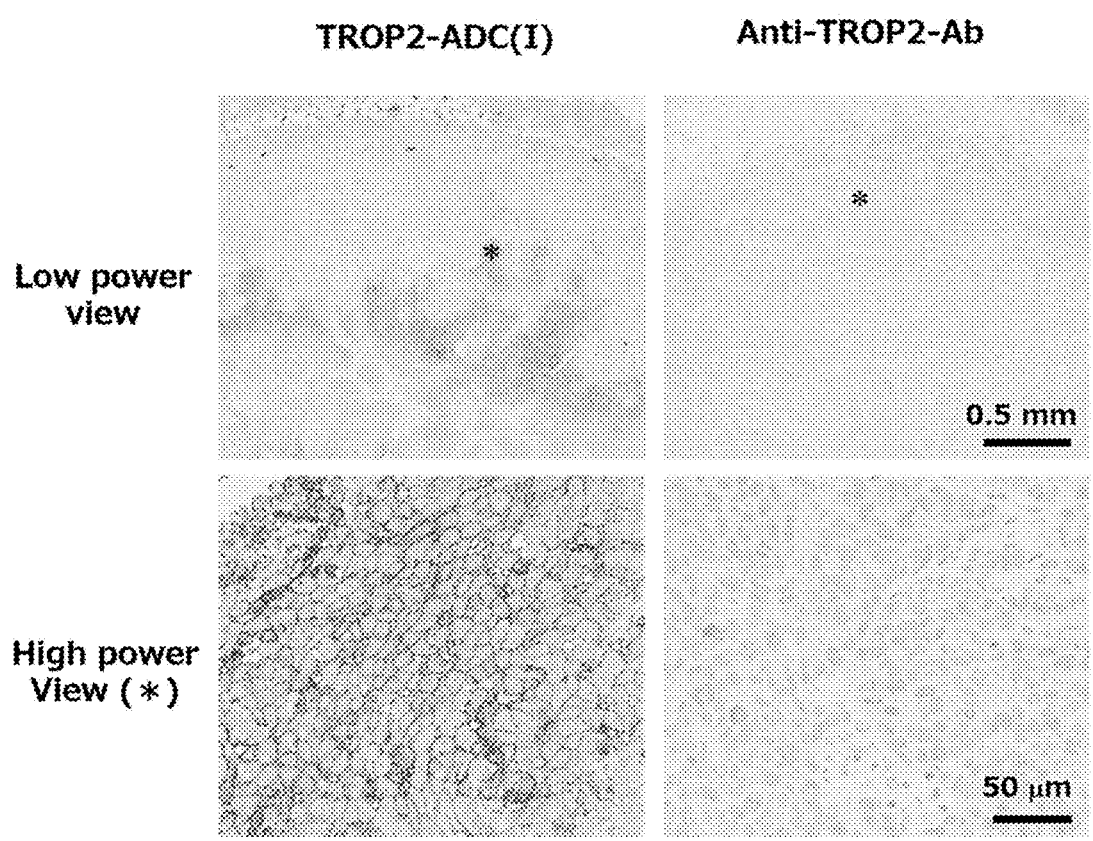

[Figure 36]
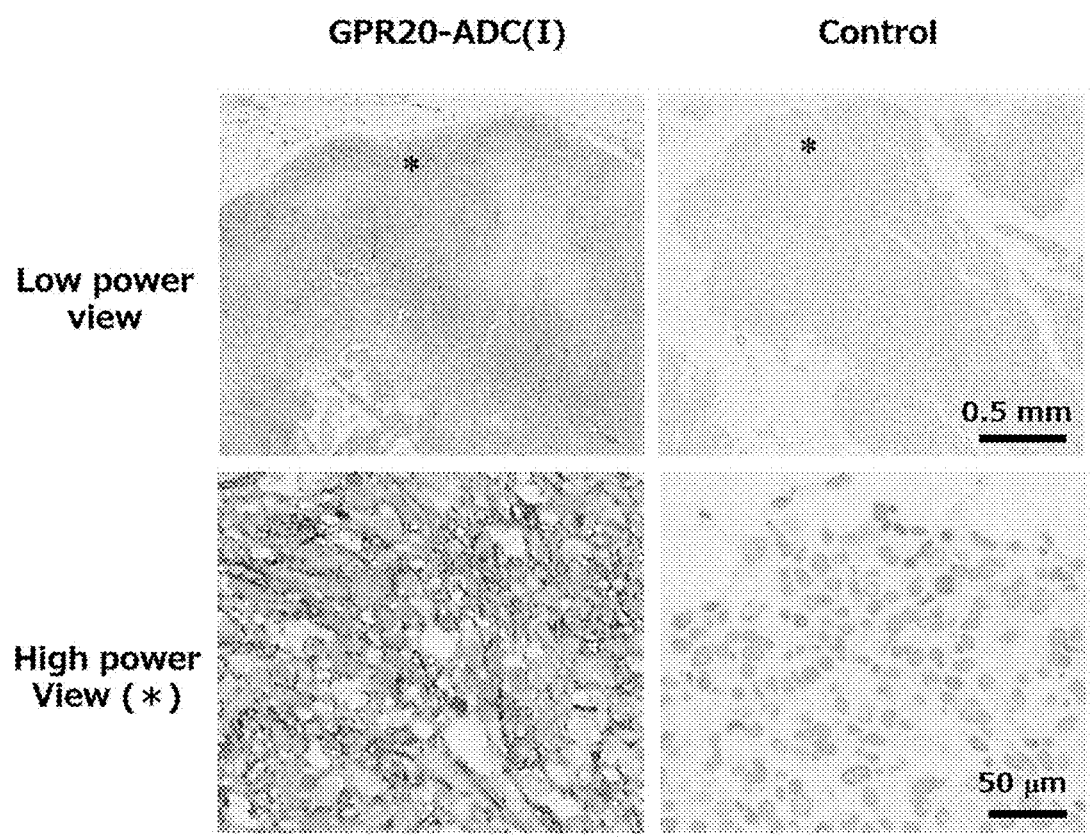

[Figure 37]
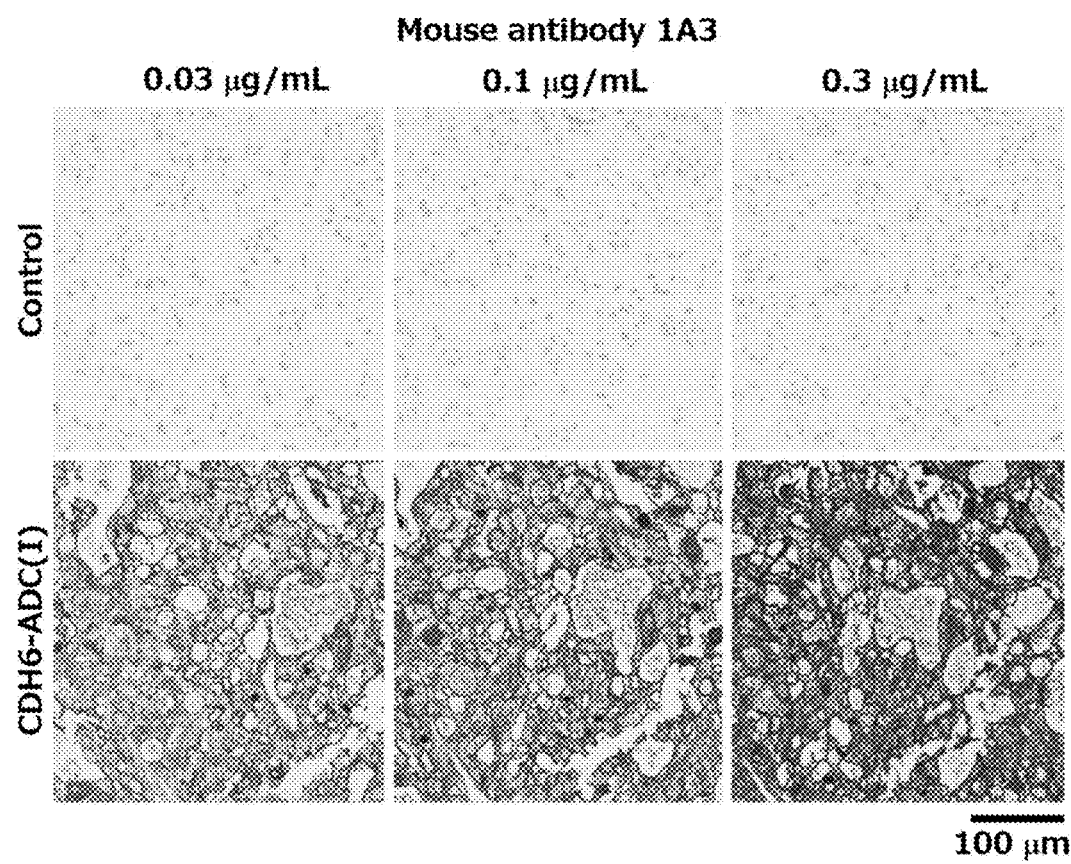

[Figure 38]
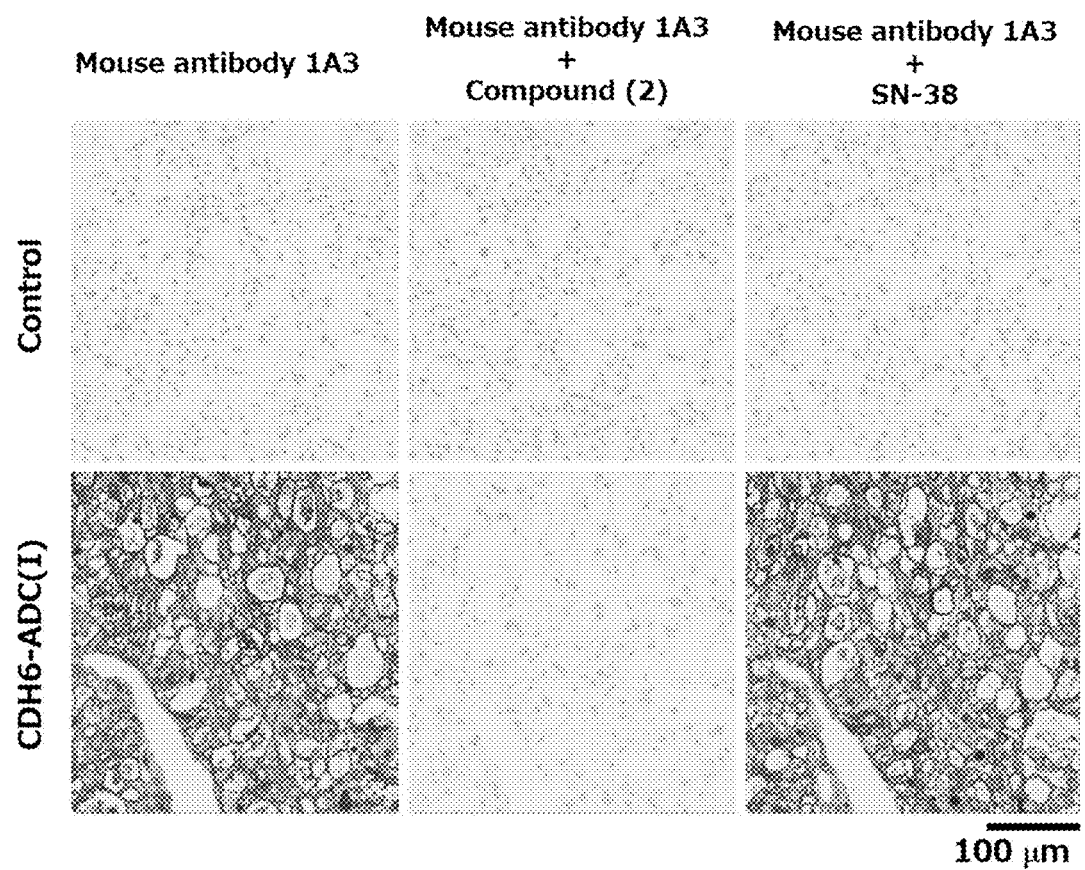

[Figure 39]
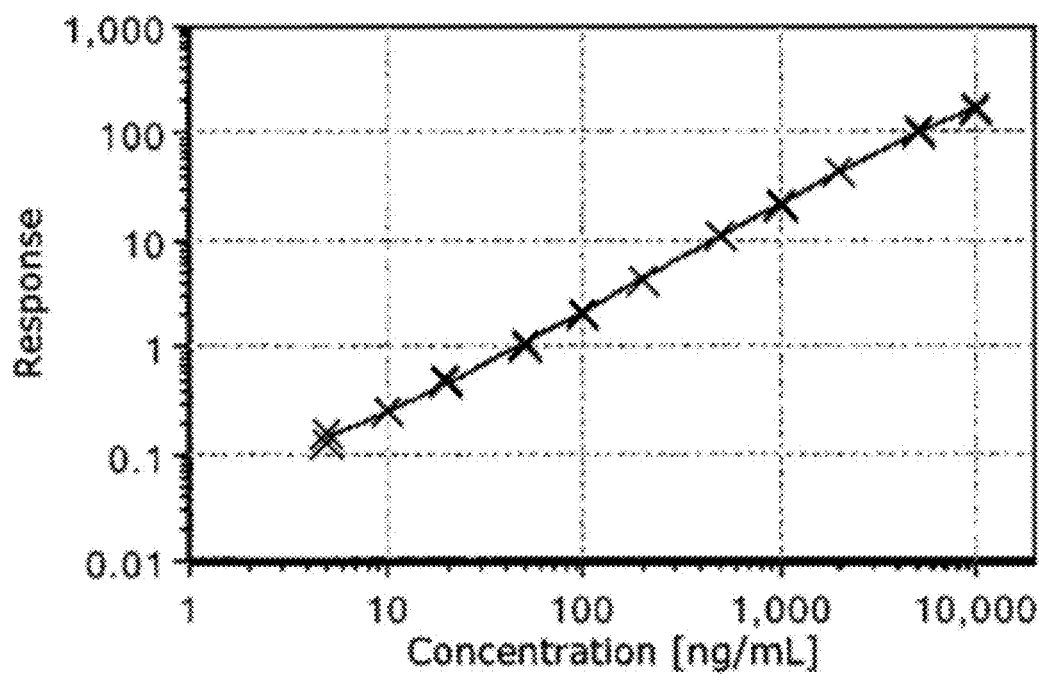

[Figure 40]
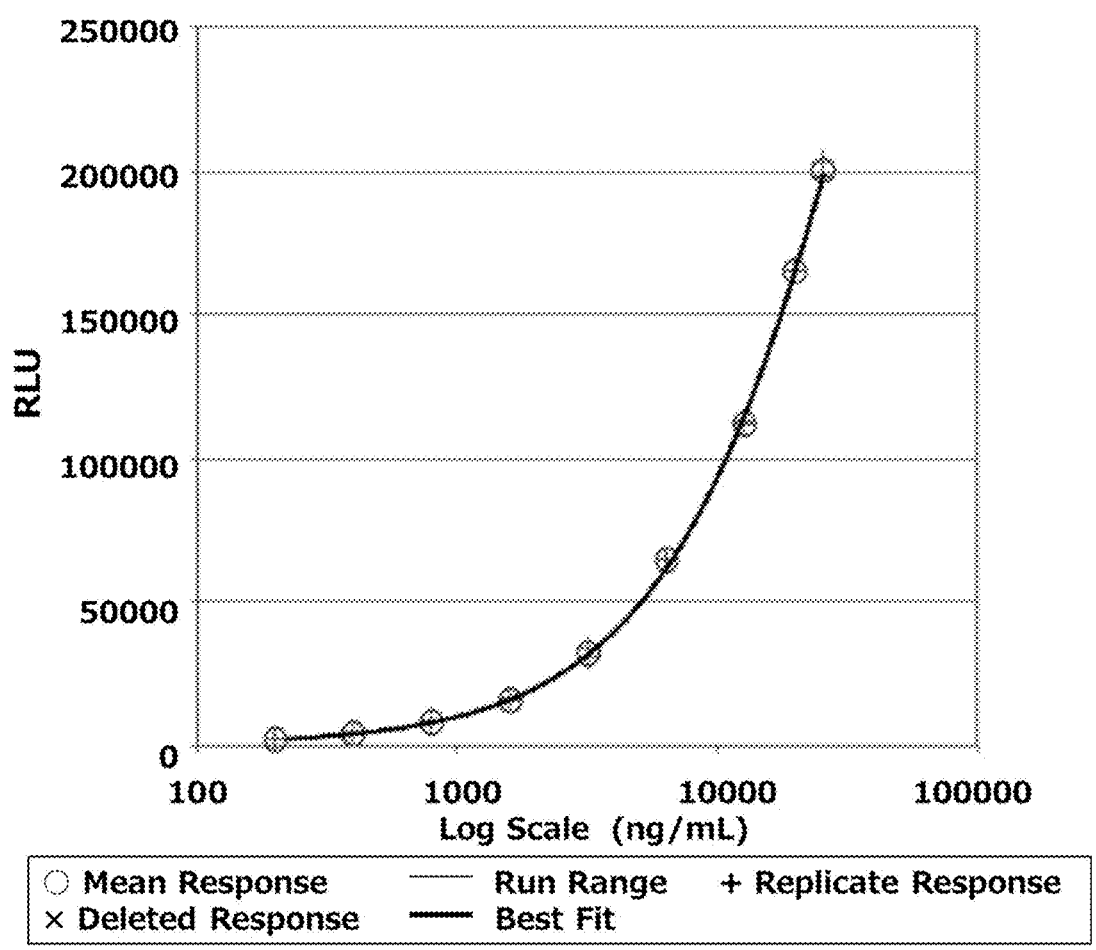

[Figure 41]
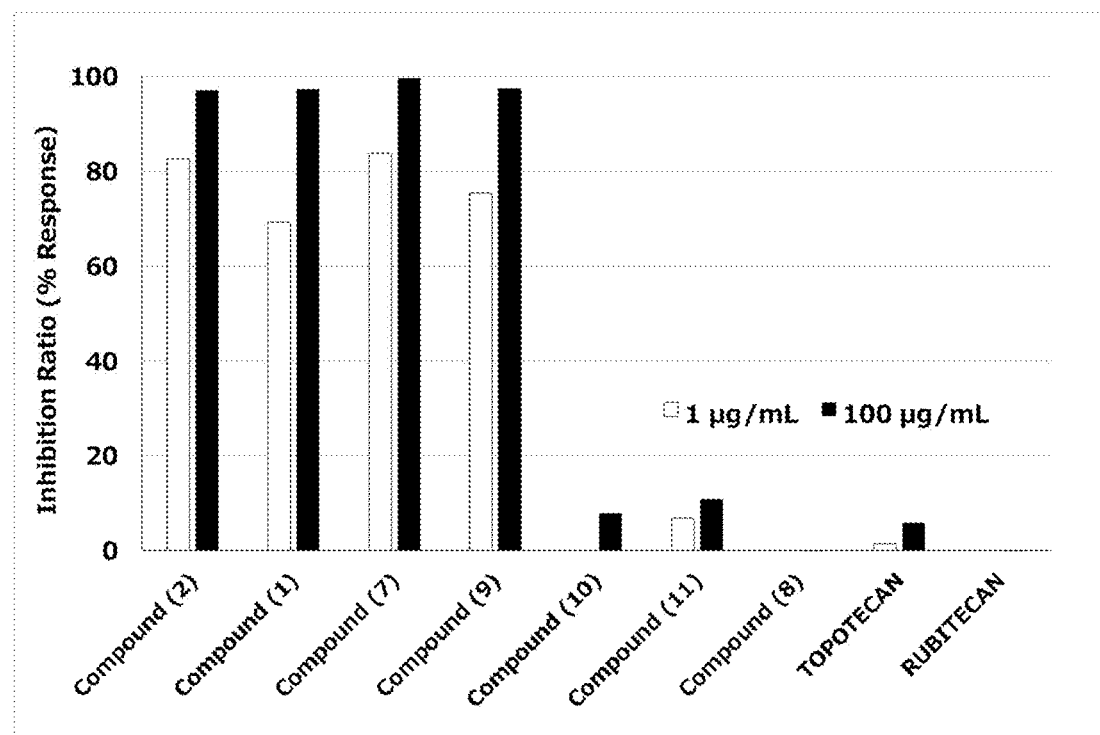

```
                          SEQUENCE LISTING

<160> NUMBER OF SEQ IDS NOS: 35

<210> SEQ ID NO 1
<211> LENGTH: 10
<212> TYPE: PRT
<213> ORGANISM: Mus musculus

<400> SEQUENCE: 1

Gly Phe Thr Phe Ser Asp Tyr Gly Met Val
1               5                   10

<210> SEQ ID NO 2
<211> LENGTH: 10
<212> TYPE: PRT
<213> ORGANISM: Mus musculus

<400> SEQUENCE: 2

Tyr Ile Ser Ser Gly Ser Ser Ala Ile Tyr
1               5                   10

<210> SEQ ID NO 3
<211> LENGTH: 13
<212> TYPE: PRT
<213> ORGANISM: Mus musculus

<400> SEQUENCE: 3

Pro Pro Arg Tyr Asp Val Tyr Ser Ala Trp Phe Ala Tyr
1               5                   10

<210> SEQ ID NO 4
<211> LENGTH: 11
<212> TYPE: PRT
<213> ORGANISM: Mus musculus

<400> SEQUENCE: 4

Lys Ala Ser Gln Asp Val Gly Ser Ala Val Val
1               5                   10

<210> SEQ ID NO 5
<211> LENGTH: 7
<212> TYPE: PRT
<213> ORGANISM: Mus musculus

<400> SEQUENCE: 5

Trp Ala Ser Thr Arg His Thr
1               5

<210> SEQ ID NO 6
<211> LENGTH: 9
<212> TYPE: PRT
<213> ORGANISM: Mus musculus

<400> SEQUENCE: 6
```

Gln Gln Tyr Ser Ser Tyr Pro Val Thr
1               5

<210> SEQ ID NO 7
<211> LENGTH: 7
<212> TYPE: PRT
<213> ORGANISM: Mus musculus

<400> SEQUENCE: 7

Gly Phe Thr Phe Ser Asp Tyr
1               5

<210> SEQ ID NO 8
<211> LENGTH: 6
<212> TYPE: PRT
<213> ORGANISM: Mus musculus

<400> SEQUENCE: 8

Ser Ser Gly Ser Ser Ala
1               5

<210> SEQ ID NO 9
<211> LENGTH: 5
<212> TYPE: PRT
<213> ORGANISM: Mus musculus

<400> SEQUENCE: 9

Asp Tyr Gly Met Val
1               5

<210> SEQ ID NO 10
<211> LENGTH: 17
<212> TYPE: PRT
<213> ORGANISM: Mus musculus

<400> SEQUENCE: 10

Tyr Ile Ser Ser Gly Ser Ser Ala Ile Tyr Tyr Ala Asp Thr Val Lys
1               5                   10                  15

Gly

<210> SEQ ID NO 11
<211> LENGTH: 8
<212> TYPE: PRT
<213> ORGANISM: Mus musculus

<400> SEQUENCE: 11

Gly Phe Thr Phe Ser Asp Tyr Gly
1               5

<210> SEQ ID NO 12
<211> LENGTH: 8
<212> TYPE: PRT
<213> ORGANISM: Mus musculus

<400> SEQUENCE: 12

Ile Ser Ser Gly Ser Ser Ala Ile
1               5

<210> SEQ ID NO 13
<211> LENGTH: 15
<212> TYPE: PRT
<213> ORGANISM: Mus musculus

<400> SEQUENCE: 13

```
Ala Arg Pro Pro Arg Tyr Asp Val Tyr Ser Ala Trp Phe Ala Tyr
1               5                   10                  15
```

<210> SEQ ID NO 14
<211> LENGTH: 6
<212> TYPE: PRT
<213> ORGANISM: Mus musculus

<400> SEQUENCE: 14

```
Gln Asp Val Gly Ser Ala
1               5
```

<210> SEQ ID NO 15
<211> LENGTH: 477
<212> TYPE: PRT
<213> ORGANISM: Mus musculus

<400> SEQUENCE: 15

```
Met Lys His Leu Trp Phe Phe Leu Leu Leu Val Ala Ala Pro Arg Trp
1               5                   10                  15

Val Leu Ser Glu Val Lys Leu Val Glu Ser Gly Gly Gly Leu Val Gln
                20                  25                  30

Pro Gly Gly Ser Arg Lys Leu Ser Cys Ala Ala Ser Gly Phe Thr Phe
            35                  40                  45

Ser Asp Tyr Gly Met Val Trp Ile Arg Gln Ala Pro Gly Arg Gly Leu
50                  55                  60

Glu Trp Val Ala Tyr Ile Ser Ser Gly Ser Ser Ala Ile Tyr Tyr Ala
65                  70                  75                  80

Asp Thr Val Lys Gly Arg Phe Thr Ile Ser Arg Asp Asn Pro Lys Asn
                85                  90                  95

Thr Leu Phe Leu Gln Met Asn Ser Leu Arg Ser Glu Asp Ser Ala Met
            100                 105                 110

Tyr Phe Cys Ala Arg Pro Pro Arg Tyr Asp Val Tyr Ser Ala Trp Phe
        115                 120                 125

Ala Tyr Trp Gly Gln Gly Thr Leu Val Thr Val Ser Ala Ala Lys Thr
    130                 135                 140

Thr Pro Pro Ser Val Tyr Pro Leu Ala Pro Gly Cys Gly Asp Thr Thr
145                 150                 155                 160

Gly Ser Ser Val Thr Ser Gly Cys Leu Val Lys Gly Tyr Phe Pro Glu
                165                 170                 175

Pro Val Thr Val Thr Trp Asn Ser Gly Ser Leu Ser Ser Ser Val His
            180                 185                 190

Thr Phe Pro Ala Leu Leu Gln Ser Gly Leu Tyr Thr Met Ser Ser Ser
        195                 200                 205

Val Thr Val Pro Ser Ser Thr Trp Pro Ser Gln Thr Val Thr Cys Ser
    210                 215                 220

Val Ala His Pro Ala Ser Ser Thr Thr Val Asp Lys Lys Leu Glu Pro
225                 230                 235                 240

Ser Gly Pro Ile Ser Thr Ile Asn Pro Cys Pro Pro Cys Lys Glu Cys
                245                 250                 255

His Lys Cys Pro Ala Pro Asn Leu Glu Gly Gly Pro Ser Val Phe Ile
            260                 265                 270

Phe Pro Pro Asn Ile Lys Asp Val Leu Met Ile Ser Leu Thr Pro Lys
        275                 280                 285

Val Thr Cys Val Val Val Asp Val Ser Glu Asp Asp Pro Asp Val Gln
    290                 295                 300
```

```
Ile Ser Trp Phe Val Asn Asn Val Glu Val His Thr Ala Gln Thr Gln
305                 310                 315                 320

Thr His Arg Glu Asp Tyr Asn Ser Thr Ile Arg Val Val Ser Thr Leu
            325                 330                 335

Pro Ile Gln His Gln Asp Trp Met Ser Gly Lys Glu Phe Lys Cys Lys
        340                 345                 350

Val Asn Asn Lys Asp Leu Pro Ser Pro Ile Glu Arg Thr Ile Ser Lys
    355                 360                 365

Ile Lys Gly Leu Val Arg Ala Pro Gln Val Tyr Thr Leu Pro Pro Pro
370                 375                 380

Ala Glu Gln Leu Ser Arg Lys Asp Val Ser Leu Thr Cys Leu Val Val
385                 390                 395                 400

Gly Phe Asn Pro Gly Asp Ile Ser Val Glu Trp Thr Ser Asn Gly His
                405                 410                 415

Thr Glu Glu Asn Tyr Lys Asp Thr Ala Pro Val Leu Asp Ser Asp Gly
            420                 425                 430

Ser Tyr Phe Ile Tyr Ser Lys Leu Asn Met Lys Thr Ser Lys Trp Glu
        435                 440                 445

Lys Thr Asp Ser Phe Ser Cys Asn Val Arg His Glu Gly Leu Lys Asn
450                 455                 460

Tyr Tyr Leu Lys Lys Thr Ile Ser Arg Ser Pro Gly Lys
465                 470                 475

<210> SEQ ID NO 16
<211> LENGTH: 234
<212> TYPE: PRT
<213> ORGANISM: Mus musculus

<400> SEQUENCE: 16

Met Val Leu Gln Thr Gln Val Phe Ile Ser Leu Leu Leu Trp Ile Ser
1               5                   10                  15

Gly Ala Tyr Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Gly Ser Ala Val Val Trp Tyr Gln Gln Lys Pro Gly His Ser Pro
    50                  55                  60

Asp Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Gly
                85                  90                  95

Asn Val Gln Ser Glu Asp Leu Ala Asp Tyr Phe Cys Gln Gln Tyr Ser
            100                 105                 110

Ser Tyr Pro Val Thr Phe Gly Gly Thr Lys Leu Glu Ile Lys Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205
```

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 17
<211> LENGTH: 504
<212> TYPE: DNA
<213> ORGANISM: Mus musculus

<400> SEQUENCE: 17
atggactcca ggctcaattt agttttcctt gtccttattt taaaaggtgt ccagtgtgag    60
gtgaagctgg tggagtctgg gggaggctta gtgcagcctg agggtcccg gaaactctcc   120 tgtgcagcct ctggattcac tttcagtgac tacggaatgg tgtggattcg acaggctcca   180
gggagggggc tggagtgggt tgcatacatt agtagtggca gtagtgccat ctactatgca   240
gacacagtga aggccgatt caccatctcc agagacaatc ccaagaacac cctgttcctg   300
caaatgaaca gtctaaggtc tgaggactcg gccatgtatt tctgtgcaag ccccccgt    360 tatgatgttt actctgcctg gtttgcttac tggggccaag ggactctggt cactgtctct   420
gcagccaaaa caacaccccc atcagtctat ccactggccc ctgggtgtgg agatacaact   480
ggttcctccg tgactctggg atgc                                          504

<210> SEQ ID NO 18
<211> LENGTH: 459
<212> TYPE: DNA
<213> ORGANISM: Mus musculus

<400> SEQUENCE: 18
atggagacac attctcaggt ctttgtatac atgttgctgt ggttgtctga tgttgaagga    60
gacattgtga tgacccagtc tcacaaattc atgtccacat ctgtaggaga cagggtcagc   120
atcacctgca aggccagtca ggatgtgggt agtgctgtag tctggtatca acagaaacct   180
gggcactctc ctgacctact gatttactgg gcatccaccc ggcacactgg agtccctgat   240
cgcttcacag gcagtggatc tgggacagat ttcacgctca ccattggcaa tgtgcagtct   300
gaagacttgg cagattattt ctgtcagcaa tatagcagct atcctgtcac gttcggaggg   360
gggaccaagc tggaaataaa acgggctgat gctgcaccaa ctgtatccat cttcccacca   420
tccagtgagc agttaacatc tggaggtgcc tcagtcgtg                          459

<210> SEQ ID NO 19
<211> LENGTH: 464
<212> TYPE: PRT
<213> ORGANISM: Artificial Sequence
<220> FEATURE:
<223> OTHER INFORMATION: Synthetic peptide

<400> SEQUENCE: 19

Met Lys His Leu Trp Phe Phe Leu Leu Leu Val Ala Ala Pro Arg Trp
1               5                   10                  15

Val Leu Ser Glu Val Lys Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Asp Tyr Gly Met Val Trp Ile Arg Gln Ala Pro Gly Arg Gly Leu
    50                  55                  60

```
Glu Trp Val Ala Tyr Ile Ser Ser Gly Ser Ser Ala Ile Tyr Tyr Ala
 65                  70                  75                  80

Asp Thr Val Lys Gly Arg Phe Thr Ile Ser Arg Asp Asn Pro Lys Asn
                 85                  90                  95

Thr Leu Phe Leu Gln Met Asn Ser Leu Arg Ser Glu Asp Ser Ala Met
            100                 105                 110

Tyr Phe Cys Ala Arg Pro Pro Arg Tyr Asp Val Tyr Ser Ala Trp Phe
        115                 120                 125

Ala Tyr Trp Gly Gln Gly Thr Leu Val Thr Val Ser Ala Gly Gln Pro
    130                 135                 140

Lys Ala Pro Ser Val Phe Pro Leu Ala Pro Cys Cys Gly Asp Thr Pro
145                 150                 155                 160

Ser Ser Thr Val Thr Leu Gly Cys Leu Val Lys Gly Tyr Leu Pro Glu
                165                 170                 175

Pro Val Thr Val Thr Trp Asn Ser Gly Thr Leu Thr Asn Gly Val Arg
            180                 185                 190

Thr Phe Pro Ser Val Arg Gln Ser Ser Gly Leu Tyr Ser Leu Ser Ser
        195                 200                 205

Val Val Ser Val Thr Ser Ser Ser Gln Pro Val Thr Cys Asn Val Ala
    210                 215                 220

His Pro Ala Thr Asn Thr Lys Val Asp Lys Thr Val Ala Pro Ser Thr
225                 230                 235                 240

Cys Ser Lys Pro Thr Cys Pro Pro Pro Glu Leu Leu Gly Gly Pro Ser
                245                 250                 255

Val Phe Ile Phe Pro Pro Lys Pro Lys Asp Thr Leu Met Ile Ser Arg
            260                 265                 270

Thr Pro Glu Val Thr Cys Val Val Val Asp Val Ser Gln Asp Asp Pro
        275                 280                 285

Glu Val Gln Phe Thr Trp Tyr Ile Asn Asn Glu Gln Val Arg Thr Ala
    290                 295                 300

Arg Pro Pro Leu Arg Glu Gln Gln Phe Asn Ser Thr Ile Arg Val Val
305                 310                 315                 320

Ser Thr Leu Pro Ile Thr His Gln Asp Trp Leu Arg Gly Lys Glu Phe
                325                 330                 335

Lys Cys Lys Val His Asn Lys Ala Leu Pro Ala Pro Ile Glu Lys Thr
            340                 345                 350

Ile Ser Lys Ala Arg Gly Gln Pro Leu Glu Pro Lys Val Tyr Thr Met
        355                 360                 365

Gly Pro Pro Arg Glu Glu Leu Ser Ser Arg Ser Val Ser Leu Thr Cys
    370                 375                 380

Met Ile Asn Gly Phe Tyr Pro Ser Asp Ile Ser Val Glu Trp Glu Lys
385                 390                 395                 400

Asn Gly Lys Ala Glu Asp Asn Tyr Lys Thr Thr Pro Ala Val Leu Asp
                405                 410                 415

Ser Asp Gly Ser Tyr Phe Leu Tyr Asn Lys Leu Ser Val Pro Thr Ser
            420                 425                 430

Glu Trp Gln Arg Gly Asp Val Phe Thr Cys Ser Val Met His Glu Ala
        435                 440                 445

Leu His Asn His Tyr Thr Gln Lys Ser Ile Ser Arg Ser Pro Gly Lys
    450                 455                 460

<210> SEQ ID NO 20
<211> LENGTH: 233
<212> TYPE: PRT
```

```
<213> ORGANISM: Artificial Sequence
<220> FEATURE:
<223> OTHER INFORMATION: Synthetic peptide

<400> SEQUENCE: 20

Met Val Leu Gln Thr Gln Val Phe Ile Ser Leu Leu Trp Ile Ser
1               5                   10                  15

Gly Ala Tyr Gly Asp Ile Val Met Thr Gln Ser His Lys Phe Met Ser
                20                  25                  30

Thr Ser Val Gly Asp Arg Val Ser Ile Thr Cys Lys Ala Ser Gln Asp
            35                  40                  45

Val Gly Ser Ala Val Val Trp Tyr Gln Gln Lys Pro Gly His Ser Pro
50                  55                  60

Asp Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Gly
                85                  90                  95

Asn Val Gln Ser Glu Asp Leu Ala Asp Tyr Phe Cys Gln Gln Tyr Ser
                100                 105                 110

Ser Tyr Pro Val Thr Phe Gly Gly Thr Lys Leu Glu Ile Lys Arg
            115                 120                 125

Asp Pro Val Ala Pro Ser Val Leu Leu Phe Pro Pro Ser Lys Glu Glu
130                 135                 140

Leu Thr Thr Gly Thr Ala Thr Ile Val Cys Val Ala Asn Lys Phe Tyr
145                 150                 155                 160

Pro Ser Asp Ile Thr Val Thr Trp Lys Val Asp Gly Thr Thr Gln Gln
                165                 170                 175

Ser Gly Ile Glu Asn Ser Lys Thr Pro Gln Ser Pro Glu Asp Asn Thr
            180                 185                 190

Tyr Ser Leu Ser Ser Thr Leu Ser Leu Thr Ala Gln Tyr Asn Ser
            195                 200                 205

His Ser Val Tyr Thr Cys Glu Val Val Gln Gly Ser Ala Ser Pro Ile
        210                 215                 220

Val Gln Ser Phe Asn Arg Gly Asp Cys
225                 230

<210> SEQ ID NO 21
<211> LENGTH: 450
<212> TYPE: PRT
<213> ORGANISM: Artificial Sequence
<220> FEATURE:
<223> OTHER INFORMATION: Heavy chain of anti-HER2 antibody

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 22
<211> LENGTH: 214
<212> TYPE: PRT
<213> ORGANISM: Artificial Sequence
<220> FEATURE:
<223> OTHER INFORMATION: Light chain of anti-HER2 antibody

<400> SEQUENCE: 22
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 447
<212> TYPE: PRT
<213> ORGANISM: Artificial Sequence
<220> FEATURE:
<223> OTHER INFORMATION: Heavy chain of anti-HER3 antibody

<400> SEQUENCE: 23

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

-continued

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 24
<211> LENGTH: 220
<212> TYPE: PRT
<213> ORGANISM: Artificial Sequence
<220> FEATURE:
<223> OTHER INFORMATION: Light chain of anti-HER3 antibody

<400> SEQUENCE: 24

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
                20                  25                  30

Ser Ser Asn Arg Asn Tyr Leu Ala Trp Tyr Gln Gln Asn Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 25
<211> LENGTH: 470
<212> TYPE: PRT
<213> ORGANISM: Artificial Sequence
<220> FEATURE:
<223> OTHER INFORMATION: Heavy chain of anti-TROP2 antibody

<400> SEQUENCE: 25

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Thr Ala Gly Met Gln Trp Val Arg Gln Ala Pro Gly Gln Gly Leu
50                  55                  60

Glu Trp Met Gly Trp Ile Asn Thr His Ser Gly Val Pro Lys Tyr Ala
65                  70                  75                  80

Glu Asp Phe Lys Gly Arg Val Thr Ile Ser Ala Asp Thr Ser Thr Ser
            85                  90                  95

Thr Ala Tyr Leu Gln Leu Ser Ser Leu Lys Ser Glu Asp Thr Ala Val
            100                 105                 110

Tyr Tyr Cys Ala Arg Ser Gly Phe Gly Ser Ser Tyr Trp Tyr Phe Asp
            115                 120                 125

Val Trp Gly Gln Gly Thr Leu Val Thr Val Ser Ser Ala Ser Thr Lys
            130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 26
<211> LENGTH: 234
<212> TYPE: PRT
<213> ORGANISM: Artificial Sequence
<220> FEATURE:
<223> OTHER INFORMATION: Light chain of anti-TROP2 antibody

<400> SEQUENCE: 26

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

```
Ser Leu Gln Pro Glu Asp Phe Ala Val Tyr Tyr Cys Gln Gln His Tyr
                100                 105                 110
Ile Thr Pro Leu Thr Phe Gly Gln Gly Thr Lys Leu Glu Ile Lys Arg
            115                 120                 125
Thr Val Ala Ala Pro Ser Val Phe Ile Phe Pro Pro Ser Asp Glu Gln
130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
210                 215                 220
Val Thr Lys Ser Phe Asn Arg Gly Glu Cys
225                 230

<210> SEQ ID NO 27
<211> LENGTH: 471
<212> TYPE: PRT
<213> ORGANISM: Artificial Sequence
<220> FEATURE:
<223> OTHER INFORMATION: Heavy chain of anti-B7-H3 antibody

<400> SEQUENCE: 27

Met Lys His Leu Trp Phe Phe Leu Leu Leu Val Ala Ala Pro Arg Trp
1               5                   10                  15
Val Leu Ser Gln Val Gln Leu Val Gln Ser Gly Ala Glu Val Lys Lys
            20                  25                  30
Pro Gly Ser Ser Val Lys Val Ser Cys Lys Ala Ser Gly Tyr Thr Phe
        35                  40                  45
Thr Asn Tyr Val Met His Trp Val Arg Gln Ala Pro Gly Gln Gly Leu
    50                  55                  60
Glu Trp Met Gly Tyr Ile Asn Pro Tyr Asn Asp Val Lys Tyr Asn
65                  70                  75                  80
Glu Lys Phe Lys Gly Arg Val Thr Ile Thr Ala Asp Glu Ser Thr Ser
                85                  90                  95
Thr Ala Tyr Met Glu Leu Ser Ser Leu Arg Ser Glu Asp Thr Ala Val
            100                 105                 110
Tyr Tyr Cys Ala Arg Trp Gly Tyr Gly Ser Pro Leu Tyr Tyr Phe
        115                 120                 125
Asp Tyr Trp Gly Gln Gly Thr Leu Val Thr Val Ser Ser Ala Ser Thr
    130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
        195                 200                 205
Val Val Thr Val Pro Ser Ser Ser Leu Gly Thr Gln Thr Tyr Ile Cys
    210                 215                 220
```

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 28
<211> LENGTH: 233
<212> TYPE: PRT
<213> ORGANISM: Artificial Sequence
<220> FEATURE:
<223> OTHER INFORMATION: Light chain of anti-B7-H3 antibody

<400> SEQUENCE: 28

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Ser Arg
        35                  40                  45

Leu Ile Tyr Met His Trp Tyr Gln Gln Lys Pro Gly Gln Ala Pro Arg
    50                  55                  60

Pro Leu Ile Tyr Ala Thr Ser Asn Leu Ala Ser Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Trp Asn Ser
            100                 105                 110

| | | | | | | | | | | | |
|---|---|---|---|---|---|---|---|---|---|---|---|
|Asn|Pro|Pro|Thr|Phe|Gly|Gln|Gly|Thr|Lys|Val|Glu|Ile|Lys|Arg|Thr|
| |115| | | | |120| | | | |125| | | | |

Val Ala Ala Pro Ser Val Phe Ile Phe Pro Pro Ser Asp Glu Gln Leu
    130             135             140

Lys Ser Gly Thr Ala Ser Val Val Cys Leu Leu Asn Asn Phe Tyr Pro
145             150             155             160

Arg Glu Ala Lys Val Gln Trp Lys Val Asp Asn Ala Leu Gln Ser Gly
            165             170             175

Asn Ser Gln Glu Ser Val Thr Glu Gln Asp Ser Lys Asp Ser Thr Tyr
            180             185             190

Ser Leu Ser Ser Thr Leu Thr Leu Ser Lys Ala Asp Tyr Glu Lys His
    195             200             205

Lys Val Tyr Ala Cys Glu Val Thr His Gln Gly Leu Ser Ser Pro Val
    210             215             220

Thr Lys Ser Phe Asn Arg Gly Glu Cys
225             230

<210> SEQ ID NO 29
<211> LENGTH: 449
<212> TYPE: DNA
<213> ORGANISM: Homo sapiens

<400> SEQUENCE: 29

```
gcctccggac tctagagcca ccatggtgct gcagacccag tgttcatct ccctgctgct     60 gtggatctcc ggcgcgtacg gcgatatcgt gatgattaaa cgtacggtgg ccgcccctc    120 cgtgttcatc ttccccccct ccgacgagca gctgaagtcc ggcaccgcct ccgtggtgtg    180
cctgctgaat aacttctacc cagagaggc caaggtgcag tggaaggtgg acaacgccct    240
gcagtccggg aactcccagg agagcgtgac cgagcaggac agcaaggaca gcacctacag    300
cctgagcagc accctgaccc tgagcaaagc cgactacgag aagcacaagg tgtacgcctg    360
cgaggtgacc caccagggcc tgagctcccc cgtcaccaag agcttcaaca ggggggagtg    420 ttagggggccc gtttaaacgg gggaggcta                                     449
```

<210> SEQ ID NO 30
<211> LENGTH: 1442
<212> TYPE: DNA
<213> ORGANISM: Artificial Sequence
<220> FEATURE:
<223> OTHER INFORMATION: Synthetic nucleotide

<400> SEQUENCE: 30

```
ccagcctccg gactctagag ccaccatgaa gcacctgtgg ttctttctgc tgctggtggc     60
cgctcctaga tgggtgctgt ctgaagtgaa gctggtggaa tctggcggcg gactggttca    120
acctggcggc tctagaaagc tgagctgtgc cgccagcggc ttcaccttta gcgattacgg    180
catggtctgg atccggcagg ctcctggaag aggccttgag tgggtcgcct acatcagctc    240
tggaagcagc gccatctact acgccgacac cgtgaagggc agattcacca tcagccggga    300
caaccccaag aatacccctgt tcctgcagat gaacagcctg cggagcgagg actccgccat    360 gtactttttgt gcccggcctc ctagatacga cgtgtacagc gcttggtttg cctactgggg    420
ccagggcaca ctggttacag tttctgccgg acagcccaag gctccctccg ttttttccact    480 ggctccctgc tgtggcgata cccctagctc tacagtgacc ctgggctgtc tggtcaaggg    540
ctatctgcct gagcctgtga ccgtgacctg gaatagcggc accctgacca acggcgtgcg    600
gacatttcct agcgtcagac agagcagcgg cctgtactct ctgagcagcg tggtgtctgt    660
```

```
gaccagcagc tctcagccag tgacctgcaa tgtggcccat cctgccacca acaccaaggt      720
ggacaaaacc gtggctccca gcacctgtag caagcccaca tgtcctccac ctgagctgct      780
cggaggcccc agcgtgttca tctttccacc taagcctaag acaccctga tgatcagcag       840 aaccctgaa gtgacctgtg tggtggtgga cgtgtcccag gatgatcccg aggtgcagtt       900
cacctggtac atcaacaacg agcaagtgcg gaccgccaga cctcctctga gagcagca       960 gttcaacagc accatcagag tggtgtccac actgccatc acacaccagg attggctgcg      1020
gggcaaagaa ttcaagtgca aggtgcacaa caaggccctg cctgctccta tcgagaaaac    1080
catcagcaag gccagaggcc agccactgga acccaaggtg tacacaatgg cccctccaag    1140
agaggaactg agcagcagat ccgtgtctct gacctgcatg atcaacggct ctaccccag      1200 cgacatcagc gtggaatggg agaagaatgg caaggccgag acaactaca agacaacccc    1260 tgccgtgctg gatagcgacg gcagctactt cctgtacaac aagctgtccg tgcctaccag    1320
cgaatggcag cggggagatg tgtttacctg cagcgtgatg cacgaggccc tgcacaacca    1380
ctacacccag aagtccatca gcaggtcccc aggcaaatga gtttaaacgg gggaggctaa    1440
ct                                                                    1442

<210> SEQ ID NO 31
<211> LENGTH: 749
<212> TYPE: DNA
<213> ORGANISM: Artificial Sequence
<220> FEATURE:
<223> OTHER INFORMATION: Synthetic nucleotide

<400> SEQUENCE: 31
ccagcctccg gactctagag ccaccatggt tctgcagaca caggtgttca tcagcctgct       60
gctgtggatc tctggcgcct acggcgatat cgtgatgacc cagagccaca gttcatgag      120 caccagcgtg ggcgacagag tgtccatcac ctgtaaagcc agccaggatg tgggctctgc    180
cgtcgtgtgg tatcagcaga agccaggcca ctctcctgac ctgctgatct actgggccag    240
caccagacat accggcgtgc ccgatagatt cacaggctct ggcagcggca ccgacttcac    300
actgacaatc ggcaacgtgc agagcgagga cctggccgat tacttctgcc agcagtacag    360
cagctacccc gtgacatttg gcggaggcac caagctggaa atcaagaggg atcccgtggc    420
tccctccgtg ctgctgtttc ctccaagcaa agaggaactg accaccggca ccgccaccat    480
tgtgtgtgtg ccaacaagt tctaccccag cgacatcacc gtgacctgga aggtggacgg    540
cacaacacag cagagcggca tcgagaacag caagacccct cagagccccg aggacaacac    600
atacagcctg agcagcaccc tgagcctgac aagcgcccag tacaatagcc acagcgtgta    660
cacatgcgag gtggtgcagg gaagcgcctc tcctatcgtg cagtccttca acagaggcga    720
ctgctgagtt taaacggggg aggctaact                                       749

<210> SEQ ID NO 32
<211> LENGTH: 472
<212> TYPE: PRT
<213> ORGANISM: Artificial Sequence
<220> FEATURE:
<223> OTHER INFORMATION: Heavy chain of anti-GPR20 antibody

<400> SEQUENCE: 32

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
```

-continued

```
                20                  25                  30
Pro Gly Ala Ser Val Lys Val Ser Cys Lys Ala Ser Gly Tyr Thr Phe
            35                  40                  45
Thr Ser Tyr Tyr Ile Ser Trp Ile Arg Gln Ala Pro Gly Gln Gly Leu
        50                  55                  60
Lys Tyr Met Gly Phe Ile Asn Pro Gly Ser Gly His Thr Asn Tyr Asn
65                  70                  75                  80
Glu Lys Phe Lys Gly Arg Val Thr Ile Thr Ala Asp Lys Ser Ser Ser
                85                  90                  95
Thr Ala Thr Met Glu Leu Ser Ser Leu Arg Ser Glu Asp Thr Ala Val
            100                 105                 110
Tyr Tyr Cys Ala Arg Gly Ala Gly Gly Phe Leu Arg Ile Ile Thr Lys
        115                 120                 125
Phe Asp Tyr Trp Gly Gln Gly Thr Leu Val Thr Val Ser Ser Ala Ser
    130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
        195                 200                 205
Ser Val Val Thr Val Pro Ser Ser Ser Leu Gly Thr Gln Thr Tyr Ile
    210                 215                 220
Cys Asn Val Asn His Lys Pro Ser Asn Thr Lys Val Asp Lys Arg Val
225                 230                 235                 240
Glu Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
        275                 280                 285
Val Asp Val Ser His Glu Asp Pro Glu Val Lys Phe Asn Trp Tyr Val
    290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
        355                 360                 365
Arg Glu Pro Gln Val Tyr Thr Leu Pro Pro Ser Arg Glu Glu Met Thr
    370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
```

-continued

```
Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 33
<211> LENGTH: 234
<212> TYPE: PRT
<213> ORGANISM: Artificial Sequence
<220> FEATURE:
<223> OTHER INFORMATION: Light chain of anti-GPR20 antibody

<400> SEQUENCE: 33

Met Val Leu Gln Thr Gln Val Phe Ile Ser Leu Leu Trp Ile Ser
1               5                   10                  15

Gly Ala Tyr Gly Asp Thr Gln Leu Thr Gln Ser Pro Ser Ser Leu Ser
            20                  25                  30

Ala Ser Val Gly Asp Arg Val Thr Ile Thr Cys Arg Ala Ser Lys Ser
        35                  40                  45

Val Ser Thr Tyr Ile His Trp Tyr Gln Gln Lys Pro Gly Lys Gln Pro
    50                  55                  60

Lys Leu Leu Ile Tyr Ser Ala Gly Asn Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Asn Tyr Tyr Cys Gln Gln Ile Asn
            100                 105                 110

Glu Leu Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 34
<211> LENGTH: 471
<212> TYPE: PRT
<213> ORGANISM: Artificial Sequence
<220> FEATURE:
<223> OTHER INFORMATION: Heavy chain of anti-CDH6 antibody

<400> SEQUENCE: 34

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
```

```
                35                  40                  45
Thr Arg Asn Phe Met His Trp Val Arg Gln Ala Pro Gly Gln Gly Leu
 50                  55                  60
Glu Trp Met Gly Trp Ile Tyr Pro Gly Asp Gly Thr Glu Tyr Ala
 65                  70                  75                  80
Gln Lys Phe Gln Gly Arg Val Thr Ile Thr Ala Asp Thr Ser Thr Ser
                 85                  90                  95
Thr Ala Tyr Met Glu Leu Ser Ser Leu Arg Ser Glu Asp Thr Ala Val
                100                 105                 110
Tyr Tyr Cys Ala Arg Gly Val Tyr Gly Gly Phe Ala Gly Tyr Phe
            115                 120                 125
Asp Phe Trp Gly Gln Gly Thr Leu Val Thr Val Ser Ser Ala Ser Thr
            130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
            210                 215                 220
Asn Val Asn His Lys Pro Ser Asn Thr Lys Val Asp Lys Arg Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
            355                 360                 365
Glu Pro Gln Val Tyr Thr Leu Pro Pro Ser Arg Glu Glu Met Thr Lys
            370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
            435                 440                 445
Cys Ser Val Met His Glu Ala Leu His Asn His Tyr Thr Gln Lys Ser
450                 455                 460
```

Leu Ser Leu Ser Pro Gly Lys
465             470

<210> SEQ ID NO 35
<211> LENGTH: 233
<212> TYPE: PRT
<213> ORGANISM: Artificial Sequence
<220> FEATURE:
<223> OTHER INFORMATION: Light chain of anti-CDH6 antibody

<400> SEQUENCE: 35

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asn
        35                  40                  45

Ile Tyr Lys Asn Leu Ala Trp Tyr Gln Gln Lys Pro Gly Lys Ala Pro
    50                  55                  60

Lys Leu Leu Ile Tyr Asp Ala Asn Thr Leu Gln Thr Gly Val Pro Ser
65                  70                  75                  80

Arg Phe Ser Gly Ser Gly Ser Gly Ser Asp Phe Thr Leu Thr Ile Ser
                85                  90                  95

Ser Leu Gln Pro Glu Asp Phe Ala Thr Tyr Phe Cys Gln Gln Tyr Tyr
            100                 105                 110

Ser Gly Trp Ala Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

PROTEIN RECOGNIZING DRUG MOIETY OF ANTIBODY-DRUG CONJUGATE

CROSS-REFERENCE TO RELATED APPLICATIONS

The present application claims priority under 37 U.S.C. § 371 to International Patent Application No. PCT/JP2019/029379, filed Jul. 26, 2019, which claims priority to and the benefit of Japanese Patent Application No. 2018-140912, filed on Jul. 27, 2018. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 122622-0131 SL.txt and is 56 kb in size.

TECHNICAL FIELD

The present invention relates to a protein that recognizes a drug moiety of an antibody-drug conjugate having a derivative of exatecan as a component; a method for quantifying the concentration in plasma of the antibody-drug conjugate in a mammal administered with the antibody-drug conjugate by using the protein; and a method for determining a tissue distribution thereof.

BACKGROUND ART

An antibody-drug conjugate (ADC) having a drug with cytotoxicity conjugated to an antibody which binds to an antigen expressed on the surface of cancer cells and is also capable of cellular internalization can deliver the drug selectively to the cancer cells, and is thus expected to cause accumulation of the drug within cancer cells and to kill the cancer cells (Non-Patent References 1 to 5).

In developing antibody-drug conjugates into pharmaceutical products, similarly to development of small molecule compounds and antibodies, a pharmacokinetic study (PK study) is indispensable. This is because information useful for planning of clinical trial design and considering effectiveness and safety in humans can be obtained by carrying out a PK study in humans based on understanding of the correlation between PK study results and pharmacological study results and safety test result in animals.

The PK study of an antibody-drug conjugate is basically carried out by quantifying the concentration in plasma of the antibody-drug conjugate administered. As the method for quantifying the concentration in plasma of an antibody-drug conjugate, ELISA method can be exemplified. For example, the concentration in plasma of an antibody-drug conjugate can be quantified through the steps of: (1) contacting an antibody-drug conjugate with a plate having an antigen immobilized thereon to form a complex, (2) contacting a protein capable of recognizing the antibody-drug conjugate and labeled with a marker with the complex to form a further complex; and then, (3) detecting the marker based on color/light produced by enzymatic reactions.

However, if a protein that recognizes an antibody moiety of an antibody-drug conjugate is used, plasma-concentration including not only the concentration of antibody-drug conjugate retaining the drug but also the concentration of antibody-drug conjugate from which the drug is released (more specifically, substantially the antibody moiety, alone) is quantified by calculation, and a determination cannot be accurately made.

A method for quantifying the concentration in plasma of an antibody-drug conjugate by ELISA method using a protein that recognizes a drug moiety of an antibody-drug conjugate, is known (Non Patent References 6 to 11).

As one of antibody-drug conjugates, an antibody-drug conjugate having an antibody and a derivative of exatecan, which is a topoisomerase I inhibitor, as its components, is known (Patent References 1 to 7, Non Patent References 12 to 15). Since these antibody-drug conjugates exert a particularly superior antitumor effect and have safety, they are currently under clinical studies.

A method for quantifying the concentration in plasma of an antibody-drug conjugate having a derivative of exatecan as a component while retaining a drug, has not yet been known.

CITATION LIST

Patent Literature

[Patent Reference 1] International Publication No. WO 2014/057687
[Patent Reference 2] International Publication No. WO 2014/061277
[Patent Reference 3] International Publication No. WO 2015/098099
[Patent Reference 4] International Publication No. WO 2015/115091
[Patent Reference 5] International Publication No. WO 2015/146132
[Patent Reference 6] International Publication No. WO 2015/155976
[Patent Reference 7] International Publication No. WO 2015/155998

Non Patent Literature

[Non Patent Reference 1] Ducry, L., et al., Bioconjugate Chem. (2010) 21, 5-13.
[Non Patent Reference 2] Alley, S. C., et al., Current Opinion in Chemical Biology (2010) 14, 529-537.
[Non Patent Reference 3] Damle N. K. Expert Opin. Biol. Ther. (2004) 4, 1445-1452.
[Non Patent Reference 4] Senter P. D., et al., Nature Biotechnology (2012) 30, 631-637.
[Non Patent Reference 5] Howard A. et al., J Clin Oncol 29: 398-405.
[Non Patent Reference 6] Xie H. et al., J Pharmacol Exp Ther. (2004) 308 (3), 1073-1082.
[Non Patent Reference 7] Sanderson RJ. et al., Clinical Cancer Research (2005) Vol. 11, 843-852.
[Non Patent Reference 8] Stephan JP. et al., Bioconjugate Chem. 2008, 19, 1673-1683.
[Non Patent Reference 9] Stephan JP. et al., Bioanalysis (2011) 3 (6), 677-700.
[Non Patent Reference 10] Kaur S. et al., Bioanalysis (2013) 5 (2), 201-226.
[Non Patent Reference 11] Dere R. et al., Bioanalysis (2013) 5 (9), 1025-1040.
[Non Patent Reference 12] Ogitani Y. et al., Clinical Cancer Research (2016) 22 (20), 5097-5108.
[Non Patent Reference 13] Ogitani Y. et al., Cancer Science (2016) 107, 1039-1046.

[Non Patent Reference 14] Doi T, et al., Lancet Oncol 2017; 18: 1512-22.

[Non Patent Reference 15] Takegawa N, et al., Int. J. Cancer: 141, 1682-1689 (2017).

SUMMARY OF INVENTION

Technical Problem

An object of the present invention is to provide a protein that recognizes a drug moiety of an antibody-drug conjugate having a derivative of exatecan as a component; a method for quantifying the concentration in plasma of the antibody-drug conjugate in a mammal administered with the antibody-drug conjugate by using the protein; and a method for determining a tissue distribution thereof.

Solution to Problem

As a result of diligent studies in order to solve the above problems, the present inventors have found that a protein obtained by specific immunoscreening specifically recognizes a drug moiety of an antibody-drug conjugate having a derivative of exatecan as a component. Further, they established a method for quantifying the concentration in plasma of the antibody-drug conjugate in a mammal administered with the antibody-drug conjugate by using the protein; and a method for determining a tissue distribution thereof.

Thus, the present invention provides the following [1] to [51].

[1] A protein that recognizes a drug moiety of an antibody-drug conjugate in which a drug represented by the following formula:

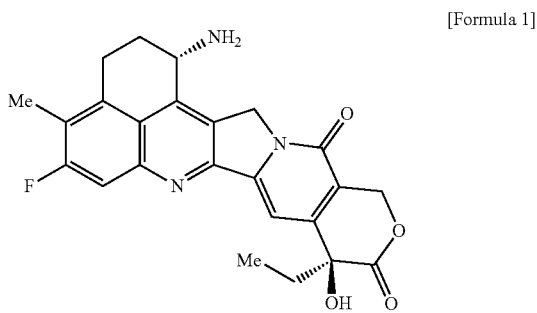 [SMILES: CC[C@@]1(O)C(=O)OCc2c1cc1n(c2=O)Cc2c-1nc1cc(F)c(C)c3c1c2[C@@H](N)CC3]

[Formula 1]

is conjugated to an antibody via a linker.

[2] The protein according to [1], wherein a drug-linker in the antibody-drug conjugate is represented by the following formula:

[Formula 2]

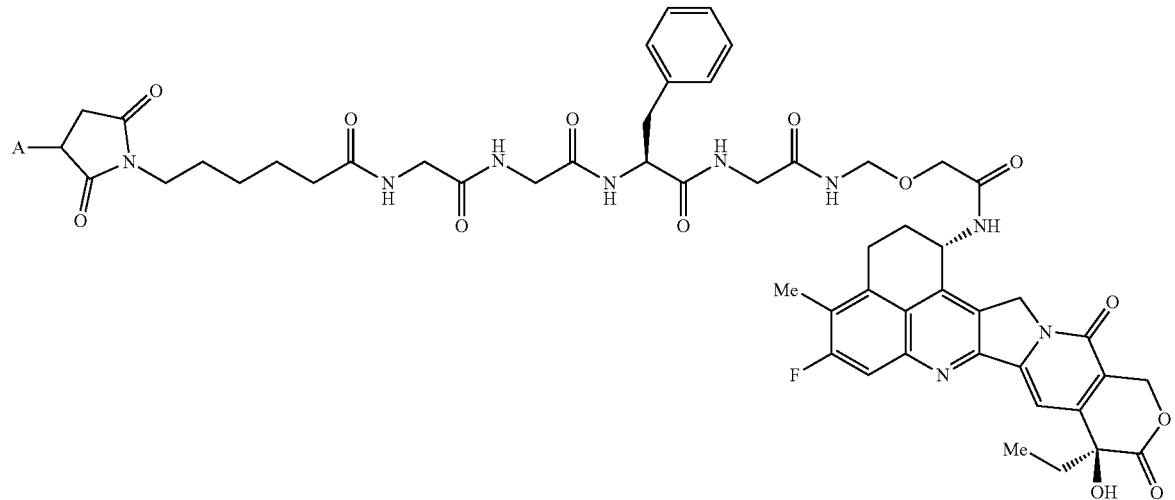

wherein A represents a connecting position to the antibody, and the drug-linker is conjugated to the antibody via a thioether bond.

[3] The protein according to [1], wherein the drug-linker in the antibody-drug conjugate is represented by the following formula:

[Formula 3]

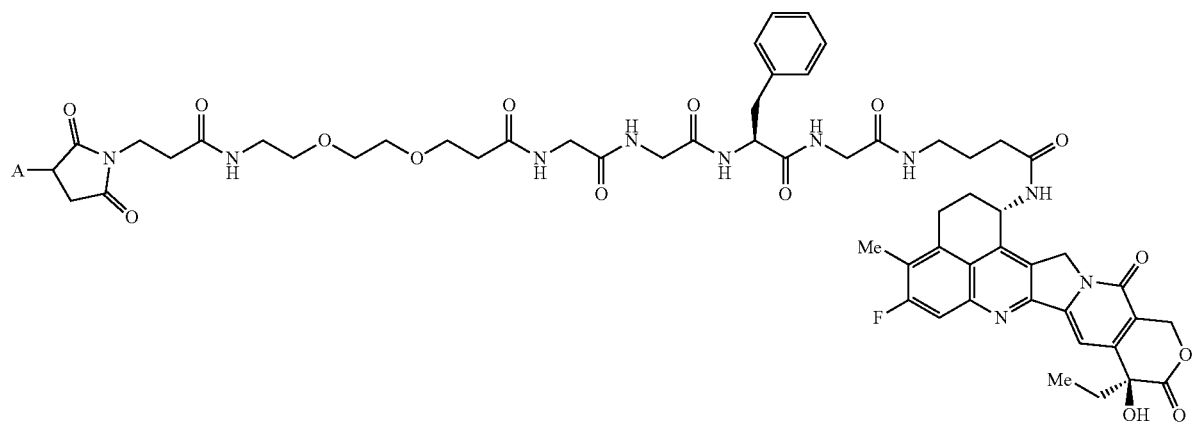

wherein A represents a connecting position to the antibody, and the drug-linker is conjugated to the antibody via a thioether bond.

[4] The protein according to [1], wherein the drug-linker in the antibody-drug conjugate is represented by the following formula:

[Formula 4]

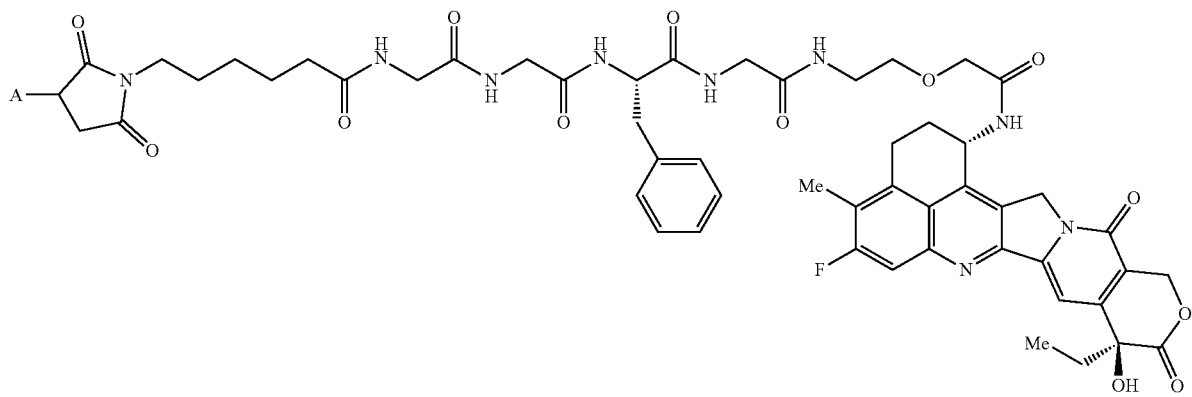

wherein A represents a connecting position to the antibody, and the drug-linker is conjugated to the antibody via a thioether bond.

[5] The protein according to [1], wherein the antibody-drug conjugate is represented by the following formula:

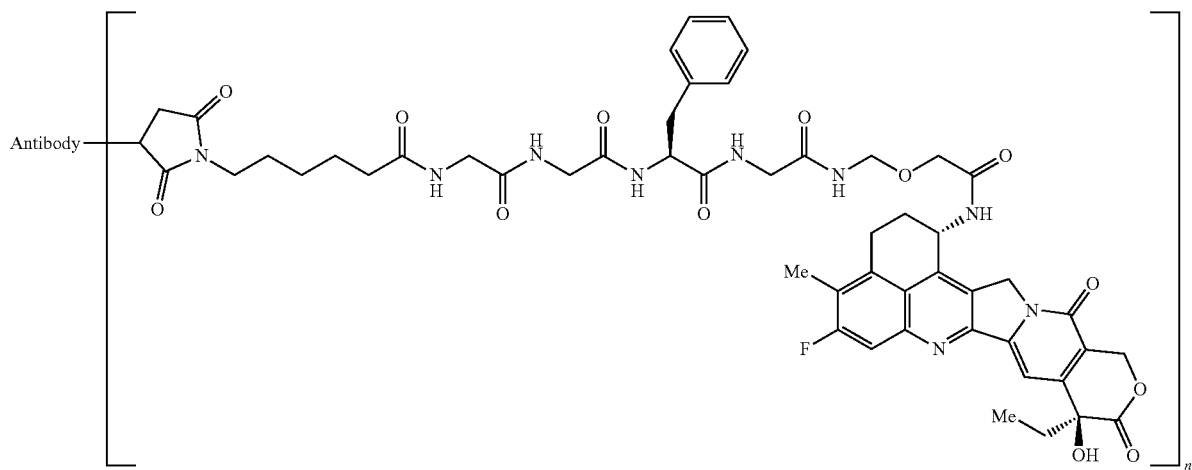

wherein the drug-linker is conjugated to the antibody via a thioether bond and n represents the average number of units of the drug-linker conjugated per antibody molecule.

[6] The protein according to [1], wherein the antibody-drug conjugate is represented by the following formula:

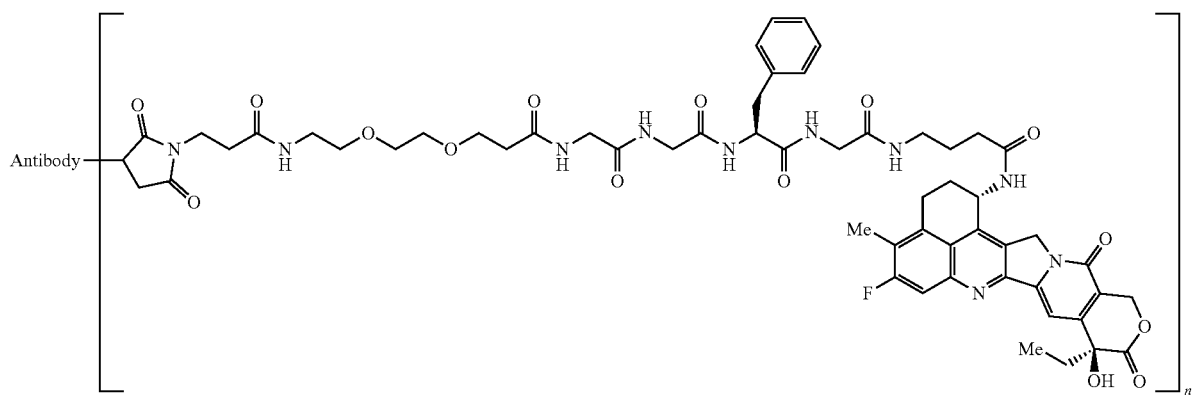

wherein the drug-linker is conjugated to the antibody via a thioether bond and n represents the average number of units of the drug-linker conjugated per antibody molecule.

[7] The protein according to [1], wherein the antibody-drug conjugate is represented by the following formula:

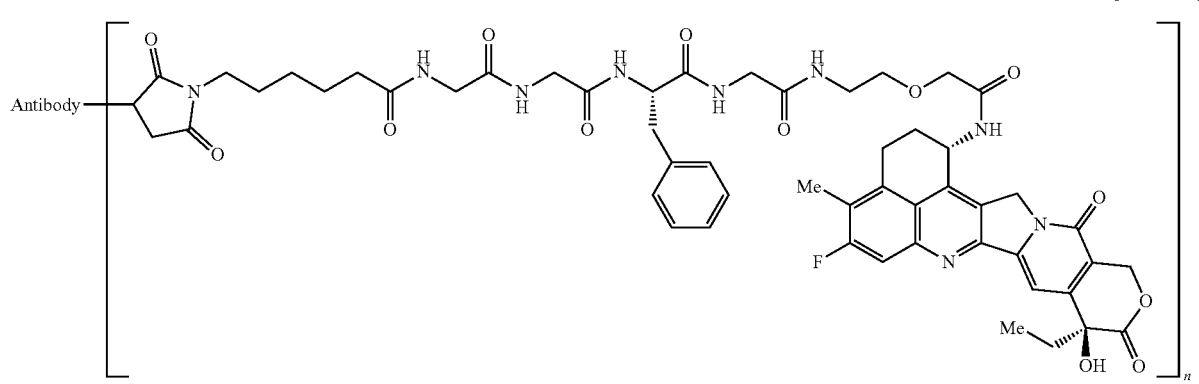

[Formula 7]

wherein the drug-linker is conjugated to the antibody via a thioether bond and n represents the average number of units of the drug-linker conjugated per antibody molecule.

[8] The protein according to any one of [1] to [7], wherein the average number of units of the drug-linker conjugated per antibody molecule in the antibody-drug conjugate is in the range of from 2 to 8.

[9] The protein according to any one of [1] to [8], wherein the antibody in the antibody-drug conjugate is an anti-HER2 antibody, an anti-HER3 antibody, an anti-TROP2 antibody, an anti-B7-H3 antibody, an anti-GPR20 antibody or an anti-CDH6 antibody.

[10] The protein according to any one of [1] to [9], wherein the recognition property of the protein to the antibody-drug conjugate is substantially independent of any difference in the average number of units of the drug-linker conjugated per antibody molecule in the antibody-drug conjugate.

[11] A protein that recognizes a drug represented by the following formula:

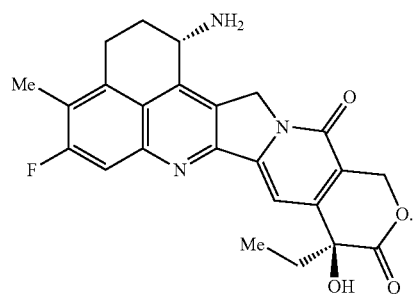

[Formula 8]

[12] A protein that recognizes a drug represented by the following formula:

[13] A protein that recognizes a drug represented by the following formula:

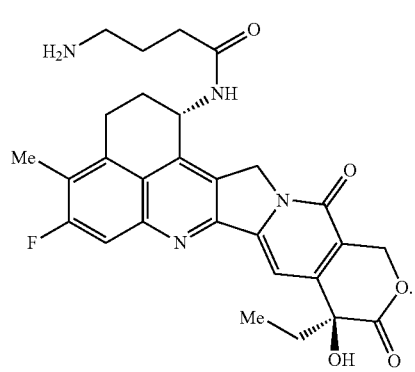

[Formula 9]

[Formula 10]

[14] A protein that recognizes a drug represented by the following formula:

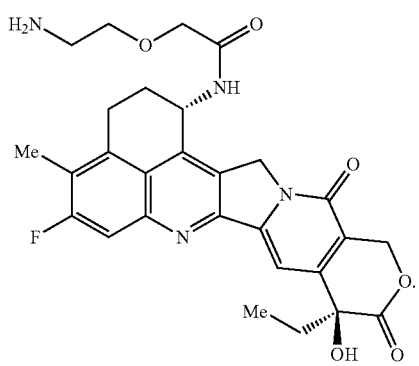

[Formula 11]

[15] The protein according to any one of [1] to [14], wherein the protein is an antibody.
[16] The protein according to [15], wherein the protein is
a) an antibody consisting of a heavy chain comprising CDRH1 consisting of an amino acid sequence represented by SEQ ID NO: 1, CDRH2 consisting of an amino acid sequence represented by SEQ ID NO: 2, and CDRH3 consisting of an amino acid sequence represented by SEQ ID NO: 3; and a light chain comprising CDRL1 consisting of an amino acid sequence represented by SEQ ID NO: 4, CDRL2 consisting of an amino acid sequence represented by SEQ ID NO: 5, and CDRL3 consisting of an amino acid sequence represented by SEQ ID NO: 6,
b) an antibody consisting of a heavy chain comprising CDRH1 consisting of an amino acid sequence represented by SEQ ID NO: 7, CDRH2 consisting of an amino acid sequence represented by SEQ ID NO: 8, and CDRH3 consisting of an amino acid sequence represented by SEQ ID NO: 3; and a light chain comprising CDRL1 consisting of an amino acid sequence represented by SEQ ID NO: 4, CDRL2 consisting of an amino acid sequence represented by SEQ ID NO: 5, and CDRL3 consisting of an amino acid sequence represented by SEQ ID NO: 6,
c) an antibody consisting of a heavy chain comprising CDRH1 consisting of an amino acid sequence represented by SEQ ID NO: 9, CDRH2 consisting of an amino acid sequence represented by SEQ ID NO: 10, and CDRH3 consisting of an amino acid sequence represented by SEQ ID NO: 3; and a light chain comprising CDRL1 consisting of an amino acid sequence represented by SEQ ID NO: 4, CDRL2 consisting of an amino acid sequence represented by SEQ ID NO: 5, and CDRL3 consisting of an amino acid sequence represented by SEQ ID NO: 6, or
d) an antibody consisting of a heavy chain comprising CDRH1 consisting of an amino acid sequence represented by SEQ ID NO: 11, CDRH2 consisting of an amino acid sequence represented by SEQ ID NO: 12, and CDRH3 consisting of an amino acid sequence represented by SEQ ID NO: 13; and a light chain comprising CDRL1 consisting of an amino acid sequence represented by SEQ ID NO: 14, CDRL2 consisting of a tripeptide represented by WAS, and CDRL3 consisting of an amino acid sequence represented by SEQ ID NO: 6.
[17] The protein according to [16], wherein the protein is an antibody consisting of a heavy chain comprising a heavy chain variable region consisting of an amino acid sequence consisting of amino acid residues 20 to 141 of SEQ ID NO: 15, and a light chain comprising a light chain variable region consisting of an amino acid sequence consisting of amino acid residues 21 to 127 of SEQ ID NO: 16.
[18] The protein according to [17], wherein the protein is a mouse antibody.
[19] The protein according to [17], wherein the protein is an antibody consisting of a heavy chain consisting of an amino acid sequence consisting of amino acid residues 20 to 477 of SEQ ID NO: 15, and a light chain consisting of an amino acid sequence consisting of amino acid residues 21 to 234 of SEQ ID NO: 16.
[20] The protein according to [17], wherein the protein is a chimeric antibody.
[21] The protein according to [17], wherein the protein is a rabbit chimeric antibody.
[22] The protein according to [17], wherein the protein is an antibody consisting of a heavy chain consisting of an amino acid sequence consisting of amino acid residues 20 to 464 of SEQ ID NO: 19, and a light chain consisting of an amino acid sequence consisting of amino acid residues 21 to 233 of SEQ ID NO: 20.
[23] The protein according to [15], wherein the protein is an antibody in which a lysine residue at the carboxyl terminus of the heavy chain of the antibody according to [19] or [22] is deleted.
[24] The protein according to [15], wherein the protein is an antibody consisting of an amino acid sequence having at least 95% identity with the amino acid sequence of the antibody according to [19] or [22].
[25] The protein according to [15], wherein the protein is an antibody consisting of an amino acid sequence having at least 99% identity with the amino acid sequence of the antibody according to [19] or [22].
[26] The protein according to [15], wherein the protein is an antibody that competes with the antibody according to [19] or [22] for the recognition property to the drug.
[27] The protein according to any one of [1] to [14], wherein the protein is an antigen binding fragment of the antibody according to any one of [15] to [26].
[28] The protein according to [27], wherein the antigen binding fragment of the antibody is Fab, F(ab')2, Fab' or Fv.
[29] A method for quantifying the concentration in plasma of an antibody-drug conjugate in a mammal to which the antibody-drug conjugate has been administered, by using the protein according to any one of [1] to [28].
[30] The method according to [29], comprising the steps of: (1) contacting an antibody-drug conjugate in plasma with a plate having a target antigen for the antibody-drug conjugate immobilized thereon to form a complex; (2) contacting the protein according to any one of [1] to [28] labeled with a marker with the complex to form a further complex; and then (3) detecting the marker.
[31] The method according to [29], comprising the steps of: (1) contacting an antibody-drug conjugate in plasma with a plate having a protein according to any one of [1] to [28] immobilized thereon to form a complex; (2) contacting a second protein that is capable of recognizing an antibody moiety of the antibody-drug conjugate and is labeled with a marker with the complex to form a further complex; and then (3) detecting the marker.
[32] A method for quantifying the concentration in plasma of a drug released from an antibody-drug conjugate in a mammal to which the antibody-drug conjugate has been administered, by using the protein according to any one of [1] to [28].

[33] The method according to [32], comprising the steps of: (1) contacting a drug released from the antibody-drug conjugate in plasma with a plate having the protein according to any one of [1] to [28] immobilized thereon, in the presence of a competitive drug labeled with a marker, to form a complex; and (2) detecting the marker.

[34] A method for identifying a tissue distribution of an antibody-drug conjugate and/or a drug released from the antibody-drug conjugate in a mammal to which the antibody-drug conjugate has been administered, using a protein according to any one of [1] to [28].

[35] The method according to [34], comprising the steps of: (1) contacting an antibody-drug conjugate and/or a drug released from the antibody-drug conjugate in a tissue with a protein according to any one of [1] to [28] to form a complex, (2) contacting a second protein that is capable of recognizing the protein according to any one of [1] to [28] and is labeled with a marker with the complex to form a further complex, and then (3) detecting the marker.

[36] The method according to [34], comprising the steps of: (1) contacting an antibody-drug conjugate and/or a drug released from the antibody-drug conjugate in a tissue with the protein according to any one of [1] to [28] labeled with a marker to form a complex; and then (2) detecting the marker.

[37] The method according to [30], [31], [33], [35] or [36], wherein the marker is a chromogenic reagent, and the detection of the marker is performed by sensing a color of the marker.

[38] The method according to [30], [31], [33], [35] or [36], wherein the marker is an enzyme, and the detection of the marker is performed by sensing luminescence or color development caused by a reaction between a substrate and the enzyme.

[39] The method according to [30], [31], [33], [35] or [36], wherein the marker is a luminescent substance, and the detection of the marker is performed by sensing the luminescence of the marker based on an electrochemical reaction.

[40] A polynucleotide encoding the protein according to any one of [1] to [28].

[41] A vector comprising the polynucleotide according to [40].

[42] A transformed host cell comprising the polynucleotide according to [40].

[43] A transformed host cell comprising the vector according to [41].

[44] A method for producing the protein according to any one of [1] to [28], comprising the steps of: culturing the host cell according to [42] or [43]; and then purifying a protein from a cultured product obtained in the culturing step.

[45] A composition comprising the protein according to any one of [1] to [28].

[46] A kit comprising the protein according to any one of [1] to [28] or the composition according to [45].

[47] The kit according to [46] for quantifying the concentration in plasma of an antibody-drug conjugate and/or a drug released from the antibody-drug conjugate in a mammal to which the antibody-drug conjugate has been administered.

[48] The kit according to [46] for identifying the tissue distribution of an antibody-drug conjugate and/or a drug released from the antibody-drug conjugate in a mammal to which the antibody-drug conjugate has been administered.

[49] An antibody comprising a heavy chain comprising a heavy chain variable region consisting of an amino acid sequence consisting of amino acid residues 20 to 141 of SEQ ID NO: 15, and a light chain comprising a light chain variable region consisting of an amino acid sequence consisting of amino acid residues 21 to 127 of SEQ ID NO: 16.

[50] The antibody according to [49], comprising a heavy chain consisting of an amino acid sequence consisting of amino acid residues 20 to 477 of SEQ ID NO: 15, and a light chain consisting of an amino acid sequence consisting of amino acid residues 21 to 234 of SEQ ID NO: 16.

[51] The antibody according to [49], comprising a heavy chain consisting of an amino acid sequence consisting of amino acid residues 20 to 464 of SEQ ID NO: 19, and a light chain consisting of an amino acid sequence consisting of amino acid residues 21 to 233 of SEQ ID NO: 20.

Advantageous Effects of Invention

The present invention provided a protein that recognizes a drug moiety of an antibody-drug conjugate having a derivative of exatecan as a component; a method for quantifying the concentration in plasma of the antibody-drug conjugate in a mammal administered with the antibody-drug conjugate, by using the protein; and a method for determining a tissue distribution thereof.

BRIEF DESCRIPTION OF DRAWINGS

FIG. 1 shows an amino acid sequence (SEQ ID NO: 15) of a heavy chain of mouse antibody 1A3.

FIG. 2 shows an amino acid sequence (SEQ ID NO: 16) of a light chain of mouse antibody 1A3.

FIG. 3 shows a nucleotide sequence (SEQ ID NO: 17) encoding the amino acid sequence of a heavy chain variable region of mouse antibody 1A3.

FIG. 4 shows a nucleotide sequence (SEQ ID NO: 18) encoding the amino acid sequence of a light chain variable region of mouse antibody 1A3.

FIG. 5 shows an amino acid sequence (SEQ ID NO: 19) of a heavy chain of rabbit chimeric antibody 1A3.

FIG. 6 shows an amino acid sequence (SEQ ID NO: 20) of a light chain of rabbit chimeric antibody 1A3.

FIG. 7 shows an amino acid sequence (SEQ ID NO: 21) of a heavy chain of an anti-HER2 antibody.

FIG. 8 shows an amino acid sequence (SEQ ID NO: 22) of a light chain of an anti-HER2 antibody.

FIG. 9 shows an amino acid sequence (SEQ ID NO: 23) of a heavy chain of an anti-HER3 antibody.

FIG. 10 shows an amino acid sequence (SEQ ID NO: 24) of a light chain of an anti-HER3 antibody.

FIG. 11 shows an amino acid sequence (SEQ ID NO: 25) of a heavy chain of an anti-TROP2 antibody.

FIG. 12 shows an amino acid sequence (SEQ ID NO: 26) of a light chain of an anti-TROP2 antibody.

FIG. 13 shows an amino acid sequence (SEQ ID NO: 27) of a heavy chain of an anti-B7-H3 antibody.

FIG. 14 shows an amino acid sequence (SEQ ID NO: 28) of a light chain of an anti-B7-H3 antibody.

FIG. 15 shows calibration curves of HER2-ADC (I) (DAR8) and HER2-ADC (I) (DAR4) when mouse antibody 1A3 was used as a capture reagent.

FIG. 16 shows calibration curves of HER2-ADC (I) (DAR8) and HER2-ADC (I) (DAR4) when mouse antibody 8B2 was used as a capture reagent.

FIG. 17 shows calibration curves of HER2-ADC (I) (DAR8) and HER2-ADC (I) (DAR4) when mouse antibody 11B1 was used as a capture reagent.

FIG. 18 shows calibration curves of HER2-ADC (I) (DAR8) and HER2-ADC (I) (DAR4) when mouse antibody 1A3 was used as a detection reagent.

FIG. 19 shows calibration curves of HER2-ADC (I) (DAR8) and HER2-ADC (I) (DAR4) when mouse antibody 8B2 was used as a detection reagent.

FIG. 20 shows calibration curves of HER2-ADC (I) (DAR8) and HER2-ADC (I) (DAR4) when mouse antibody 11B1 was used as a detection reagent.

FIG. 21 shows calibration curves of B7-H3-ADC(I) (DAR8) and B7-H3-ADC(I) (DAR4) when mouse antibody 1A3 was used as a detection reagent.

FIG. 22 shows calibration curves of B7-H3-ADC(I) (DAR8) and B7-H3-ADC(I) (DAR4) when mouse antibody 8B2 was used as a detection reagent.

FIG. 23 shows calibration curves of B7-H3-ADC(I) (DAR8) and B7-H3-ADC(I) (DAR4) when mouse antibody 11B1 was used as a detection reagent.

FIG. 24 shows a calibration curve for quantifying the concentration in plasma of HER2-ADC (I) in a mouse.

FIG. 25 shows a calibration curve for quantifying the concentration in plasma of HER3-ADC (I) in a monkey.

FIG. 26 shows a calibration curve for quantifying the concentration in plasma of TROP2-ADC (I) in a monkey.

FIG. 27 shows a calibration curve for quantifying the concentration in plasma of B7-H3-ADC (I) in a monkey.

FIG. 28 shows a nucleotide sequence (SEQ ID NO: 29) encoding the amino acid sequences of a human light chain signal sequence and a human κ chain constant region.

FIG. 29 shows a nucleotide sequence (SEQ ID NO: 30) encoding the amino acid sequence of a heavy chain of rabbit chimeric antibody 1A3.

FIG. 30 shows a nucleotide sequence (SEQ ID NO: 31) encoding the amino acid sequence of a light chain of rabbit chimeric antibody 1A3.

FIG. 31 shows an amino acid sequence (SEQ ID NO: 32) of a heavy chain of an anti-GPR20 antibody.

FIG. 32 shows an amino acid sequence (SEQ ID NO: 33) of a light chain of an anti-GPR20 antibody.

FIG. 33 shows an amino acid sequence (SEQ ID NO: 34) of a heavy chain of an anti-CDH6 antibody.

FIG. 34 shows an amino acid sequence (SEQ ID NO: 35) of a light chain of an anti-CDH6 antibody.

FIG. 35 shows immunologically stained images using rabbit chimeric antibody 1A3. Immunologically stained images of nude mice, to which human head and neck cancer cell line FaDu was subcutaneously transplanted and administered separately with TROP2-ADC (I) and Anti-TROP2 Ab, are compared.

FIG. 36 shows immunologically stained images using rabbit chimeric antibody 1A3. Images of nude mice, to which GPR20 overexpressing human gastrointestinal stromal tumor cell line GIST-T1/GPR20 was subcutaneously transplanted and administered with GPR20-ADC (I) and not administered with GPR20-ADC (I), are compared.

FIG. 37 shows immunologically stained images using rabbit chimeric antibody 1A3. Images of nude mice, to which a tumor tissue taken from a patient with clear cell renal cell carcinoma was subcutaneously transplanted and administered with CDH6-ADC (I) and not administered with CDH6-ADC (I), are compared.

FIG. 38 shows immunologically stained images using rabbit chimeric antibody 1A3. Images of nude mice, to which a tumor tissue taken from a patient with clear cell renal cell carcinoma was subcutaneously transplanted, administered with CDH6-ADC (I) and stained with a mixture of mouse antibody 1A3 and a compound (2) or a mixture of mouse antibody 1A3 and SN-38 previously prepared or not prepared, are compared.

FIG. 39 shows a calibration curve for quantifying the concentration in plasma of GPR20-ADC (I) in a mouse.

FIG. 40 shows a calibration curve for quantifying concentration in plasma of HER2-ADC (I) in a human.

FIG. 41 shows the inhibition rates of compounds competitively inhibiting recognition of mouse antibody 1A3 to HER2-ADC (I).

DESCRIPTION OF EMBODIMENTS

Hereinafter, preferred modes for carrying out the present invention are described. The embodiments described below are given merely for illustrating one example of a typical embodiment of the present invention and are not intended to limit the scope of the present invention.

1. Definition

In the present invention, "protein" is synonymous with "peptide" or "polypeptide".

In the present invention, "protein" is preferably an antibody or an antigen binding fragment of an antibody. As long as it has a function to recognize an antigen similarly to an antibody, the "protein" may be any protein other than an antibody and an antigen binding fragment of an antibody (antibody alternative). Examples of the antibody alternative include scaffold proteins such as Fibronectin, Protein A, Lipocalin, TrxA, A-domain, Ankyrin repeat, APPI and Ras-binding AF-6 (Kasper Binz H. et al., Current Opinion in Biotechnology 2005, 16: 459-469, Kasper Binz H. et al., Nature Biotechnology 23 (10) 2005, 1257-1268, Skerra A., Current Opinion in Biotechnology 2007, 18: 295-304, Nygren P., FEBS Journal 275 (2008) 2668-2676, Gronwall C. et al., Journal of Biotechnology 140 (2009) 254-269).

In the present invention, "antibody" refers to a glycoprotein having a function to recognize a specific antigen. Examples of the antibody include a polyclonal antibody, a monoclonal antibody, a chimeric antibody, a rabbit type antibody, a humanized antibody and a human antibody.

In the present invention, "antigen" is sometimes used in the meaning of "immunogen".

In the present invention, "antigen binding fragment of an antibody" refers to a partial fragment of an antibody having a function to recognize an antigen and is synonymous with "functional fragment of an antibody". Examples of the antigen binding fragment of an antibody include, but are not limited to, Fab, F(ab')2, scFv, Fab' and a single-strand immunoglobulin. The functional fragment of an antibody may be obtained by treating a full-length antibody molecule with an enzyme such as papain and pepsin. Besides this, the functional fragment of an antibody may be a recombinant protein produced in an appropriate host cell using a recombinant gene.

The phrase that the protein of the present invention "recognizes" an antigen means that the protein of the present invention binds to an antigen through intermolecular force (such as electrostatic interaction, van der Waals force and hydrogen bond). "Recognition" of an antigen by the protein of the present invention can be checked, for example, by detecting signals generated by various immunochemical methods.

The phrase that the "recognition property" of the protein of the present invention to an antigen are different means that binding strength and behavior of the protein of the present invention to antigens substantially differ. Whether the "recognition property" of the protein of the present invention to an antigen are different or not can be checked, for example, by comparing the intensities of signals produced by various immunochemical methods and/or comparing calibration curves representing the concentration of an antigen and the intensity of a signal.

The "moiety" recognized by the protein of the present invention refers to a specific partial structure in a target recognized by the protein of the present invention. The target recognized by the protein of the present invention is referred to as an "antigen" and the specific moiety recognized by the protein of the present invention is sometimes referred to as "epitope".

It is known that each heavy chain and light chain of an antibody has three complementarity determining regions (CDR). The complementarity determining region is also referred to as a hypervariable region (hypervariable domain), which is a site present within the variable region of each heavy chain and light chain of an antibody and having a particularly high primary-structure mutation rate. The CDR is usually present in three discrete sites on the primary structure of each of the polypeptide chains of a heavy chain and a light chain. In the present invention, complementarity determining regions of an antibody are expressed as follows: the complementarity determining regions in a heavy chain are expressed as CDRH1, CDRH2 and CDRH3 sequentially from the amino terminus of the heavy chain amino acid sequence; whereas, the complementarity determining regions in a light chain are expressed as CDRL1, CDRL2 and CDRL3 sequentially from the amino terminus of the light chain amino acid sequence. In the tertiary structure, these regions are present close to each other and involved in determination of specificity to an antigen.

In the present invention, "gene" refers to a nucleotide comprising a nucleotide sequence encoding amino acids of a protein or a complementary strand thereof, for example, a polynucleotide, an oligonucleotide, DNA, mRNA, cDNA and cRNA, which are nucleotides comprising a nucleotide sequence encoding amino acids of a protein or a complementary strand thereof, are included in the meaning of "gene". The gene as mentioned above consists of nucleotides of a single strand, double strand or triple strand or larger. A pair of a DNA strand and an RNA strand, ribonucleotide (RNA) and deoxyribonucleotide (DNA) co-present on a single nucleotide chain, and a double strand or triple strand or larger comprising such a nucleotide chain are included in the meaning of "gene".

In the present invention, "nucleotide" is synonymous with "nucleic acid"; for example, DNA, RNA, a probe, an oligonucleotide, a polynucleotide and a primer are included in the meaning of "nucleotide". Such a nucleotide is a nucleotide consisting of a single strand, double strand or triplet strand or larger. A pair of a DNA strand and an RNA strand, ribonucleotide (RNA) and deoxyribonucleotide (DNA) co-present on a single nucleotide chain and a pair of a double strand or triple strand or larger comprising such a nucleotide chain are included in the meaning of "nucleotide".

In the present invention, "cells" include various cells derived from animals, subcultured cells, primary cultured cells, cell strains, recombinant cells and microorganisms.

2. Antibody-Drug Conjugate

In the present invention, "antibody-drug conjugate" refers to a conjugate obtained by conjugating an antibody and a drug via a linker.

In the present invention, "drug-linker" refers to a partial structure of an antibody-drug conjugate and consisting of a linker and a drug.

The protein of the present invention is characterized by recognizing a drug moiety of an antibody-drug conjugate (hereinafter referred to as "the antibody-drug conjugate according to the present invention") in which a drug (hereinafter referred to as "compound (1)") represented by the following formula:

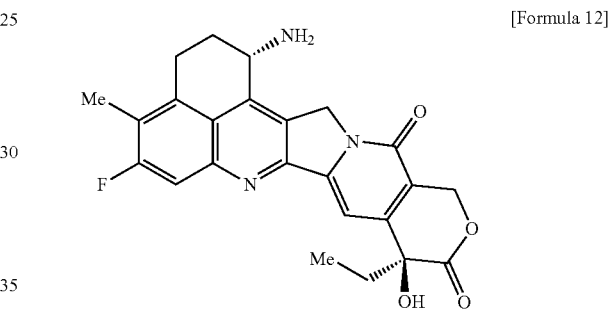

[Formula 12]

and an antibody are conjugated via a linker.

Compound (1) is an antitumor drug called exatecan (which can be also expressed by IUPAC name: (1S,9S)-1-amino-9-ethyl-5-fluoro-1,2,3,9,12,15-hexahydro-9-hydroxy-4-methyl-10H,13H-benzo[de]pyrano[3',4':6,7]indolizino[1,2-b]quinoline-10,13-dione, or chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13 (9H,15H)-dione) and known to have topoisomerase I inhibitory activity.

Note that, the protein of the present invention can also recognize compound (1), itself.

Examples of the antibody in the antibody-drug conjugate according to the present invention include, but are not particularly limited to, an anti-HER2 antibody, an anti-HER3 antibody, an anti-TROP2 antibody, an anti-B7-H3 antibody, an anti-CD3 antibody, an anti-CD30 antibody, an anti-CD33 antibody, an anti-CD37 antibody, an anti-CD56 antibody, an anti-CD98 antibody, an anti-DR5 antibody, an anti-EGFR antibody, an anti-EPHA2 antibody, an anti-FGFR2 antibody, an anti-FGFR4 antibody, an anti-FOLR1 antibody, an anti-VEGF antibody, an anti-CD20 antibody, an anti-CD22 antibody, an anti-CD70 antibody, an anti-PSMA antibody, an anti-CEA antibody, an anti-Mesothelin antibody, an anti-A33 antibody, an anti-CanAg antibody, an anti-Cripto antibody, an anti-G250 antibody, an anti-MUC1 antibody, an anti-GPNMB antibody, an anti-Integrin antibody, an anti-Tenascin-C antibody, an anti-SLC44A4 antibody, an anti-GPR20 antibody and an anti-CDH6 antibody. Further, an anti-HER2 antibody, an anti-HER3 antibody, an anti-TROP2 antibody, an anti-B7-H3 antibody, an anti-GPR20 antibody, and anti-CDH6 antibody can be preferably exemplified.

In the present invention, "anti-HER2 antibody" refers to an antibody which binds specifically to HER2 (Human Epidermal Growth Factor Receptor Type 2; ErbB-2), and preferably has an activity of internalization in HER2 expressing cells by binding to HER2.

Examples of the anti-HER2 antibody include trastuzumab (U.S. Pat. No. 5,821,337) and pertuzumab (International Publication No. WO 01/00245). Preferably, trastuzumab can be exemplified.

In the present invention, "anti-HER3 antibody" refers to an antibody which binds specifically to HER3 (Human Epidermal Growth Factor Receptor Type 3; ErbB-3), and preferably has an activity of internalization in HER3 expressing cells by binding to HER3.

Examples of the anti-HER3 antibody include patritumab (U3-1287), U1-59 (International Publication No. WO 2007/077028), MM-121 (seribantumab), anti-ERBB3 antibody described in International publication No. WO 2008/100624, RG-7116 (lumretuzumab) and LJM-716 (elgemtumab). Preferably, patrizumab and U1-59 can be exemplified.

In the present invention, "anti-TROP2 antibody" refers to an antibody which binds specifically to TROP2 (TACSTD2: Tumor-associated calcium signal transducer 2; EGP-1), and preferably has an activity of internalization in TROP2 expressing cells by binding to TROP2.

Examples of the anti-TROP2 antibody include hTINA1-Hill (International Publication No. WO 2015/098099).

In the present invention, "anti-B7-H3 antibody" refers to an antibody which binds specifically to B7-H3 (B cell antigen #7 homolog 3; PD-L3; CD276), and preferably has an activity of internalization in B7-H3 expressing cells by binding to B7-H3.

Examples of the anti-B7-H3 antibody include M30-H1-L4 (International Publication No. WO 2014/057687).

In the present invention, "anti-GPR20 antibody" refers to an antibody which binds specifically to GPR20 (G Protein-coupled receptor 20), and preferably has an activity of internalization in GPR20 expressing cells by binding to GPR20.

Examples of the anti-GPR20 antibody include h046-H4e/L7 (International Publication No. WO 2018/135501).

In the present invention, "anti-CDH6 antibody" refers to an antibody which binds specifically to CDH6 (Cadherin-6), and preferably has an activity to internalize in CDH6 expressing cells by binding to CDH6.

Examples of the anti-CDH6 antibody include H01L02 (International Publication No. WO 2018/212136).

The protein of the present invention is characterized by specifically recognizing a drug moiety of, preferably, an antibody-drug conjugate (hereinafter referred to as "antibody-drug conjugate (I)") having a drug-linker represented by the following formula:

[Formula 13]

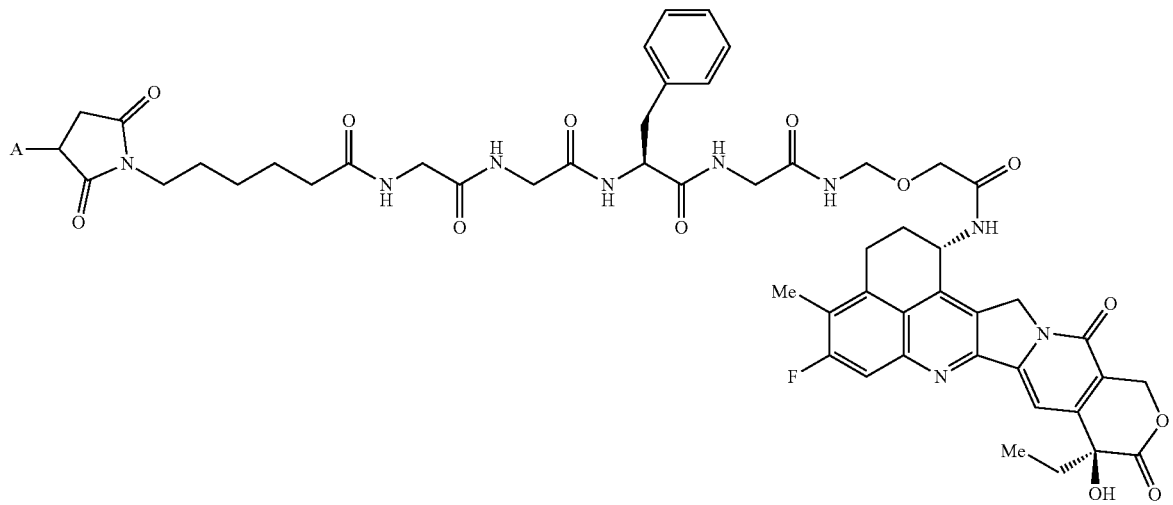

wherein A represents a connecting position to an antibody, and the drug-linker is conjugated to the antibody via a thioether bond;

an antibody-drug conjugate (hereinafter referred to as "antibody-drug conjugate (II)") having a drug-linker represented by the following formula:

[Formula 14]

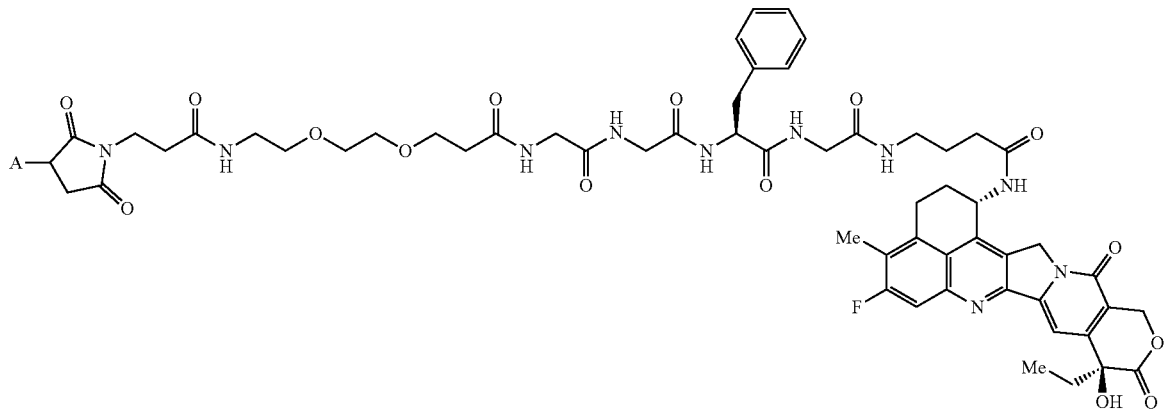

wherein A represents a connecting position to an antibody, and the drug-linker is conjugated to the antibody via a thioether bond; or an antibody-drug conjugate (hereinafter referred to as "antibody-drug conjugate (III)") having a drug-linker represented by the following formula:

[Formula 15]

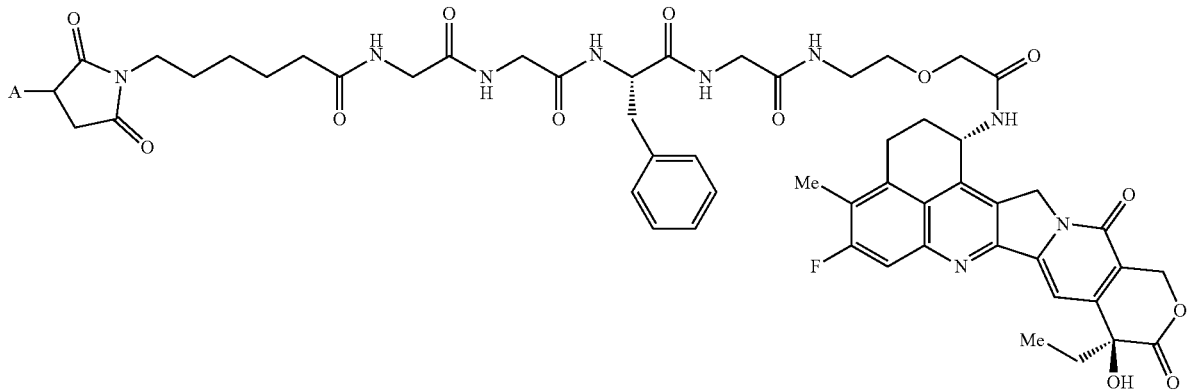

wherein A represents a connecting position to an antibody, the drug-linker is conjugated to the antibody via a thioether bond.

Each of the drug-linkers of the antibody-drug conjugates (I) to (III) connects to a thiol group (in other words, a sulfur atom of a cysteine residue) formed at an interchain disulfide bond site (two sites between heavy chains, and two sites between a heavy chain and a light chain).

The protein of the present invention is more preferably characterized by specifically recognizing the drug moiety of antibody-drug conjugate (I).

Antibody-drug conjugate (I) can also be represented by the following formula:

[Formula 16]

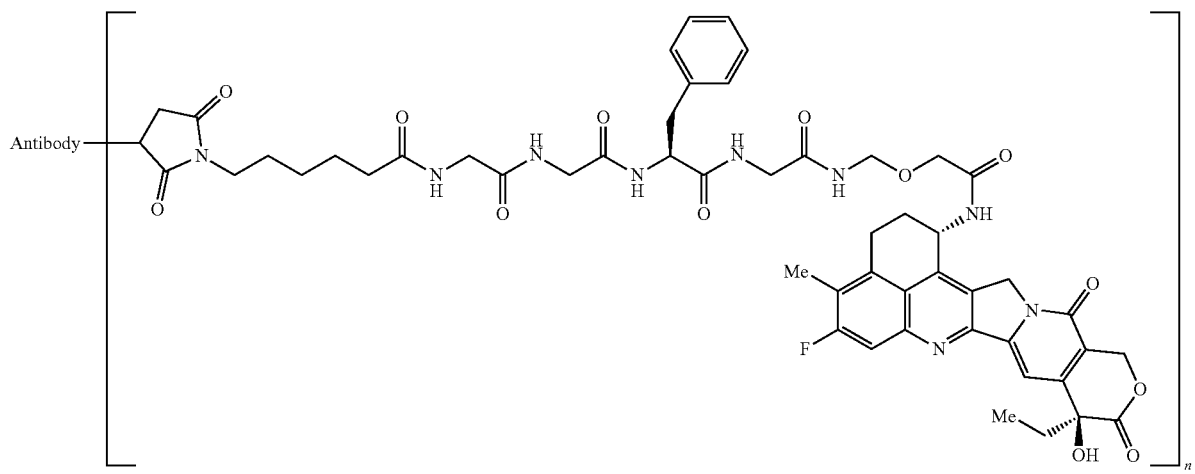

wherein the drug-linker is conjugated to the antibody via a thioether bond. The meaning of n is the same as that of what is called the average number of conjugated drug molecules (DAR; Drug-to-Antibody Ratio), and indicates the average number of units of the drug-linker conjugated per antibody molecule.

Note that, the average number of conjugated drug molecules per antibody molecule of the antibody-drug conjugate according to the present invention can be determined, for example, by a method of calculation based on measurement of UV absorbance for the antibody-drug conjugate and the conjugation precursor thereof at two wavelengths of 280 nm and 370 nm (UV method), or a method of calculation based on quantification through HPLC measurement for fragments obtained by treating the antibody-drug conjugate with a reducing agent (HPLC method).

After migrating into cancer cells, antibody-drug conjugate (I) is cleaved at the linker portion to release the compound represented by the following formula:

[Formula 17]

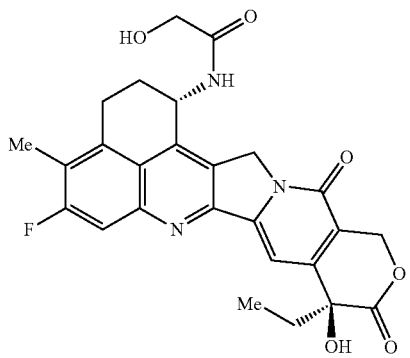

(hereinafter referred to as "compound (2)").

The compound (2) is inferred to be formed by decomposition of an aminal structure of a compound represented by the following formula:

[Formula 18]

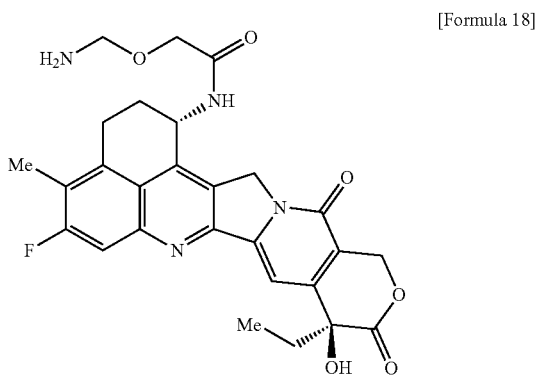 [SMILES: CC[C@@]1(O)C(=O)OCc2c1cc1n(c2=O)Cc2c-1nc1cc(F)c(C)c3c1c2[C@@H](NC(=O)COCN)CC3]

(hereinafter referred to as "compound (3)") which is inferred to be formed by cleavage of the linker part of the antibody-drug conjugate used in the present invention.

Compound (2) is inferred to be the original source of the antitumor activity of antibody-drug conjugate (I) and has been confirmed to have a topoisomerase I inhibitory effect (Ogitani Y. et al., Clinical Cancer Research, 2016, Oct. 15; 22 (20): 5097-5108, Epub 2016 Mar. 29).

Note that, the protein of the present invention can also recognize compound (2) itself released from antibody-drug conjugate (I).

Antibody-drug conjugate (II) can also be represented by the following formula:

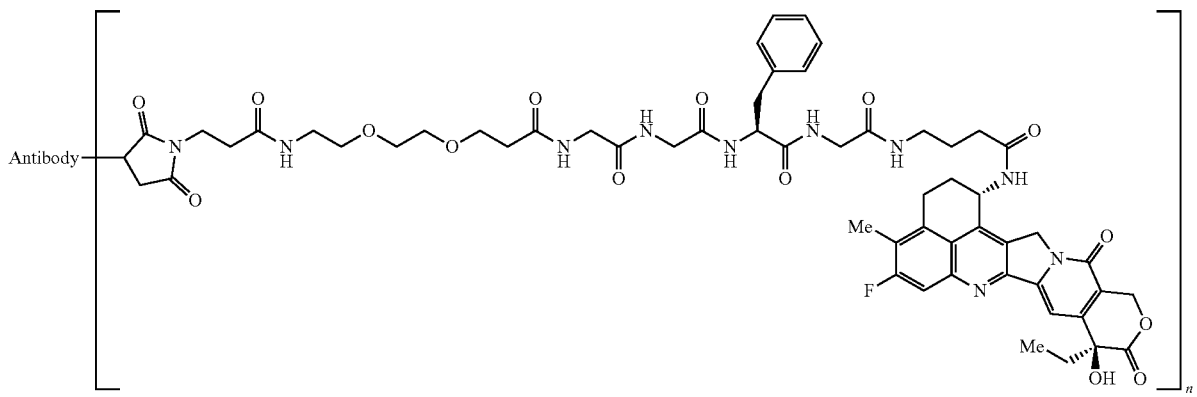

wherein the drug-linker is conjugated to an antibody via a thioether bond. The meaning of n is the same as that of what is called DAR and indicates the average number of units of the drug-linker conjugated per antibody molecule.

After migrating into cancer cells, antibody-drug conjugate (II) is cleaved at the linker portion to release a compound represented by the following formula:

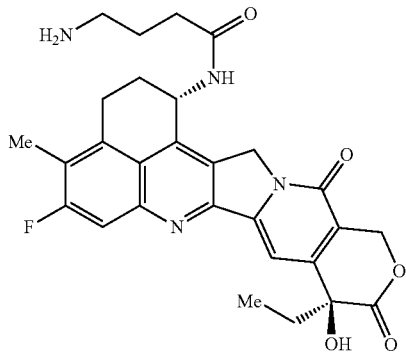

(hereinafter referred to as "compound (4)")

Note that, the protein of the present invention can also recognize compound (4) itself released from the antibody-drug conjugate (II).

The antibody-drug conjugate (III) can also be represented by the following formula:

wherein the drug-linker is conjugated to an antibody via a thioether bond. The meaning of n is the same as that of what is called DAR and indicates the average number of units of the drug-linker conjugated per antibody molecule.

After migrating into cancer cells, antibody-drug conjugate (III) is cleaved at the linker portion to release the compound (hereinafter referred to as "compound (5)") represented by the following formula:

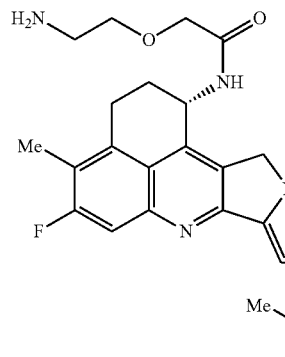

Note that, the protein of the present invention can also recognize compound (5) itself released from the antibody-drug conjugate (III).

In the present invention, "anti-HER2 antibody-drug conjugate" refers to an antibody-drug conjugate such that the

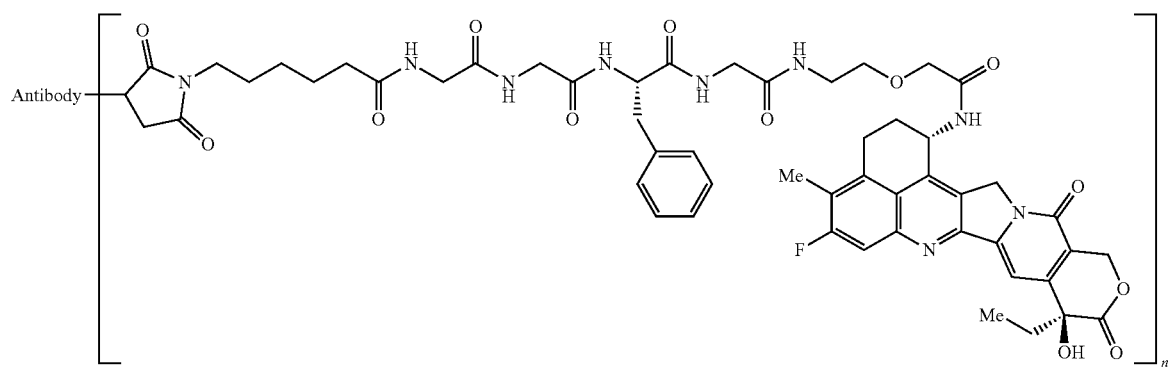

antibody in the antibody-drug conjugate according to the present invention is an anti-HER2 antibody.

The anti-HER2 antibody is preferably an antibody comprising a heavy chain consisting of the amino acid sequence consisting of amino acid residues 1 to 449 of SEQ ID NO: 21 and a light chain consisting of the amino acid sequence consisting of amino acid residues 1 to 214 of SEQ ID NO: 22, or an antibody comprising a heavy chain consisting of the amino acid sequence represented by SEQ ID NO: 21 and a light chain consisting of the amino acid sequence represented by SEQ ID NO: 22.

The average number of units of the drug-linker conjugated per antibody molecule in the anti-HER2 antibody-drug conjugate is preferably 2 to 8, more preferably 3 to 8, even more preferably 7 to 8, even more preferably 7.5 to 8, and even more preferably about 8.

The anti-HER2 antibody-drug conjugate can be produced with reference to descriptions in Publications such as International Publication No. WO 2015/115091.

In the present invention, "anti-HER3 antibody-drug conjugate" refers to an antibody-drug conjugate such that the antibody in the antibody-drug conjugate according to the present invention is an anti-HER3 antibody.

The anti-HER3 antibody is preferably an antibody comprising a heavy chain consisting of CDRH1 consisting of amino acid sequence of amino acid residues 26 to 35 of SEQ ID NO: 23, CDRH2 consisting of amino acid sequence of amino acid residues 50 to 65 of SEQ ID NO: 23 and CDRH3 consisting of amino acid sequence of amino acid residues 98 to 106 of SEQ ID NO: 23, and a light chain consisting of CDRL1 consisting of amino acid sequence of amino acid residues 24 to 39 of SEQ ID NO: 24, CDRL2 consisting of amino acid sequence of amino acid residues 56 to 62 of SEQ ID NO: 24 and CDRL3 consisting of amino acid sequence of amino acid residues 95 to 103 of SEQ ID NO: 24; more preferably an antibody comprising a heavy chain comprising a heavy chain variable region consisting of amino acid sequence of amino acid residues 1 to 117 of SEQ ID NO: 23 and a light chain comprising a light chain variable region consisting of amino acid residues 1 to 113 of SEQ ID NO: 24; and even more preferably, an antibody comprising a heavy chain consisting of amino acid sequence represented by SEQ ID NO: 23 and a light chain consisting of amino acid sequence represented by SEQ ID NO: 24 or a variant of the antibody in which a lysine residue at the carboxyl terminus of the heavy chain is deleted.

The average number of units of the drug-linker conjugated per antibody molecule in the anti-HER3 antibody-drug conjugate is preferably 2 to 8, more preferably 3 to 8, even more preferably 7 to 8, even more preferably 7.5 to 8 and even more preferably about 8.

The anti-HER3 antibody-drug conjugate can be produced with reference to descriptions in publications such as International Publication No. WO 2015/155998.

In the present invention, "anti-TROP2 antibody-drug conjugate" refers to an antibody-drug conjugate such that the antibody in the antibody-drug conjugate according to the present invention is an anti-TROP2 antibody.

The anti-TROP2 antibody is preferably an antibody comprising a heavy chain consisting of CDRH1 consisting of amino acid sequence of amino acid residues 50 to 54 of SEQ ID NO: 25, CDRH2 consisting of amino acid sequence of amino acid residues 69 to 85 of SEQ ID NO: 25, and CDRH3 consisting of amino acid sequence of amino acid residues 118 to 129 of SEQ ID NO: 25, and a light chain comprising CDRL1 consisting of amino acid sequence of amino acid residues 44 to 54 of SEQ ID NO: 26, CDRL2 consisting of amino acid sequence of amino acid residues 70 to 76 of SEQ ID NO: 26, and CDRL3 consisting of amino acid sequence of amino acid residues 109 to 117 of SEQ ID NO: 26;

more preferably an antibody comprising a heavy chain comprising a heavy chain variable region consisting of amino acid sequence of amino acid residues 20 to 140 of SEQ ID NO: 25 and a light chain comprising a light chain variable region consisting of amino acid residues 21 to 129 of SEQ ID NO: 26; and even more preferably, an antibody comprising a heavy chain consisting of amino acid sequence of amino acid residues 20 to 470 of SEQ ID NO: 25 and a light chain consisting of amino acid sequence of amino acid residues 21 to 234 of SEQ ID NO: 26 or a variant of the antibody in which a lysine residue at the carboxyl terminus of the heavy chain is deleted.

The average number of units of the drug-linker conjugated per antibody molecule in the anti-TROP2 antibody-drug conjugate is preferably 2 to 8, more preferably 3 to 5, even more preferably 3.5 to 4.5, and even more preferably about 4.

The anti-TROP2 antibody-drug conjugate can be produced with reference to descriptions in publications such as International Publication No. WO 2015/098099.

In the present invention, "anti-B7-H3 antibody-drug conjugate" refers to an antibody-drug conjugate such that the antibody in the antibody-drug conjugate according to the present invention is an anti-B7-H3 antibody.

The anti-B7-H3 antibody is preferably an antibody comprising a heavy chain comprising CDRH1 consisting of amino acid sequence of amino acid residues 50 to 54 of SEQ ID NO: 27, CDRH2 consisting of amino acid sequence of amino acid residues 69 to 85 of SEQ ID NO: 27 and CDRH3 consisting of amino acid sequence of amino acid residues 118 to 130 of SEQ ID NO: 27, and a light chain consisting of CDRL1 consisting of amino acid sequence of amino acid residues 44 to 53 of SEQ ID NO:28, CDRL2 consisting of amino acid sequence of amino acid residues 69 to 75 of SEQ ID NO: 28 and CDRL3 consisting of amino acid sequence of amino acid residues 108 to 116 of SEQ ID NO: 28;

more preferably, an antibody comprising a heavy chain containing a heavy chain variable region consisting of amino acid sequence of amino acid residues 20 to 141 of SEQ ID NO: 27 and a light chain comprising a light chain variable region consisting of amino acid residues 21 to 128 of SEQ ID NO: 28; and even more preferably, an antibody comprising a heavy chain consisting of amino acid sequence of amino acid residues 20 to 471 of SEQ ID NO: 27 and a light chain consisting of amino acid sequence of amino acid residues 21 to 233 of SEQ ID NO: 28 or a variant of the antibody in which a lysine residue at the carboxyl terminus of the heavy chain is deleted.

The average number of units of the drug-linker conjugated per antibody molecule in the anti-B7-H3 antibody-drug conjugate is preferably 2 to 8, more preferably 3 to 5, even more preferably 3.5 to 4.5, and even more preferably about 4.

The anti-B7-H3 antibody-drug conjugate can be produced with reference to descriptions in publications such as International Publication No. WO 2014/057687.

In the present invention, "anti-GPR20 antibody-drug conjugate" refers to an antibody-drug conjugate such that the antibody in the antibody-drug conjugate according to the present invention is an anti-GPR20 antibody.

The anti-GPR20 antibody is preferably an antibody comprising a heavy chain consisting of CDRH1 consisting of amino acid sequence of amino acid residues 45 to 54 of SEQ ID NO: 32, CDRH2 consisting of amino acid sequence of amino acid residues 69 to 78 of SEQ ID NO: 32 and CDRH3 consisting of amino acid sequence of amino acid residues 118 to 131 of SEQ ID NO:32, and a light chain consisting of CDRL1 consisting of amino acid sequence of amino acid residues 44 to 54 of SEQ ID NO:33, CDRL2 consisting of amino acid sequence of amino acid residues 70 to 76 of SEQ ID NO: 33 and CDRL3 consisting of amino acid sequence of amino acid residues 109 to 117 of SEQ ID NO: 33;
  more preferably, an antibody comprising a heavy chain containing a heavy chain variable region consisting of amino acid sequence of amino acid residues 20 to 142 of SEQ ID NO: 32 and a light chain containing a light chain variable region consisting of amino acid residues 21 to 129 of SEQ ID NO: 33; and
  even more preferably, an antibody comprising a heavy chain consisting of amino acid sequence of amino acid residues 20 to 472 of SEQ ID NO: 32 and a light chain consisting of amino acid sequence of amino acid residues 21 to 234 of SEQ ID NO: 33 or a variant of the antibody in which a lysine residue at the carboxyl terminus of the heavy chain is deleted.

The average number of units of the drug-linker conjugated per antibody molecule in the anti-GPR20 antibody-drug conjugate is preferably 2 to 8, more preferably 3 to 8, even more preferably 7 to 8, even more preferably 7.5 to 8, and even more preferably about 8.

The anti-GPR20 antibody-drug conjugate can be produced with reference to descriptions in publications such as International Publication No. WO 2018/135501.

In the present invention, "anti-CDH6 antibody-drug conjugate" refers to an antibody-drug conjugate such that the antibody in the antibody-drug conjugate according to the present invention is an anti-CDH6 antibody.

The anti-CDH6 antibody is preferably an antibody comprising a heavy chain consisting of CDRH1 consisting of amino acid sequence of amino acid residues 45 to 54 of SEQ ID NO: 34, CDRH2 consisting of amino acid sequence of amino acid residues 69 to 78 of SEQ ID NO: 34 and CDRH3 consisting of amino acid sequence of amino acid residues 118 to 130 of SEQ ID NO: 34, and a light chain consisting of CDRL1 consisting of amino acid sequence of amino acid residues 44 to 54 of SEQ ID NO:35, CDRL2 consisting of amino acid sequence of amino acid residues 70 to 76 of SEQ ID NO: 35 and CDRL3 consisting of amino acid sequence of amino acid residues 109 to 116 of SEQ ID NO: 35;
  more preferably an antibody comprising a heavy chain comprising a heavy chain variable region consisting of amino acid sequence of amino acid residues 20 to 141 of SEQ ID NO: 34 and a light chain comprising a light chain variable region consisting of amino acid residues 21 to 128 of SEQ ID NO: 35; and
  even more preferably, an antibody comprising a heavy chain consisting of amino acid sequence of amino acid residues 20 to 471 of SEQ ID NO: 34 and a light chain consisting of amino acid sequence of amino acid residues 21 to 233 of SEQ ID NO: 35 or a variant of the antibody in which a lysine residue at the carboxyl terminus of the heavy chain is deleted.

The average number of units of the drug-linker conjugated per antibody molecule in the anti-CDH6 antibody-drug conjugate is preferably 2 to 8, more preferably 3 to 8, even more preferably 7 to 8, further more preferably 7.5 to 8, and even more preferably about 8.

The anti-CDH6 antibody-drug conjugate can be produced with reference to descriptions in publications such as International Publication No. WO 2018/212136.

3. Production of the Protein of the Present Invention

The protein of the present invention can be preferably obtained as an antibody (hereinafter referred to as "the antibody of the present invention"). The antibody of the present invention can be obtained by immunizing animals with an antigenic protein obtained by conjugating compound (1) or a derivative thereof and a carrier protein via a linker, and collecting the antibodies produced in vivo and then, purifying it.

As the antigen protein, a protein prepared by adding a carrier protein to the compound represented, for example, by the following formula:

[Formula 23]

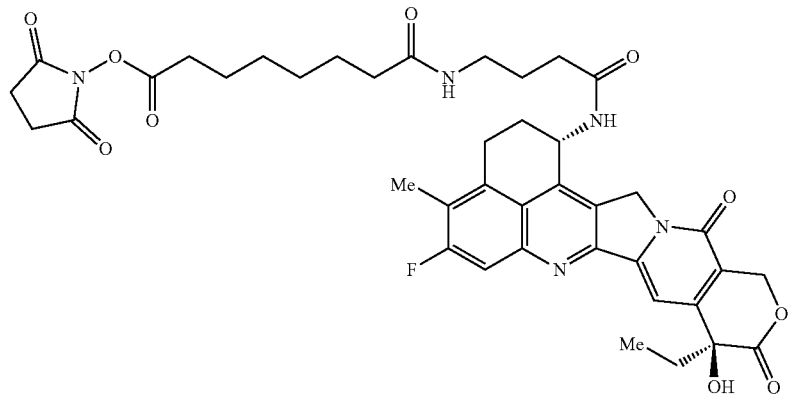

(hereinafter referred to as "compound" (6)) can be used.

The carrier protein is not particularly limited as long as it can induce immune response even if it is a small antigen such as a lower molecule compound or a peptide. For example, bovine thyroglobulin and bovine serum albumin (BSA) and Keyhole limpet hemocyanin (KLH) can be used.

From the antiserums obtained, an antiserum having desired properties can be selected by ELISA method using a positive control and a negative control.

As the positive control, for example, compound (1), compound (2) and compound (6) can be exemplified. Antiserum having a high inhibition effect can be selected using these as positive controls.

Note that, it is known that equilibrium of the lactone ring of compound (1) shifts toward a closed ring in an acidic aqueous solvent (for example, about pH3); whereas the ring shifts towards an open ring in a basic aqueous solvent (for example, about pH10). In order to select an antibody recognizing the basic skeleton of the compound (1) itself no matter whether a lactone ring is opened or closed, a compound having a reduced lactone ring, for example, a compound represented by the following formula:

[Formula 24]

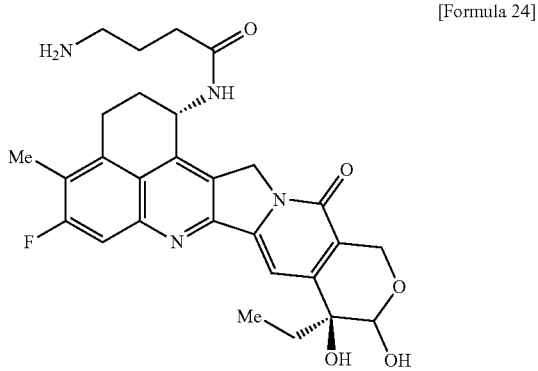

(hereinafter referred to as "compound (7)") can be also used as a positive control. The antiserum having a high inhibition effect can be selected as the positive control. Note that, in order to select an antibody recognizing compound (1) and compound (7) at the same level, it is preferable to exclude an antibody moiety particularly highly recognizing compound (7) rather than compound (1).

The antibody-drug conjugate according to the present invention (preferably, antibody-drug conjugates (I), (II) and (III)) can be used as a positive control. Antiserum having a high inhibition effect can be selected using these as positive controls.

In order to exclude an antibody recognizing a part distantly positioned from the basic skeleton of compound (1), for example, a compound consisting of a cyclohexane ring, a partial structure near a linker and represented by the following formula:

[Formula 25]

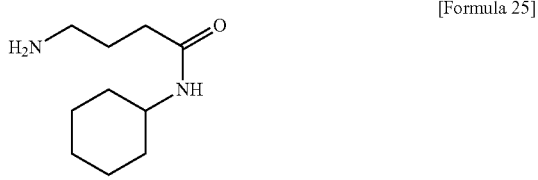 [SMILES: NCCCC(=O)NC1CCCCC1]

(hereinafter referred to as "compound (8)") can be used as a negative control. Antiserum exhibiting a high inhibition effect can be excluded using this as a negative control.

The cells producing the antibody of the present invention can be obtained by cloning the antiserum selected as mentioned above.

In accordance with a method known in the art (for example, Kohler and Milstein, Nature (1975) 256, p. 495-497, Kennet, R. ed., Monoclonal Antibodies, p. 365-367, Plenum Press, N.Y. (1980)), cells producing the antibody of the present invention are fused with myeloma cells to establish hybridoma cells, from which monoclonal antibodies can be obtained. Examples of such a method are more specifically described in International Publication No. WO 09/48072 published Apr. 16, 2009) and WO10/117011 (published Oct. 14, 2010).

The antibody obtained can be uniformly purified. For separation and purification of the antibody, customary separation and purification methods used for protein may be used. The antibody can be separated and purified appropriately selecting and combining, for example, column chromatography, filtration by filter, ultrafiltration, salting out, dialysis, polyacrylamide gel electrophoresis for preparation and isoelectric point electrophoresis (Strategies for Protein Purification and Characterization: A Laboratory Course Manual, Daniel R. Marshak et al. eds., Cold Spring Harbor Laboratory Press (1996), Antibodies: A Laboratory Manual. Ed Harlow and David Lane, Cold Spring Harbor Laboratory (1988); however, the separation and purification methods are not limited to these.

Examples of the chromatography include affinity chromatography, ion exchange chromatography, hydrophobic chromatography, gel filtration chromatography, reversed-phase chromatography and adsorption chromatography. These chromatographic methods can be carried out using liquid chromatography such as HPLC and FPLC. Examples of the column to be used in affinity chromatography include protein A column and protein G column. Examples of the column using protein A column include Hyper D, POROS and Sepharose F. F. (Pharmacia). Also, an antibody can be purified using a carrier having an antigen immobilized thereon and taking advantage of binding ability to the antigen.

The antibody of the present invention is further characterized in that its recognition property to the antibody-drug conjugate according to the present invention is substantially independent of any difference in the average number of units of the drug-linker conjugated per antibody molecule (DAR) in the antibody-drug conjugate. The fact that the antibody has such a characteristic can be confirmed, for example, based on the fact that a calibration curve to the antibody-drug conjugate having a high DAR (DAR8) does not substantially differ from a calibration curve to the antibody-drug conjugate having a low DAR (DAR4).

As the antibody of the present invention obtained as described above, for example, mouse antibody 1A3, can be exemplified. The amino acid sequence of a heavy chain variable region of mouse antibody 1A3 is the amino acid sequence consisting of amino acid residues 20 to 141 of SEQ ID NO: 15, and the nucleotide sequence encoding the amino acid sequence is the nucleotide sequence consisting of nucleotide residues 58 to 423 of SEQ ID NO: 17. The amino acid sequence of a light chain variable region of mouse antibody 1A3 is the amino acid sequence consisting of amino acid residues 21 to 127 of SEQ ID NO: 16; and the nucleotide sequence encoding the amino acid sequence is the nucleotide sequence consisting of nucleotide residues 61 to 381 of SEQ ID NO: 18.

The antibody of the present invention is satisfactory if it is an antibody having all 6 CDR sequences derived from mouse antibody 1A3, and specifically recognizes the drug moiety of the antibody-drug conjugate according to the present invention. Several methods are known for use in determining a CDR sequence. For example, the Abm definition, Chothia definition, Kabat definition and Imgt (registered trademark) (The International ImMunoGeneTics information system (registered trademark)) are exemplified. The CDR sequences of the antibody of the present invention may be defined by any one of the methods.

According to the Abm definition, the heavy chain variable region of the antibody of the present invention has CDRH1 (GFTFSDYGMV) consisting of the amino acid sequence represented by SEQ ID NO: 1, CDRH2 (YISSGSSAIY) consisting of the amino acid sequence represented by SEQ ID NO: 2, and CDRH3 (PPRYDVYSAWFAY) consisting of the amino acid sequence represented by SEQ ID NO: 3; and the light chain variable region of the antibody of the present invention has CDRL1 (KASQDVGSAVV) consisting of the amino acid sequence represented by SEQ ID NO: 4, CDRL2 (WASTRHT) consisting of the amino acid sequence represented by SEQ ID NO: 5, and CDRL3 (QQYSSYPVT) consisting of the amino acid sequence represented by SEQ ID NO: 6.

According to the Chothia definition, the heavy chain variable region of the antibody of the present invention has CDRH1 (GFTFSDY) consisting of the amino acid sequence represented by SEQ ID NO: 7, CDRH2 (SSGSSA) consisting of the amino acid sequence represented by SEQ ID NO: 8, and CDRH3 (PPRYDVYSAWFAY) consisting of the amino acid sequence represented by SEQ ID NO: 3; and the light chain variable region of the antibody of the present invention has CDRL1 (KASQDVGSAVV) consisting of the amino acid sequence represented by SEQ ID NO: 4, CDRL2 (WASTRHT) consisting of the amino acid sequence represented by SEQ ID NO: 5, and CDRL3 (QQYSSYPVT) consisting of the amino acid sequence represented by SEQ ID NO: 6.

According to the Kabat definition, the heavy chain variable region of the antibody of the present invention has CDRH1 (DYGMV) consisting of the amino acid sequence represented by SEQ ID NO: 9, CDRH2 (YISSGSSAIYY-ADTVKG) consisting of the amino acid sequence represented by SEQ ID NO: 10, and CDRH3 (PPRYDVYSAW-FAY) consisting of the amino acid sequence represented by SEQ ID NO: 3; and the light chain variable region of the antibody of the present invention has CDRL1 (KASQDVGSAVV) consisting of the amino acid sequence represented by SEQ ID NO: 4, CDRL2 (WASTRHT) consisting of the amino acid sequence represented by SEQ ID NO: 5, and CDRL3 (QQYSSYPVT) consisting of the amino acid sequence represented by SEQ ID NO: 6.

According to Imgt (registered trademark) definition, the heavy chain variable region of the antibody of the present invention has CDRH1 (GFTFSDYG) consisting of the amino acid sequence represented by SEQ ID NO: 11, CDRH2 (ISSGSSAI) consisting of the amino acid sequence represented by SEQ ID NO: 12, and CDRH3 (ARPPRYDVYSAWFAY) consisting of the amino acid sequence represented by SEQ ID NO: 13; and the light chain variable region of the antibody of the present invention has CDRL1 (QDVGSA) consisting of the amino acid sequence represented by SEQ ID NO: 14, CDRL2 consisting of a tripeptide represented by WAS (tryptophan-alanine-serine), and CDRL3 (QQYSSYPVT) consisting of the amino acid sequence represented by SEQ ID NO: 6.

The antibody of the present invention includes not only monoclonal antibodies mentioned above but also a gene-recombinant antibody, which is obtained by adding artificial modification for decreasing heterologous antigenicity, such as a chimeric antibody, a humanized antibody, a rabbit type antibody or a mouse type antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region, can be exemplified (Proc. Natl. Acad. Sci. USA, 81, 6851-6855, (1984)). As another example, a chimeric antibody in which a mouse- or rat-derived antibody variable region is connected to a rabbit-derived antibody constant region, can be exemplified.

As a specific example of the rabbit chimeric antibody, an antibody (rabbit chimeric antibody 1A3) comprising a heavy chain comprising mouse antibody 1A3-derived heavy chain variable region and a rabbit antibody-derived heavy chain constant region, and a light chain comprising mouse antibody 1A3-derived light chain variable region and a rabbit antibody-derived light chain constant region, can be exemplified. The heavy chain of the rabbit chimeric antibody 1A3 consists of the amino acid sequence consisting of amino acid residues 20 to 464 of SEQ ID NO: 19; whereas, the light chain of the rabbit chimeric antibody 1A3 consists of the amino acid sequence consisting of amino acid residues 21 to 233 of SEQ ID NO: 20.

As a non-clinical animal model for cancer research, mice are frequently used. If a mouse antibody is used, in order to avoid competition with an endogenous mouse IgG, the method that can be used is limited. Then, a rabbit chimeric antibody is used because it is possible to compare a mouse-derived sample and a human derived sample in a same platform and useful for translational research.

As the humanized antibody, an antibody obtained by integrating the complementarity determining region (CDR) alone into a human-derived antibody (Nature (1986) 321, pp. 522-525), and an antibody obtained by grafting a part of the amino acid residues of a framework as well as the CDR sequence to a human antibody (WO 90/07861), can be exemplified. As the rabbit type antibody, an antibody obtained by integrating the complementarity determining region (CDR) alone into a rabbit-derived antibody and an antibody obtained by grafting a part of the amino acid residues of a framework as well as the CDR sequence to a rabbit antibody, can be exemplified.

It is known that, in an antibody produced by culturing mammalian cells, a lysine residue at the carboxyl terminus of the heavy chain is deleted (Journal of Chromatography A, 705: 129-134 (1995)). It is also known that two amino acid residues (glycine and lysine) are deleted from the heavy chain carboxyl terminus and a proline residue positioned at the carboxyl terminus is newly amidated (Analytical Biochemistry, 360: 75-83 (2007)). However, such deletion and modification of the heavy chain sequence do not affect the antigen-binding affinity and the effector function (the activation of complement, antibody-dependent cellular cytotoxicity, etc.) of the antibody. Therefore, in the present invention, antibodies subjected to such modification are included, and deletion variants in which one or two amino acids have been deleted at the carboxyl terminus of the heavy chain, variants obtained by amidation of deletion variants (for example, a heavy chain in which the carboxyl terminus proline residue has been amidated), and the like can be exemplified. The type of deletion variant having a deletion at the carboxyl terminus of the heavy chain of the antibody according to the present invention is not limited to the above types of variants as long as the antigen-binding affinity and the effector function are conserved. The two heavy chains constituting the antibody according to the present invention may be any one of heavy chains selected from the group consisting of a full-length heavy chain and the above-described deletion variants or a combination of any two of these. The ratio of the amount of each deletion variant may sometimes be affected by the type of cultured mammalian cells which produce the antibody according to the present invention and the culture conditions; however, the case where one amino acid residue at the carboxyl terminus has been deleted in both of the two heavy chains can be exemplified as a main component of the antibody according to the present invention.

The antibody of the present invention may be an antibody consisting of amino acid sequence having an identity of at least 95% (preferably, at least 99%) with the amino acid sequence of mouse antibody 1A3 or rabbit chimeric antibody 1A3 as long as the characteristics of the antibody of the present invention are maintained.

The identity between two types of amino acid sequences can be determined by use of default parameter of Blast (Nucl. Acids Res., 25, p. 3389-3402 (1997)). Blast can be used by accessing the internet www.ncbi.nlm.nih.gov/blast.

The antibody of the present invention may be an antibody competing with mouse antibody 1A3 or rabbit chimeric antibody 1A3 for the recognition property to a drug moiety of the antibody-drug conjugate according to the present invention.

The antibodies obtained by the method as mentioned above are evaluated on the recognition property to a drug moiety of the antibody-drug conjugate according to the present invention. In this manner, a suitable antibody can be selected. As another index for comparing characteristics of antibodies, stability of an antibody can be exemplified. Differential scanning calorimetry (DSC) is a method quickly and accurately measuring the transition midpoint temperature (Tm) serving as a good index for relative stability of a protein structure. Difference in thermal stability can be compared by measuring Tm values by DSC and comparing them. It is known that the storage stability of an antibody shows correlation with the thermal stability of the antibody to some extent (Lori Burton, et. al., Pharmaceutical Development and Technology (2007) 12, p. 265-273). A suitable antibody can be selected based on the thermal stability as an index. Another index for selecting an antibody, high yield in an appropriate host cell and low cohesiveness in an aqueous solution can be exemplified. Since the antibody most highly produced does not always have high thermal stability, it is necessary to select the most suitable antibody by comprehensive judgment based on the aforementioned indicators.

A method for obtaining a single chain immunoglobulin by connecting the full length sequences of a heavy chain and a light chain of an antibody by use of an appropriate linker is known (Lee, H-S, et al., Molecular Immunology (1999) 36, p. 61-71, Shirrmann, T. et al., mAbs (2010), 2, (1) p. 1-4). If such a single-strand immunoglobulin is dimerized, an analogous structure and activity to those of an antibody, which is basically a tetramer, can be obtained. The antibody of the present invention may be an antibody having a single heavy chain variable region and no light chain sequence. Such an antibody, which is called as a single domain antibody (sdAb) or a nanobody, is actually found in camels or llamas and reported to have an antigen binding ability (Muyldemans S. et al., Protein Eng. (1994) 7 (9), 1129-35, Hamers-Casterman C. et al., Nature (1993) 363 (6428) 446-8). The above antibody can be interpreted as an antigen binding fragment of the antibody of the present invention.

If an antibody is produced by once isolating an antibody gene and then, introducing it in an appropriate host, an appropriate combination of a host and an expression vector can be used. As an example of the antibody gene, an antibody gene having a gene encoding a heavy chain sequence of an antibody described in the specification and a gene encoding a light chain sequence in combination can be exemplified. If a host cell is transformed, the gene having a heavy chain sequence and the gene having a light chain sequence can be inserted in the same expression vector or in different expression vectors. If a eukaryotic cell is used as a host, animal cells, plant cells and eukaryotic microbes can be used. Examples of the animal cells include (1) mammalian cells, for example, monkey cells such as COS cells (Gluzman, Y. Cell (1981) 23, p. 175-182, ATCC CRL-1650), mouse fibroblasts NIH3T3 (ATCC No. CRL-1658) and Chinese hamster ovary cells (CHO cell, ATCC CCL-61) dihydrofolate reductase deficient strain (Urlaub, G. and Chasin, L. A. Proc. Natl. Acad. Sci. U.S.A. (1980) 77, p. 4126-4220). If a prokaryotic cell is used, for example, *E. coli* and *Bacillus subtilis* can be exemplified. An antibody is obtained by introducing a desired antibody gene into these cells through transformation and culturing a transformant in vitro. In the following culture method, the yield differs depending on the sequence of the antibody. An antibody easily produced as a medicine can be selected based on the yield as an index from antibodies having equivalent binding activity.

Isotypes of the antibody of the present invention are not limited, for example, IgG (IgG1, IgG2, IgG3, IgG4), IgM, IgA (IgA1, IgA2), IgD or IgE can be exemplified. Preferably, IgG or IgM, further preferably, IgG1 or IgG2 can be exemplified.

The antibody of the present invention may be an antigen binding fragment of the antibody having an antigen binding site of the antibody or a modified fragment thereof. The fragment of an antibody can be obtained by treating the antibody with a protease such as papain or pepsin or modifying an antibody gene by a genetic engineering method and expressing the modified gene in appropriate culture cells. Of these antibody fragments, a fragment having all or part of function of the full-length antibody molecule can be referred to as an antigen binding fragment of the antibody.

Examples of the antibody fragment include Fab, F(ab')2, Fv, a single-chain Fv (scFv) obtained by linking Fv of a heavy chain and a light chain via an appropriate linker, a diabody (diabodies), a linear antibody and a polyspecific antibody formed of antibody fragments. Also, Fab', which is a monovalent fragment of a variable region of an antibody obtained by treating F(ab')2 under reducing conditions, is included in antibody fragments.

The antibody of the present invention may be a polyspecific antibody having specificity to at least two types of antigens. Usually, such a molecule binds to two types of antigens (that is, bispecific antibody). The polyspecific antibody of the present invention includes antibodies having a specificity to two types or more antigens (for example, 3 types).

The polyspecific antibody of the present invention may be a full-length antibody or a fragment of the antibody (for example, F(ab')2 bispecific antibody). The bispecific antibody can be produced by connecting heavy chains and light chains (HL pairs) of two types of antibodies or fusing hybridomas cells producing different monoclonal antibodies to produce a bispecific antibody-producing fusion cell (Millstein et al., Nature (1983) 305, p. 537-539).

The antibody of the present invention may be a single-chain antibody (also referred to as scFv). The single-chain antibody is obtained by connecting a heavy chain variable region and a light chain variable region via a polypeptide linker (Pluckthun, The Pharmacology of Monoclonal Antibodies, 113 (edited by Rosenberg and Moore, Springer Verlag, New York, p. 269-315 (1994), Nature Biotechnology (2005), 23, p. 1126-1136). Alternatively, a BiscFv fragment produced by connecting two scFv via a polypeptide linker can be used as a bispecific antibody.

A method for producing a single-chain antibody is known in the technical field (see, for example, U.S. Pat. Nos. 4,946,778, 5,260,203, 5,091,513, 5,455,030). In the scFv, a heavy chain variable region and a light chain variable region are connected via a linker which will not form a conjugate, preferably, a polypeptide linker (Huston, J. S. et al., Proc. Natl. Acad. Sci. U.S.A. (1988), 85, p. 5879-5883). The heavy chain variable region and light chain variable region in an scFv may be derived from the same antibody or different antibodies. As the polypeptide linker connecting the variable regions, for example, a single-chain peptide consisting of 12 to 19 residues is used.

DNA encoding an scFv can be obtained as follows. Of DNA encoding a heavy chain or a heavy chain variable region of the antibody and DNA encoding a light chain or a light chain variable region, a DNA encoding a whole or a desired part of the amino acid sequence was selected. Using the DNA selected as a template, and a primer pair defining both ends thereof, PCR amplification is carried out. In addition, using DNA encoding a polypeptide linker portion in combination with a primer pair defining the both ends so as to be connected respectively to the heavy chain and light chain, amplification is carried out.

Once DNA encoding an scFv produced, an expression vector comprising DNA and a host transformed with the expression vector can be obtained in accordance with a customary method. Also, using the host, scFv can be obtained in accordance with a customary method. These antibody fragments can be produced in the same manner as above, that is, obtaining a gene and expressing the gene by use of a host.

The antibody of the present invention may be multimerized and enhanced in affinity to an antigen. The antibody to be multimerized may be a single type or a plurality of antibodies recognizing a plurality of epitopes of a same antigen. As a method for multimerizing an antibody, binding of an IgG CH3 domain and two scFvs, binding to streptavidin and introduction of a helix-turn-helix motif, etc., can be exemplified.

The antibody of the present invention may be polyclonal antibodies, which are a collection of a plurality of types of antibodies different in amino acid sequence. As polyclonal antibodies, for example, a collection of a plurality of types of antibodies different in CDR can be exemplified. As the polyclonal antibodies, a collection of cells producing different antibodies are cultured and antibodies purified from the culture can be used (see WO2004/061104).

For modifying an antibody, an antibody bound to various molecules such as polyethylene glycol (PEG) can be used.

The antibody of the present invention may be a conjugate (immunoconjugate) in which the antibody is conjugated to another drug. Examples of such an antibody include an antibody to be bound to a radioactive substance and a compound having a pharmacological action (Nature Biotechnology (2005) 23, p. 1137-1146).

4. Use of the Protein of the Present Invention

The protein of the present invention can be used in a detection method such as an ELISA (Enzyme-Linked ImmunoSorbent Assay) method, an ECL (Electrochemiluminescence) method, an RIA (Radio Immunoassay) method, an ELISPOT (Enzyme-Linked ImmunoSpot) method, a dot blot method, an octalony method, a CIE (Counterimmunoelectrophoresis) method, CLIA (Chemiluminescent immunoassay) and FCM (Flow Cytometry); and an immunohistochemistry (IHC) method, and preferably used in an ELISA method, an ECL method and an IHC method.

The ELISA and ECL methods may be used as a method for quantifying the concentration in plasma of an antibody-drug conjugate in a mammal (examples of the "mammal" in the present invention include, but are not limited to, a human, a mouse, a rat, a monkey and a rabbit) administered with the antibody-drug conjugate of the present invention.

More specifically, steps of: (1) contacting an antibody-drug conjugate contained in the plasma with a plate having the antigen of the antibody-drug conjugate immobilized thereon, to form a complex, (2) contacting the protein of the present invention labeled with a marker with the complex to form a further complex, and then, (3) detecting the marker, are included.

Also, the steps of: (1) contacting an antibody-drug conjugate contained in the plasma with a plate having the protein of the present invention immobilized thereon to form a complex, (2) contacting a second protein capable of recognizing an antibody moiety of the antibody-drug conjugate and labeled with a marker with the complex to form a further complex, and then, (3) detecting the marker can be included.

The ELISA and ECL methods can also be used as a method for quantifying the concentration in plasma of a drug (for example, compound (1), compound (2), compound (4) and compound (5)) released from the antibody-drug conjugate in a mammal administered with the antibody-drug conjugate of the present invention.

More specifically, the steps of: (1) contacting a drug released from an antibody-drug conjugate contained in the plasma with a plate having the protein of the present invention immobilized thereon, in the presence of a competitive drug labeled with a marker to form a complex and (2) detecting the marker are included.

The IHC method can be used as a method for determining the tissue distribution of the antibody-drug conjugate and/or a drug released from the antibody-drug conjugate, for example, in a mammal administered with the antibody-drug conjugate of the present invention.

More specifically, the steps of: (1) contacting the antibody-drug conjugate and/or a drug released from the antibody-drug conjugate in a tissue with the protein of the present invention to form a complex, (2) contacting a second protein capable of recognizing the protein of the present invention and labeled with a marker with the complex to form a further complex, and then, (3) detecting the marker are included.

Also, the steps of: (1) contacting the antibody-drug conjugate and/or a drug released from the antibody-drug conjugate in a tissue with the protein of the present invention labeled with a marker to form a complex, and then, (2) detecting the marker can be included.

In the present invention, the "marker" refers to a substance generating a detectable signal or a substance acting on another substance to generate a detectable signal. Examples of the marker include a fluorescent substance, an enzyme, an enzyme fragment, an enzyme substrate, an enzyme inhibitor, a coenzyme, a catalyst, a dye, a light-emitting material, a sensitizer and a radioactive substance.

In the present invention, the phrase "labeled with a marker" means that a marker is connected directly or with a partial structure (for example, a linker) interposed between them. Connection using interaction between a biotin and an avidin (or streptavidin) is included in labeling.

In order to label the protein of the present invention with a marker, for example, a reagent (having an active ester group) having a marker as a component is reacted with a lysine residue of the protein of the present invention to form an amide bond; however, the labeling method is not limited to this.

If the marker is a fluorescent substance, the marker can be detected by sensing fluorescence of the marker.

Examples of the fluorescent substance include DyLight (registered trademark) 350, DyLight (registered trademark) 405, DyLight (registered trademark) 488, DyLight (registered trademark) 550, DyLight (registered trademark) 594, DyLight (registered trademark) 633, DyLight (registered trademark) 650, DyLight (registered trademark) 680, DyLight (registered trademark) 747, DyLight (registered trademark) 755, DyLight (registered trademark) 800, Alexa Fluor (registered trademark) 350, Alexa Fluor (registered trademark) 405, Alexa Fluor (registered trademark) 488, Alexa Fluor (registered trademark) 532, Alexa Fluor (registered trademark) 546, Alexa Fluor (registered trademark) 555, Alexa Fluor (registered trademark) 568, Alexa Fluor (registered trademark) 594, Alexa Fluor (registered trademark) 647, Alexa Fluor (registered trademark) 680, Alexa Fluor (registered trademark) 750, BODIPY (registered trademark) FL, Coumarin, Cy (registered trademark) 3, Cy (registered trademark) 5, Cy (registered trademark), Fluorescein (FITC) Oregon Green (registered trademark), Pacific Blue, Pacific Green, Pacific Orange, Tetramethylrhodamine (TRITC) and Texas Red (registered trademark).

Also, nanocrystals such as Qdot (registered trademark) 525, Qdot (registered trademark) 565, Qdot (registered trademark) 605, Qdot (registered trademark) 655, Qdot (registered trademark) 705 and Qdot (registered trademark) 800 and fluorescent proteins such as Allophycocyanin (APC), R-Phycoerythrin (R-PE), Cyan Fluorescent Protein (CFP), Green Fluorescent Protein (GFP) and Red Fluorescent Protein (RFP) can be used as a fluorescent substance.

If the marker is an enzyme, the marker is detected by sensing light or color developed by a reaction between the enzyme and a substrate.

As the enzyme, for example, peroxidase (for example, horseradish peroxidase; HRP etc.,) can be exemplified. In this case, as a substrate of the enzyme, for example, TMB (3,3',5,5'-tetramethylbenzidine), DAB (3,3'-diaminobenzidine tetrahydrochloride), OPD (o-phenylenediamine) and ABTS (3-ethylbenzothiazoline-6-sulfonic acid) can be exemplified.

As another enzyme, alkaline phosphatase can be exemplified. In this case, as a substrate for the enzyme, for example, BCIP (5-bromo-4-chloro-3-indolyl phosphate) and PNPP (p-nitrophenyl phosphate) can be exemplified.

As another enzyme, luciferase can be exemplified. In this case, as a substrate for the enzyme, for example, Luciferin and Coelenterazine can be exemplified.

As another enzyme, β-galactosidase can be exemplified. In this case, as a substrate for the enzyme, for example, o-nitrophenyl-β-D-galactopyranoside (ONPG) can be exemplified.

If the marker is a light-emitting material, the marker is detected by sensing luminescence from the marker based on an electrochemical reaction.

As the light-emitting material, for example, a ruthenium complex, preferably a ruthenium-pyridine complex, and more preferably, ruthenium (II) tris(bipyridyl) complex can be exemplified.

The electrochemical reaction can be carried out in the presence of, for example, tripropylamine (TPA). More specifically, a TPA cation radical and a trivalent ruthenium complex are produced by an electrode reaction. The TPA cation radical immediately loses a hydrogen ion into a TPA radical having a strong reduction action, which reacts with a trivalent ruthenium complex to emit light.

If the marker is a radioactive substance, the marker is detected by sensing radiation emitted from the marker.

Examples of the radioactive substance include tritium ($^{3}$H), carbon-14 ($^{14}$C), nitrogen-15 ($^{15}$N), sulfur-35 ($^{35}$S), yttrium-90 ($^{90}$Y), technetium-99 ($^{99}$Tc), indium-111 ($^{111}$In), iodine-125 ($^{125}$I) and iodine-131 ($^{131}$I)

The protein of the present invention may be used as a component of a composition (hereinafter referred to as "the composition of the present invention") formed by adding a pH buffer, an osmotic pressure regulator, a salt, a stabilizer, a preservative, a developer, a sensitizer and an anticoagulant, etc.

The protein of the present invention (or the composition of the present invention) can be used as a component of a kit comprising materials and reagents for assay in combination (hereinafter referred to as "the kit of the present invention"). The reagents can be provided in a liquid or lyophilized state, in a same container or different containers depending on the degree of stability. The amounts and the ratio of the reagents provided in the kit of the present invention can be selected such that optimal results can be provided for the specific use. The kit of the present invention may contain, other than the protein of the present invention (or the composition of the present invention), for example, a reagent for attaching a marker, a substrate for an enzyme, a blocking reagent, a polymer reagent, an antigen activation solution, a calibrator, a dilution buffer, a washing buffer, an immobilization buffer, an immobilized antibody, a detection antibody and microtiter wells etc. In addition, instructions for using the kit of the present invention may be contained. Using the kit, the tissue distribution of the antibody-drug conjugate and/or a drug released from the antibody-drug conjugate can be confirmed and plasma-concentration, etc., can be quantified.

EXAMPLES

The present invention will be specifically described by way of the examples shown below. However, the present invention is not limited to these. These examples should not be interpreted as limiting the invention in any way. Note that, unless otherwise specified, individual operations regarding to gene manipulation in the following Examples were carried out in accordance with the methods described in "Molecular Cloning" (written by Sambrook, J., Fritsch, E. F. and Maniatis, T., published by Cold Spring Harbor Laboratory Press, in 1989) or in accordance with the instructions attached to commercially available reagents and kits if they were employed. In the specification, the reagents, solvents and starting materials not specified can be easily obtained from commercial sources.

41

[Example 1] Synthesis of compound i) Synthesis of 8-[(2,5-dioxopyrrolidin-1-yl)oxy]-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)-8-oxooctane Amide
(Compound (6))

[Formula 26]

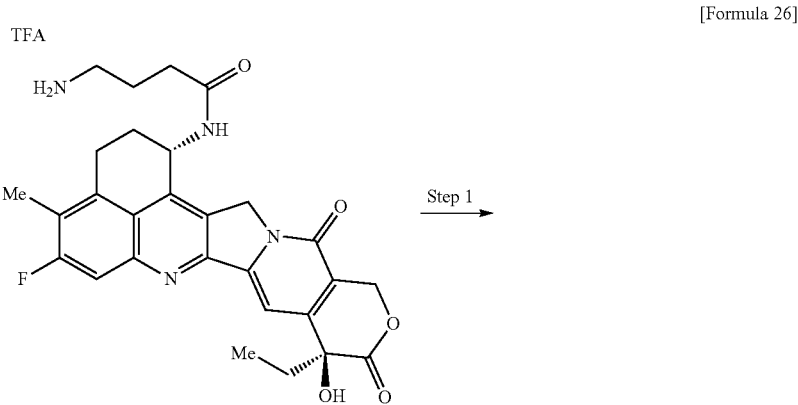

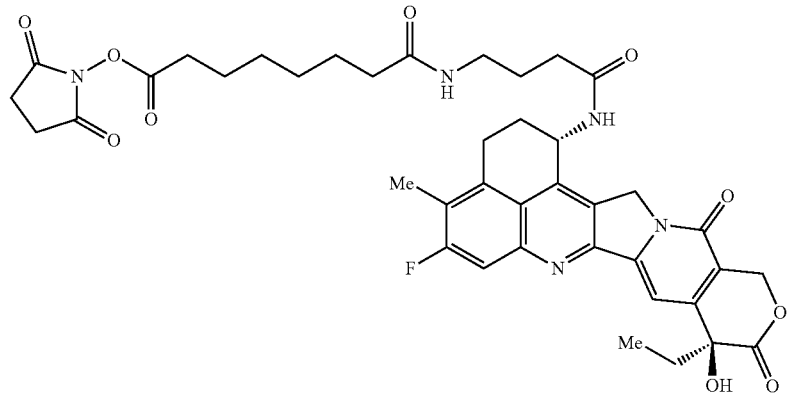

To a N,N-dimethylformamide (0.5 mL) solution of 4-amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]butanamide (0.032 g, 0.050 mmoL) (compound obtained in Step 2 of Example 1 described in International Publication No. WO 2014/057687), triethylamine (7 µL, 0.050 mmoL) and di(N-succinimidyl) suberate (20.4 mg, 0.055 mmoL) were added. The reaction solution was stirred for 20 minutes at room temperature. The solvent was evaporated under reduced pressure. The obtained residue was purified by silica gel column chromatography [chloroform-chloroform: methanol=9:1 (v/v)] to obtain the title compound (16.0 mg, 41%) as a light yellow solid.

$^1$H-NMR (400 MHz, DMSO-$d_6$) δ: 0.87 (3H, t, J=7.6 Hz), 1.18-1.37 (4H, m), 1.40-1.50 (2H, m), 1.54-1.64 (2H, m), 1.65-1.74 (2H, m), 1.78-1.93 (2H, m), 2.02 (2H, t, J=7.6 Hz), 2.09-2.20 (4H, m), 2.40 (3H, s), 2.60-2.68 (2H, m), 2.80 (4H, s), 3.00-3.08 (2H, m), 3.13-3.21 (2H, m), 5.19 (2H, dd, J=32.0, 18.0 Hz), 5.37-5.47 (2H, m), 5.53-5.60 (1H, m), 6.52 (1H, s), 7.30 (1H, s), 7.74-7.82 (2H, m), 8.44 (1H, d, J=8.5 Hz).

MS (APCI) m/z: 774 (M+H)$^+$ ii) Synthesis of 4-amino-N-[(1S,9S)-9-ethyl-5-fluoro-9,10-dihydroxy-4-methyl-13-oxo-2,3,9,10,13,15-hexahydro-1H,12H-benzo[de]pyrano[3',4':6,7]indolizino[1,2-b]quinolin-1-yl] butanamide Trifluoroacetate (Compound (7))

[Formula 27]

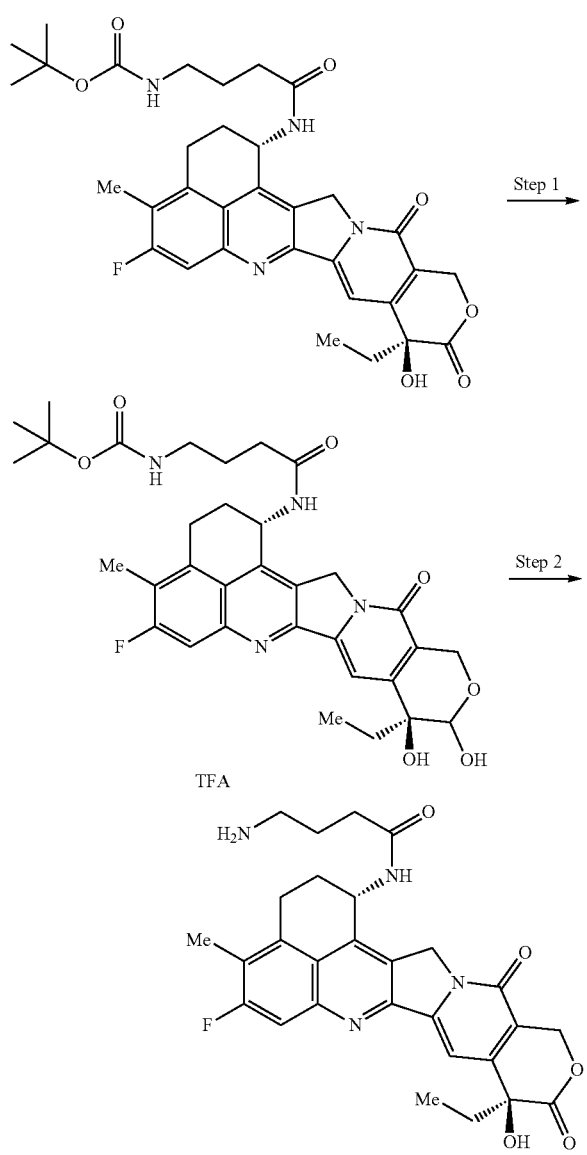

Step 1:
First, tert-butyl(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl) carbamate (0.092 g, 0.148 mmoL) (compound obtained in Step 1 of Example 1 described in International Publication No. WO 2014/057687) was dissolved in methanol (1.6 mL) and cooled on ice. To this, sodium borohydride (0.028 g, 0.740 mmoL) was added and the reaction solution was stirred for 20 minutes under ice cooling. The solution was diluted with methanol (10 mL) and chloroform (50 mL) and a 10% aqueous citric acid solution was added thereto, and then, extracted with chloroform. The obtained organic layer was washed with a 10% aqueous citric acid solution followed by a saturated saline solution, dried over sodium sulfate and filtered. The solvent was evaporated under reduced pressure. The obtained residue was purified by silica gel column chromatography-[chloroform: methanol=100: 0-95:5 (v/v)] to obtain tert-butyl(4-{[(1S,9S)-9-ethyl-5-fluoro-9-hydroxy-4-methyl-13-oxo-2,3,9,10,13,15-hexahydro-1H,12H-benzo[de]pyrano[3',4':6,7]indolizino[1,2-b]quinolin-1-yl]amino}-4-oxobutyl) carbamate (0.078 g, 85%) as a light yellow solid.

$^1$H-NMR (400 MHz, DMSO-$d_6$) δ: 0.89 (3H, t, J=7.4 Hz), 1.31 (9H, s), 1.62-1.73 (4H, m), 2.08-2.18 (4H, m), 2.39 (3H, s), 2.91 (2H, q, J=6.5 Hz), 3.12-3.20 (2H, m), 4.49 (1H, d, J=17.2 Hz), 4.61 (1H, d, J=17.2 Hz), 4.97 (1H, s), 4.99 (1H, d, J=4.7 Hz), 5.10 (2H, d, J=18.8 Hz), 5.21 (2H, d, J=18.8 Hz), 5.54-5.58 (1H, m), 6.74-6.82 (2H, m), 7.33 (1H, s), 7.78 (1H, d, J=11.0 Hz), 8.40 (1H, d, J=8.6 Hz).

Step 2:
The compound (0.078 g, 0.125 mmoL) obtained in Step 1 above was added to dichloromethane (2 mL). The reaction solution was cooled on ice and trifluoro acetate (2 mL) was added. The reaction solution was stirred for 40 minutes. The solvent was evaporated under reduced pressure. The obtained residue was purified by silica gel column chromatography [chloroform-organic layer having a distribution ratio of chloroform: methanol: water=7:3:1 (v/v/v)]. The obtained solid was dissolved in methanol and ether was added. The resultant precipitation was filtered and dried under vacuum to obtain the title compound (0.045 g, 56%) as a yellow-solid.

$^1$H-NMR (400 MHz, DMSO-$d_6$) δ: 0.89 (3H, t, J=7.4 Hz), 1.71 (2H, q, J=7.4 Hz), 1.80-1.88 (2H, m), 2.09-2.19 (2H, m), 2.27 (2H, t, J=7.0 Hz), 2.40 (3H, s), 2.84 (2H, t, J=7.6 Hz), 3.13-3.20 (2H, m), 4.50 (1H, d, J=17.2 Hz), 4.62 (1H, d, J=17.2 Hz), 4.97-5.02 (2H, m), 5.09 (1H, d, J=18.8 Hz), 5.21 (1H, d, J=18.8 Hz), 5.55-5.59 (1H, m), 6.79 (1H, d, J=4.7 Hz), 7.34 (1H, s), 7.64-7.75 (3H, m), 7.79 (1H, d, J=11.3 Hz), 8.53 (1H, d, J=8.6 Hz).

MS (APCI) m/z: 523 (M+H)$^+$ iii) Synthesis of 4-amino-N-cyclohexyl-butanamide Hydrochloride (Compound (8))

[Formula 28]

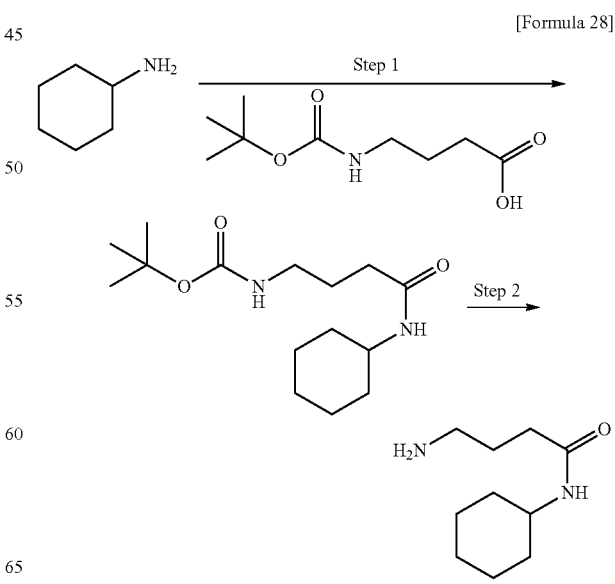

Step 1:

First, 4-(tert-butoxycarbonylamino)butanoic acid (0.492 g, 2.42 mmoL) was dissolved in dichloromethane (15 mL) and N,N-dimethylformamide (2 mL), and then, N-hydroxysuccinimide (0.279 g, 2.42 mmoL) and EDCI (1-ethyl-3-(3-dimethylaminopropyl) carbodiimide hydrochloride) (0.464 g, 2.42 mmoL) were added. The reaction solution was stirred at room temperature for 30 minutes. The reaction solution was added dropwise to a dichloromethane solution (2 mL) of cyclohexylamine (0.200 g, 2.02 mmoL) and stirred at room temperature for 20 minutes. The reaction solution was diluted with dichloromethane and a 10% aqueous citric acid solution was added, and then, extracted with dichloromethane. The obtained organic layer was washed with a saturated sodium bicarbonate solution, dried over sodium sulfate and filtered. The solvent was evaporated under reduced pressure. The obtained residue was purified by silica gel column chromatography-[hexane: ethyl acetate=50: 50-25:75 (v/v)] to obtain tert-butyl N-[4-(cyclohexylamino)-4-oxo-butyl]carbamate (0.308 g, 54%) as a colorless-oil.

$^1$H-NMR (400 MHz, CDCl$_3$) δ: 1.08-1.23 (4H, m), 1.29-1.42 (2H, m), 1.44 (9H, s), 1.66-1.75 (2H, m), 1.77-1.83 (2H, m), 1.86-1.95 (2H, m), 2.17 (2H, t, J=7.0 Hz), 3.11-3.21 (2H, m), 3.69-3.82 (1H, m), 4.75 (1H, brs), 5.89 (1H, brs).

Step 2:

The compound (0.200 g, 0.703 mmoL) obtained in Step 1 above was dissolved in ethyl acetate (50 mL) and dioxane (10 mL). A 4N dioxane hydrochloride (10 mL) was added and the mixture was stirred for two hours. The precipitation generated was filtered, dried under vacuum to obtain the title compound (0.098 g, 63%) as a colorless solid.

$^1$H-NMR (400 MHz, DMSO-d$_6$) δ: 1.06-1.30 (5H, m), 1.50-1.58 (1H, m), 1.62-1.82 (6H, m), 2.16 (2H, t, J=7.2 Hz), 2.69-2.79 (2H, m), 3.45-3.58 (1H, m), 4.73 (1H, brs), 7.89 (1H, d, J=7.8 Hz), 7.96-8.10 (2H, m).

MS (APCI) m/z: 185 (M+H)$^+$

[Example 2] Production of Antibody-Drug Conjugate i) Production (1) of Anti-B7-H3 Antibody-Drug Conjugate In accordance with the production method described in International Publication No. WO 2014/057687 and using an anti-B7-H3 antibody (antibody comprising a heavy chain consisting of the amino acid sequence consisting of amino acid residues 20 to 471 of SEQ ID NO: 27 and a light chain consisting of the amino acid sequence consisting of amino acid residues 21 to 233 of SEQ ID NO: 28), an anti-B7-H3 antibody-drug conjugate, in which a drug-linker represented by the following formula:

[Formula 29]

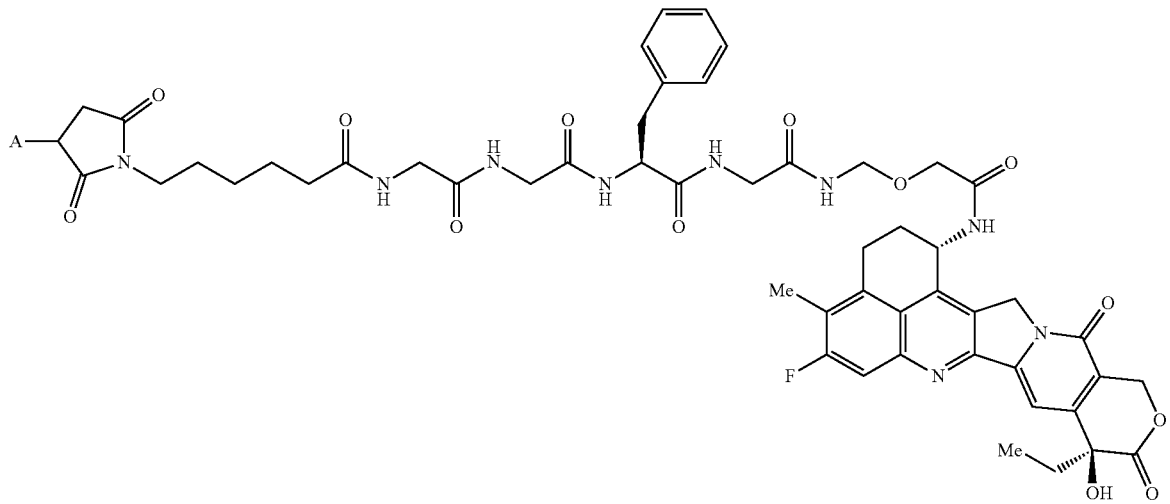

wherein A represents a connecting position to the antibody, is conjugated to the anti-B7-H3 antibody via a thioether bond (referred to as "B7-H3-ADC (I)" in the present invention), was produced.

ii) Production (2) of Anti-B7-H3 Antibody-Drug Conjugate

In accordance with the production method described in International Publication No. WO 2014/057687, and using an anti-B7-H3 antibody (antibody comprising a heavy chain consisting of the amino acid sequence consisting of amino acid residues 20 to 471 of SEQ ID NO: 27 and a light chain consisting of the amino acid sequence consisting of amino acid residues 21 to 233 of SEQ ID NO: 28), an anti-B7-H3 antibody-drug conjugate, in which a drug-linker represented by the following formula:

[Formula 30]

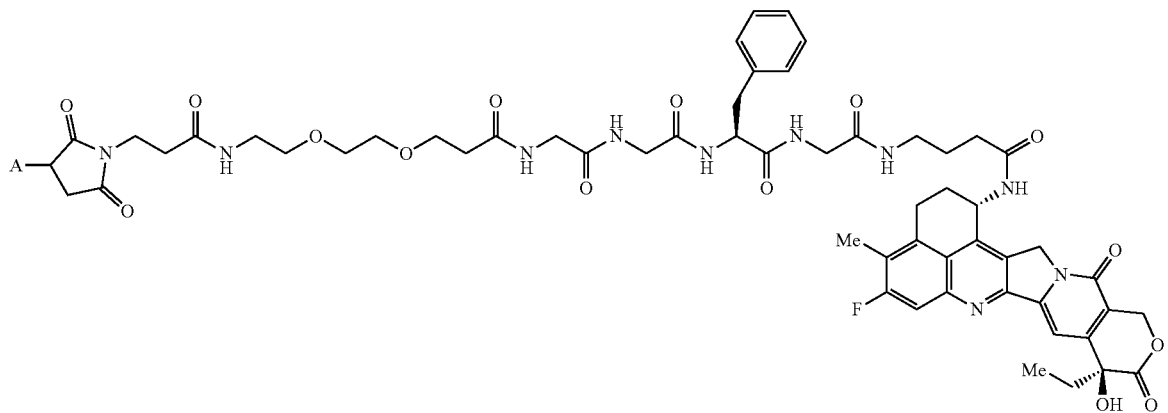

wherein A represents a connecting position to the antibody, is conjugated to the anti-B7-H3 antibody via a thioether bond (referred to as "B7-H3-ADC (II)" in the present invention), was produced.

iii) Production (3) of Anti-B7-H3 Antibody-Drug Conjugate

In accordance with the production method described in International Publication No. WO 2014/057687, and using an anti-B7-H3 antibody (antibody comprising a heavy chain consisting of the amino acid sequence consisting of amino acid residues 20 to 471 of SEQ ID NO: 27 and a light chain consisting of the amino acid sequence consisting of amino acid residues 21 to 233 of SEQ ID NO: 28), an anti-B7-H3 antibody-drug conjugate, in which a drug-linker represented by the following formula:

[Formula 31]

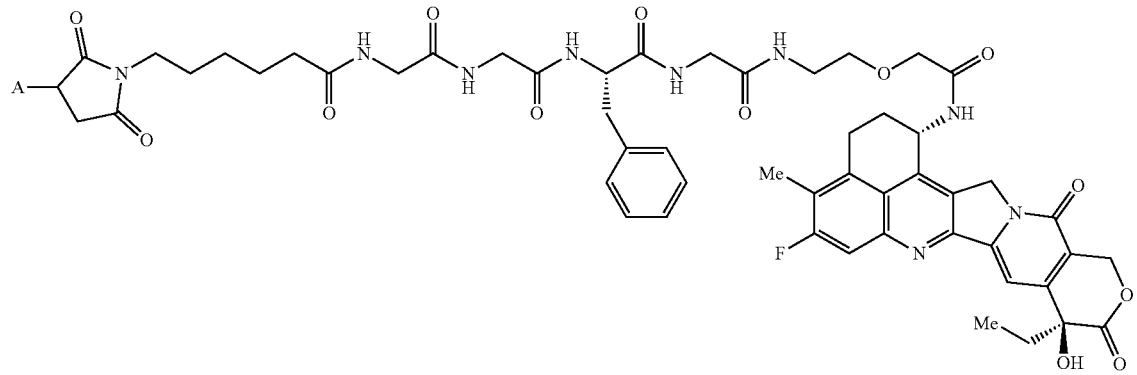

wherein A represents a connecting position to the antibody, is conjugated to the anti-B7-H3 antibody via a thioether bond (referred to as "B7-H3-ADC (III)" in the present invention), was produced.

iv) Production (1) of Anti-HER2 Antibody-Drug Conjugate

In accordance with the production method described in International Publication No. WO 2015/115091 and using an anti-HER2 antibody (antibody comprising a heavy chain consisting of the amino acid sequence consisting of amino acid residues 1 to 449 of SEQ ID NO: 21 and a light chain consisting of the amino acid sequence consisting of amino acid residues 1 to 214 of SEQ ID NO: 22), an anti-HER2 antibody-drug conjugate, in which a drug-linker represented by the following formula:

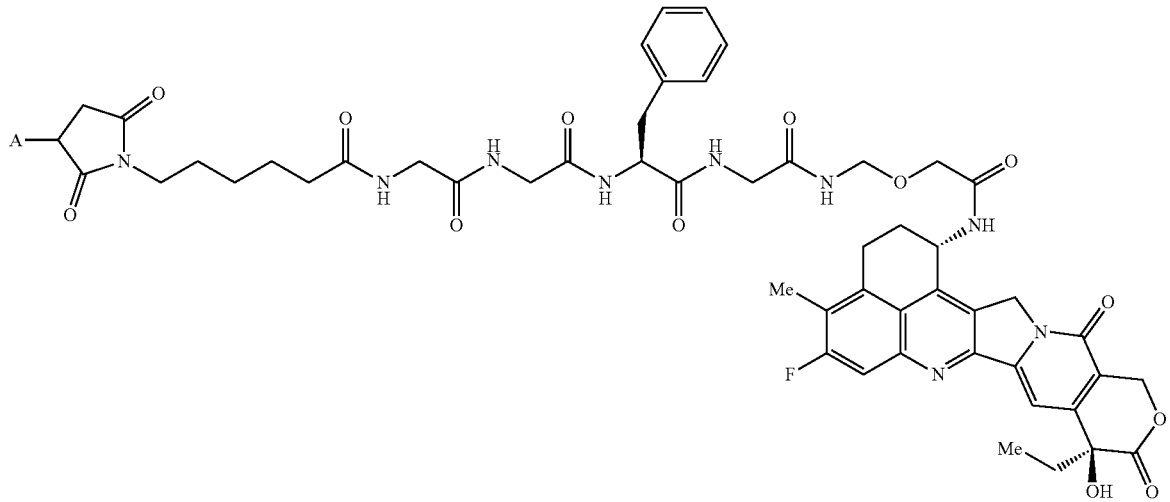

wherein A represents a connecting position to the antibody, is conjugated to the anti-HER2 antibody via a thioether bond (referred to as "HER2-ADC (I)" in the present invention), was produced.

v) Production (1) of Anti-HER3 Antibody-Drug Conjugate

In accordance with the production method described in International Publication No. WO 2015/155998, and using an anti-HER3 antibody (antibody comprising a heavy chain consisting of the amino acid sequence represented by SEQ ID NO: 23 and a light chain consisting of the amino acid sequence represented by SEQ ID NO: 24), an anti-HER3 antibody-drug conjugate, in which a drug-linker represented by the following formula:

wherein A represents a connecting position to the antibody, is conjugated to the anti-HER3 antibody via a thioether bond (referred to as "HER3-ADC (I)" in the present invention), was produced.

vi) Production (1) of Anti-TROP2 Antibody-Drug Conjugate

In accordance with the production method described in International Publication No. WO 2015/098099, and using an anti-TROP2 antibody (antibody comprising a heavy chain consisting of the amino acid sequence consisting of amino acid residues 20 to 470 of SEQ ID NO: 25 and a light chain consisting of the amino acid sequence consisting of amino acid residues 21 to 234 of SEQ ID NO: 26), an anti-HER3 antibody-drug conjugate, in which a drug-linker represented by the following formula:

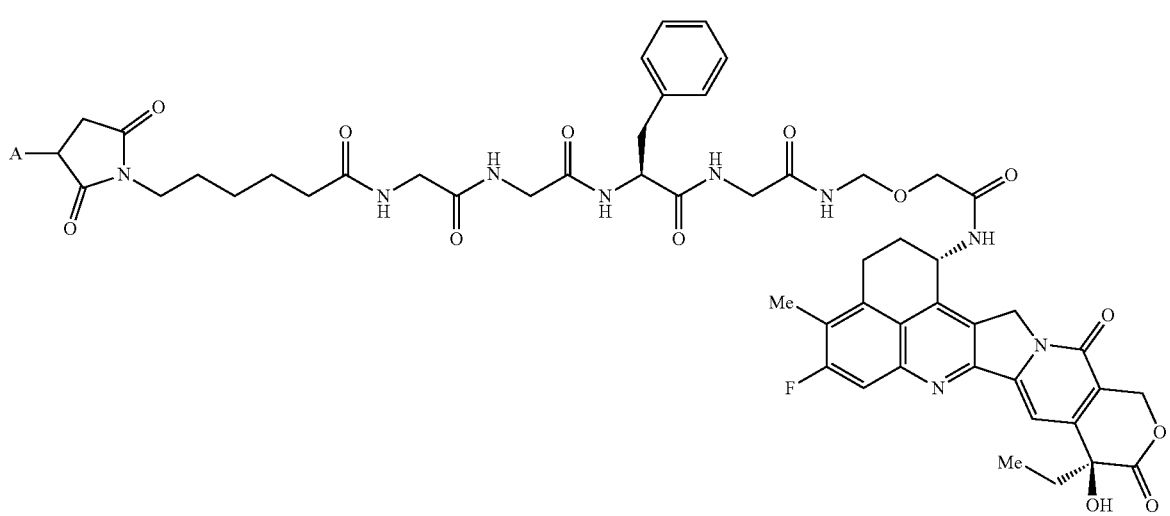

[Formula 34]

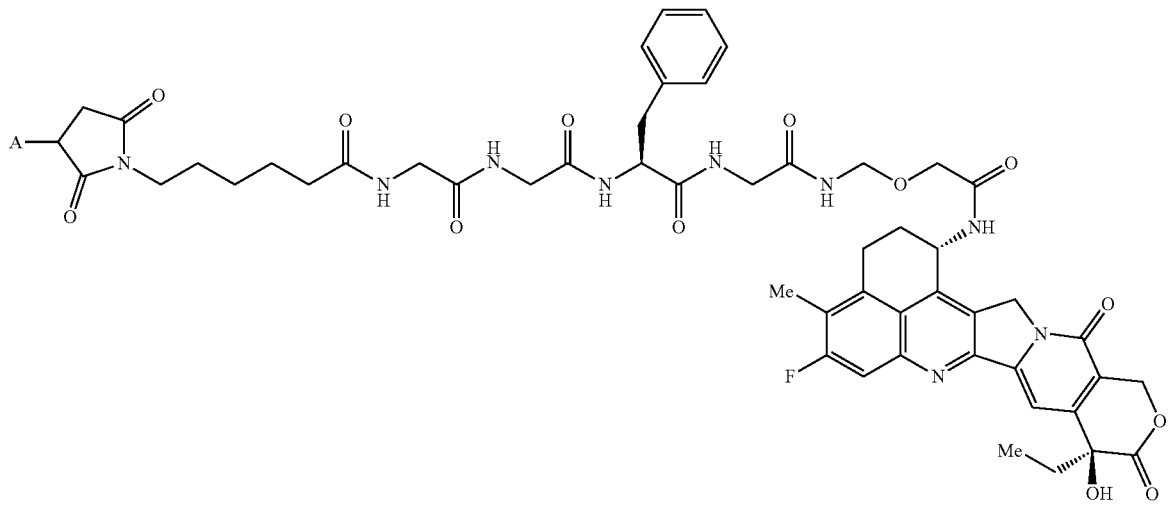

wherein A represents a connecting position to the antibody, is conjugated to the anti-TROP2 antibody via a thioether bond (referred to as "TROP2-ADC (I)" in the present invention), was produced.

[Example 3] Production of Monoclonal Antibody i) Preparation of Antigen Protein

As the antigen protein, an antigen protein (hereinafter referred to as "antigen protein (1)") prepared by adding bovine thyroglobulin serving as a carrier protein to compound (6) and an antigen protein (hereinafter referred to as "antigen protein (2)") prepared by adding BSA to compound (6), were used.

ii) Immunization

In immunization, BALB/cAnNCrlCrlj (BALB/c) mice (4 individuals) and B6D2F1/Crlj (BDF1) female mice (4 individuals) (Charles River Laboratories Japan Inc.) were used. At the initial immunization, a mixture of the antigen protein (1) and Freund's Complete Adjuvant (manufactured by Wako Pure Chemical Industries Ltd.) was subcutaneously and intradermally administered. On and after the second immunization, a mixture of the antigen protein (1) and Freund's Incomplete Adjuvant (manufactured by Wako Pure Chemical Industries Ltd.) was subcutaneously and intradermally administered. Administration was carried out at the intervals of 7 days, 4 times in total.

iii) Evaluation of Antibody Titer of Antiserum

Before immunization and after immunization through four administrations, the sera of BALB/c mice (4 individuals) and BDF1 mice (4 individuals) were each diluted up to 200 to 204800 fold. The antibody titers of the dilutions were checked using the antigen protein (2) and B7-H3-ADC (II) as positive controls and BSA as a negative control. The antigen protein (2), B7-H3-ADC (II) and BSA were immobilized to ELISA immunoplates. Diluted mouse sera before immunization and after immunization through four administrations were allowed to react with the immunoplates at 37° C. for 30 minutes. After washing, horseradish peroxidase-conjugated anti-mouse IgG (anti-mouse IgG-HRP) was allowed to react at 37° C. for 30 minutes. After washing, an o-phenylenediamine dihydrochloride (OPD) solution was added. After termination of color development, the absorbance at 490 nm was measured. It was confirmed that antibody titer to a positive control increases in all individuals.

iv) Inhibition ELISA

To the sera of BALB/c mice (4 individuals) and BDF1 mice (4 individuals) after immunization through four administrations, compound (6), compound (7) and compound (1) as positive controls and compound (8) as a negative control were added and the unabsorption rate to antigen protein (2) was calculated. The mouse sera diluted to 50000 fold and compound (6), compound (8), compound (7) and compound (1), which were prepared to have a concentration of 12.5, 25, 50 and 100 µg/mL, were mixed and allowed to react at 4° C. overnight, and then, added to ELISA immunoplates having the antigen protein (2) immobilized thereon and allowed to react at 37° C. for 30 minutes. After washing, anti-mouse IgG-HRP was allowed to react at 37° C. for 30 minutes. After washing, an OPD solution was added. After termination of color development, absorbance at 490 nm was measured. The unabsorption rate was calculated in accordance with the following expression:

Unabsorption rate(%)=(a/b)×100 a: Absorbance of positive control or negative control at an addition concentration of 12.5 µg/mL b: Absorbance of a sample not containing positive control or a sample not containing a negative control In any one of mouse sera, it was found that compound (6) and compound (1) as positive controls, and compound (7) in some individuals have a high inhibition effect. However, in none of the plasmas, a high inhibition effect on compound (8) as a negative control was found. From each of the BALB/c mice and BDF1 mice having sera exhibiting a high inhibition effect on compound (7) and no high inhibition effect on compound (8), an individual was selected. The lymph node and spleen were taken from each of the individuals and used for production of hybridomas.

v) Production of Hybridoma

Lymph node cells and spleen cells taken from individuals selected in iv) and mouse myeloma cells were fused by the PEG method. Using the culture supernatant of the emergent hybridoma cells, antibody-producing hybridoma cells were screened.

vi) Evaluation of Specific Binding to Antigen Protein (2)

The antigen protein (2) was immobilized to an ELISA immunoplate and the supernatant of antibody-producing hybridoma cells cultured was diluted double and allowed to react at 37° C. for 120 minutes. After washing, anti-mouse IgG-HRP was allowed to react at 37° C. for 30 minute. After washing, an OPD solution was added. After termination of color development, absorbance at 490 nm was measured. Eleven hybridoma strains producing a culture supernatant showing an OD value of 0.2 or more were elected as a positive.

vii) Cross Check

The 11 strains selected as a positive in vi) were subjected to inhibition ELISA using compound (6), compound (1), B7-H3-ADC (II), B7-H3-ADC (I) and B7-H3-ADC (III) as a positive control, and compound (8) and compound (7) as a compound for confirming whether a reaction proceeds or not. The culture supernatants of 11 strains selected as a positive and obtained in vi) were diluted double. To each of the culture supernatants, a positive control as mentioned above and the compound for confirming whether a reaction proceeds or not were added so as to obtain a final concentration of 25 µg/m. After a reaction was carried out at 4° C. overnight, the reaction solution was added to an ELISA immunoplate having the antigen protein (2) immobilized thereon and allowed to react at 37° C. for 30 minutes. After washing, anti-mouse IgG-HRP was allowed to react at 37° C. for 30 minutes. After washing, an OPD solution was added. After termination of color development, the absorbance at 490 nm was measured. Eight strains exhibiting high reactivity to the antigen protein (2) and confirmed to have an inhibition effect by the positive control were selected and subjected to primary cloning.

viii) Primary Cloning, Primary Screening

Eight strains selected in vii) were cloned by limiting dilution. Hybridomas were seeded so as to satisfy a rate of 60 cells/96 well plate and mouse thymocytes were added so as to satisfy a rate of 5×10$^6$ cells/well. Culture was carried out using a 10% FBS containing TIL (Immuno-Biological Laboratories Co., Ltd.). Inhibition ELISA was carried out in the same manner as in vii). Eight strains×6 subclones, which were confirmed to have specificity, were selected.

ix) Primary Cross Check

Eight strains×6 subclones selected in viii) were checked for reactivity to B7-H3-ADC (II) and B7-H3-ADC (I). B7-H3 C1 domain LotB7_OmJ1 was diluted with an immobilization buffer up to 1 µg/mL, added to Maxi-Sorp plates in a ratio of 100 µL per plate and allowed to immobilize at 4° C. overnight. The following day, the medium was removed from the plates and a 5% BSA-containing PBS was added in a ratio of 180 µL per plate. The plates were allowed to stand still at room temperature for 3 hours. After washing twice with 0.05% Tween20-containing PBS, B7-H3-ADC (II) and B7-H3-ADC (I), which were prepared to have a concentration of 0.1 µg/mL, were added in a ratio of 100 µL and allowed to stand still at room temperature for about one hour. After washing twice with 0.05% Tween20-containing PBS, 50 µL of the hybridoma supernatant serially diluted 7 times from 900 µg/mL at a common ratio of 3, was added per plate. The plates were allowed to stand still at room temperature for one hour. After washing twice with 0.05% Tween20-containing PBS, 100 µL of Peroxidase AffiniPure Goat Anti-Mouse IgG, Fcγ Fragment Specific (Jackson Immuno Research LABORATORIES, INC.) diluted 5000 fold, was added per plate. The plates were allowed to stand still at room temperature for one hour. After washing three times with 0.05% Tween20-containing PBS, 100 µL of a HRP substrate (OPD tablet) was added per plate and a color reaction was carried out. After the color reaction was terminated by adding 100 µL of 1M HCl per plate, absorbance at 450 nm was measured by ARVO (PerkinElmer). In all of 8 strains×6 subclones, reactivity to B7-H3-ADC (II) and B7-H3-ADC (I) was confirmed. Of them, 4 strains×6 subclones which were highly reactive were subjected to confirmation by the primary calibration curve.

x) Confirmation by Primary Calibration Curve

Four strains×6 subclones selected in ix) were checked for reactivity to B7-H3-ADC (I) (DAR7) and B7-H3-ADC (I) (DAR5) by ELISA. AffiniPure Goat Anti-Mouse IgG, Fcγ fragment specific (Jackson Immuno Research Inc.) was diluted with Coating Buffer up to 1 µg/mL and added to Maxi-Sorp plates in a ratio of 100 µL per plate, and then, allowed to immobilize at 4° C. overnight. The following day, the medium was removed from the plates. After washing with PBS, a 10% BSA-containing PBS was added in a ratio of 100 µL per plate. The plates were allowed to stand still at 37° C. for 2.5 hours. The medium was removed from the plates, hybridoma 4 strains x 6 subclones were diluted with 2% BSA and 0.2% Polysorbate20 (hereinafter referred to as "PS20") containing PBS up to 10, 25 and 100 ng/mL. Each of the dilutions was added to the plates in a ratio of 100 µL per plate. The plates were allowed to stand still at 37° C. for one hour. After washing four times with 0.05% PS20-containing PBS, B7-H3-ADC (I) (DAR7) and B7-H3-ADC (I) (DAR5) were diluted with 2% BSA, 0.2% Tween20-containing PBS up to 1, 2.5, 10, 25, 100 and 250 ng/mL. Each of the dilutions was added in a ratio of 100 µL per plate. The plates were allowed to stand still at 37° C. for one hour. After washing four times with a 0.05% PS20-containing PBS, Goat Anti-Human kappa-HRP (Southern Biotechnology Associates, Inc.) diluted with 2% BSA, 0.2% PS20-containing PBS up to 7500 fold was added in a ratio of 100 µL per plate. The plates were allowed to stand still at room temperature for one hour. After washing four times with a 0.05% PS20-containing PBS, TMB soluble reagent (ScyTek Laboratories) was added in a ratio of 100 µL/well and a color reaction was carried out. After the color reaction was terminated by adding TMB stop buffer (ScyTek Laboratories) in a ratio of 100 µL/well and absorbance (reference 650 nm) at 450 nm was measured by VersaMax (manufactured by Molecular Devices). Relative errors were calculated in accordance with the following expression and clones having small values were selected $$\text{Relative error}(\%) = \{(\text{measurement value DAR7})/(\text{measurement value of DAR5}) - 1\} \times 100$$

Of them, 4 strains x 2 subclones were subjected to secondary cloning.

xi) Secondary Cloning, Screening

Four strains x 2 subclones selected in x) were subjected to secondary cloning. Three wells were selected from the positive wells per clone. In this way, 24 clones in total were selected. Antibody titer to the antigen protein (2) was checked in the same manner as in vi). Further, using compound (6), compound (1), B7-H3-ADC (II), B7-H3-ADC (I) and B7-H3-ADC (III) as a positive control, and compound (8) and compound (7) as a compound for confirming whether a reaction proceeds or not, inhibition ELISA was carried out in the same manner as in vii).

xii) Confirmation by Secondary Calibration Curve

Of the 24 clones selected in xi), 6 clones exhibiting particularly high reactivity to compound (7) compared to compound (1) were eliminated. The remaining 18 clones were subjected to confirmation of reactivity to HER2-ADC (I) (DAR8), HER2-ADC (I) (DAR4) and HER2-ADC (I) (DAR2) and formation of calibration curves carried out by Gyrolab xP workstation (GYROS PROTEIN Technologies). As a capture reagent, Biotin-SP-conjugated AffiniPure Goat Anti-Mouse IgG, Fcγ specific (Jackson Immuno Research LABORATORIES, INC.) was used and the concentration thereof was controlled to be 172.5 nM with 0.01% PS20-containing PBS. The concentration of the cell culture supernatant was controlled with Rexxip CCS (GYROS PROTEIN Technologies) to be 200 ng/mL. HER2-ADC (I) (DAR8), HER2-ADC (I) (DAR4) and HER2-ADC (I) (DAR2) were serially diluted 6 times with 0.01% PS20-containing PBS from 1000 ng/mL at a common ratio of 4. As a detection reagent, Goat Anti Human kappa (Southern Biotechnology Associates, Inc.) was labeled using Alexa Fluor (registered trademark) 647 labeling kit (Thermo Fisher Scientific Inc.) and the concentration thereof was controlled to be 10 nM with Rexxip F. The reagents prepared above, cell culture supernatant and samples for a calibration curve were added in 96-well PCR plates and set together with Gyrolab Bioaffy 200 in a Gyrolab xP workstation. Measurement was carried out by 4-Step (2×C)-A-D (wizard method). Regression of the calibration curve was carried out in accordance with the 4-parameter logistic model (weight: Response) using Gyrolab Evaluator Software. All of the 18 clones evaluated did not depend on DAR of HER2-ADC (I) and no difference in reactivity between strains was recognized. Thus, three clones (1A3, 8B2, 11B1), which were derived from the same strain and had a high IgG concentration, were selected and subjected to a small-quantity production.

xiii) Preparation of Antibody Purified with Protein A and Cross Check

Three clones (1A3, 8B2, 11B1) selected in xii) were each cultured in a serum-free medium (ASF104 (N)) in a roller bottle. After the culture supernatant was collected, filtration by a 0.45 μm filter and purification by Protein A column were carried out. To ELISA immunoplates having antigen protein (2) immobilized in a ratio of 50 ng/well/50 μL, solutions (50 μL) containing the three clones purified with Protein A and serially diluted 10 times from 5 μg/mL at a common ratio of 2, were added and allowed to react at 37° C. for 30 minutes. After washing, anti-mouse IgG-HRP was allowed to react at 37° C. for 30 minutes. After washing, an OPD solution was added. After termination of color development, absorbance at 490 nm was measured. All antibodies purified with Protein A showed satisfactory reactivity with antigen protein (2).

xiv) Confirmation of Calibration Curve of Antibody Purified with Protein A

Reactivity of three clones (1A3, 8B2, 11B1) purified with protein A in xiii) to HER2-ADC (I) (DAR8) and HER2-ADC (I) (DAR4) and, B7-H3-ADC (I) (DAR8) and B7-H3-ADC (I) (DAR4) was checked by use of Gyrolab xP workstation.

As a capture reagent, the three clones purified with Protein A and labeled with EZ-Link NHS-LC-Biotin (Thermo Fisher Scientific Inc.) were used and the concentrations thereof were controlled with 0.01% PS20-containing PBS to be 700 nM. HER2-ADC (I) (DAR8) and HER2-ADC (I) (DAR4) were each serially diluted 6 times with Rexxip HN from 1000 ng/mL at a common ratio of 4. As the detection reagent used herein, Goat Anti Human kappa (Southern Biotechnology Associates, Inc.) which was labeled by use of Alexa Fluor (registered trademark) 647 labeling kit was used and the concentration thereof was controlled with Rexxip F to be 10 nM. The reagents prepared and an antibody-drug conjugate (sample for calibration curve) were added in 96-well PCR plates and set together with Gyrolab Bioaffy 200 in Gyrolab xP workstation. Measurement was carried out by 200-3W-001-A (wizard method). The regression of the calibration curve was carried out using 4-parameter logistic model (weighting; Response) and Gyrolab Evaluator Software. The calibration curve of clone 1A3 is shown in FIG. 15, the calibration curve of clone 8B2 in FIG. 16 and the calibration curve of clone 11B1 in FIG. 17. All clones showed reactivity to HER2-ADC (I) independently of DAR.

Further, as capture reagents, Human Her2/ErbB2 Protein (ACROBiosystems) labeled with EZ-Link NHS-LC-Biotin and B7-H3 C1 domain also labeled with the biotin were used. The concentrations of them were controlled with 0.01% PS20-containing PBS to be 700 nM. HER2-ADC (I) (DAR8) and HER2-ADC (I) (DAR4) and B7-H3-ADC (I) (DAR8) and B7-H3-ADC (I) (DAR4) were serially diluted 6 times with Rexxip HN from 1000 ng/mL in a common ratio of 4. As detection reagents, three clones (1A3, 8B2, 11B1) purified with Protein A and labeled using DyLight650 (registered trademark) labeling kit (Thermo Fisher Scientific Inc.) were used. The concentrations of them were controlled with Rexxip F to be 10 nM. The reagents prepared and samples for calibration curves of the antibody-drug conjugates were added in 96-well PCR plates, which were set together with Gyrolab Bioaffy 200 in Gyrolab xP workstation. Measurement was carried out by 200-3W-001-A (wizard method). Regression of the calibration curve was carried out in accordance with the 4-parameter logistic model (weighting; Response) by Gyrolab Evaluator Software. As to the reactivity to HER2-ADC (I), the calibration curve of clone 1A3 is shown in FIG. 18, the calibration curve of clone 8B2 in FIG. 19 and the calibration curve of clone 11B1 in FIG. 20. As to the reactivity to B7-H3-ADC (I), the calibration curve of clone 1A3 is shown in FIG. 21, the calibration curve of clone 8B2 in FIG. 22 and the calibration curve of clone 11B1 in FIG. 23. All clones showed reactivity to HER2-ADC (I) and B7-H3-ADC (I) independently of DAR.

From the results, it was confirmed that all clones have reactivity to an antibody-drug conjugate independently of difference in DAR and antibody moiety, and are used as both a capture reagent and a detection reagent. Of the clones, clone 1A3 exhibiting the largest signal value was selected and intended to use in detecting the antibody-drug conjugate according to the present invention.

xv) Determination of Isotype of Mouse Monoclonal Antibody

The isotype of a mouse monoclonal antibody (hereinafter referred to as "mouse antibody 1A3") of clone 1A3 obtained in xiv) was determined by Mouse monoclonal isotyping test kit (manufactured by AbD Serotec). As a result, the isotype was confirmed to be IgG2b, κ chain.

xvi) Gene Cloning of Monoclonal Antibody and Sequencing Analysis of N Terminus Amino Acid Total RNA was prepared from mouse antibody 1A3-producing hybridoma using TRIzol Reagent (LIFE TECHNOLOGIES). Sequencing analysis (Edman sequencing) of N terminus amino acid of purified mouse antibody 1A3 was carried out. Further, the nucleotide sequence of clone 1A3 was analyzed by antibody gene cloning. As a result of the antibody gene cloning, a single sequence of a heavy chain variable region and a single sequence of a light chain variable region were obtained. As the result of analysis, it was confirmed that the N terminus amino acid sequence of the purified mouse antibody 1A3 matches with the N terminus amino acid sequence of the nucleotide sequence of clone 1A3 obtained by antibody gene cloning.

The amino acid sequence of a heavy chain of mouse antibody 1A3 is represented by SEQ ID NO: 15. The amino acid sequence consisting of amino acid residues 1 to 19 of SEQ ID NO: 15 represents a signal sequence; the amino acid sequence consisting of amino acid residues 20 to 141 thereof represents a heavy chain variable region; and the amino acid sequence consisting of amino acid residues 142 to 477 thereof represents a heavy chain constant region.

The amino acid sequence of a light chain of mouse antibody 1A3 is represented by SEQ ID NO: 16. The amino acid sequence consisting of amino acid residues 1 to 20 of SEQ ID NO: 16 represents a signal sequence; the amino acid sequence consisting of amino acid residues 21 to 127 thereof represents a light chain variable region; and the amino acid sequence consisting of amino acid residues 128 to 234 thereof represents a light chain constant region.

The nucleotide sequence encoding the amino acid sequence of a heavy chain of mouse antibody 1A3 is represented by SEQ ID NO: 17. The nucleotide sequence consisting of nucleotide residues 1 to 57 of SEQ ID NO: 17 represents a signal sequence; and the nucleotide sequence consisting of nucleotide residues 58 to 423 thereof encodes the amino acid sequence of a heavy chain variable region.

The nucleotide sequence encoding the amino acid sequence of a light chain of mouse antibody 1A3 is represented by SEQ ID NO: 18. The nucleotide sequence consisting of nucleotide residues 1 to 60 of SEQ ID NO: 18 represents a signal sequence; and the nucleotide sequence of nucleotides 61 to 459 thereof encodes the amino acid sequence of a heavy chain variable region.

In addition, CDR was analyzed.

According to the definition of Abm, it was found that the heavy chain variable region of mouse antibody 1A3 has CDRH1 (GFTFSDYGMV) consisting of the amino acid sequence represented by SEQ ID NO: 1, CDRH2 (YISSGS-SAIY) consisting of the amino acid sequence represented by SEQ ID NO: 2, and CDRH3 (PPRYDVYSAWFAY) consisting of the amino acid sequence represented by SEQ ID NO: 3; and that the light chain variable region of mouse antibody 1A3 has CDRL1 (KASQDVGSAVV) consisting of the amino acid sequence represented by SEQ ID NO: 4, CDRL2 (WASTRHT) consisting of the amino acid sequence represented by SEQ ID NO: 5, and CDRL3 (QQYSSYPVT) consisting of the amino acid sequence represented by SEQ ID NO: 6.

According to the definition of Chothia, it was found that the heavy chain variable region of mouse antibody 1A3 has CDRH1 (GFTFSDY) consisting of the amino acid sequence represented by SEQ ID NO: 7, CDRH2 (SSGSSA) consisting of the amino acid sequence represented by SEQ ID NO: 8, and CDRH3 (PPRYDVYSAWFAY) consisting of the amino acid sequence represented by SEQ ID NO: 3; and that the light chain variable region of mouse antibody 1A3 has CDRL1 (KASQDVGSAVV) consisting of the amino acid sequence represented by SEQ ID NO: 4 CDRL2 (WASTRHT) consisting of the amino acid sequence represented by SEQ ID NO: 5, and CDRL3 (QQYSSYPVT) consisting of the amino acid sequence represented by SEQ ID NO: 6.

According to the definition of Kabat, it was found that the heavy chain variable region of mouse antibody 1A3 has CDRH1 (DYGMV) consisting of the amino acid sequence represented by SEQ ID NO: 9, CDRH2 (YISSGSSAIYY-ADTVKG) consisting of the amino acid sequence represented by SEQ ID NO: 10, and CDRH3 (PPRYDVYSAW-FAY) consisting of the amino acid sequence represented by SEQ ID NO: 3; and that the light chain variable region of mouse antibody 1A3 has CDRL1 (KASQDVGSAVV) consisting of the amino acid sequence represented by SEQ ID NO: 4, CDRL2 (WASTRHT) consisting of the amino acid sequence represented by SEQ ID NO: 5, and CDRL3 (QQYSSYPVT) consisting of the amino acid sequence represented by SEQ ID NO: 6.

According to the definition of Imgt (registered trademark), it was found that the heavy chain variable region of mouse antibody 1A3 has CDRH1 (GFTFSDYG) consisting of the amino acid sequence represented by SEQ ID NO: 11, CDRH2 (ISSGSSAI) consisting of the amino acid sequence represented by SEQ ID NO: 12, and CDRH3 (ARP-PRYDVYSAWFAY) consisting of the amino acid sequence represented by SEQ ID NO: 13; and that the light chain variable region of mouse antibody 1A3 has CDRL1 (QDVGSA) consisting of the amino acid sequence represented by SEQ ID NO: 14, CDRL2 consisting of a tripeptide represented by WAS (tryptophan-alanine-serine), and CDRL3 (QQYSSYPVT) consisting of the amino acid sequence represented by SEQ ID NO: 6.

[Example 4] Measurement of Plasma-Concentration in Non-Clinical Study

Using mouse antibody 1A3 obtained in Example 2, a method for measuring the concentration in plasma of HER2-ADC (I) in a mouse and a method for measuring the concentration in plasma of HER3-ADC (I), TROP2-ADC (I) and B7-H3-ADC (I) in a monkey were developed. Mouse antibody 1A3 can be used by labelling it with DyLight650 (registered trademark) or Alexa Fluor (registered trademark) 647 serving as a detection reagent. The plasma-concentration of the antibody-drug conjugate according to the present invention can be measured even if either one of them is selected. Further, a calibration curve can be prepared independent of difference in DAR and antibody moiety and can be used in measurement of the concentration in plasma of the antibody-drug conjugate according to the present invention.

i) HER2-ADC (I)

The method for measuring the concentration in plasma of HER2-ADC (I) in a mouse was developed by Gyrolab xP workstation. As a capture reagent, Biotinylated Mouse Anti-(Anti-HER2 Ab) idiotype Ab (herein, "(Anti-HER2 Ab)" refers to an antibody comprising a heavy chain consisting of the amino acid sequence consisting of amino acid residues 1 to 449 of SEQ ID NO: 21 and a light chain consisting of the amino acid sequence consisting of amino acid residues 1 to 214 of SEQ ID NO: 22) (13C1) (IBL). The concentration thereof was controlled with 0.1% PS20-containing PBS to be 350 nM. Samples for a calibration curve were prepared by controlling the concentration of HER2-ADC (I) to be 0, 0.150, 0.200, 0.600, 1.60, 4.00, 16.0, 40.0, 100, and 140 µg/mL with the mouse plasma diluted with Rexxip HN 100 fold. As a detection reagent, mouse antibody 1A3 labeled by DyLight650 (registered trademark) labeling kit was used and the concentration thereof was controlled with Rexxip F to be 10 nM. These reagents and samples for a calibration curve were added to 96-well PCR plates and set together with Gyrolab Bioaffy 200 in Gyrolab xP workstation. As the measurement wizard, 200-3W-002-A (PMT1) was used. The regression analysis was carried out in accordance with the 5-parameter logistic model using Gyrolab Evaluator 3.3.9.175. The calibration curve is shown in FIG. 24.

A method for measuring the concentration in plasma of Total antibody (anti-HER2 antibody and HER2-ADC (I)) in a mouse was developed by Gyrolab xP workstation. As a capture reagent, Biotinylated Mouse Anti-(Anti-HER2 Ab) idiotype Ab (13C1) (IBL) was used and the concentration thereof was controlled with 0.1% PS20-containing PBS to be 350 nM. Samples for a calibration curve were prepared by controlling the concentration of HER2-ADC (I) to be 0, 0.150, 0.200, 0.600, 1.60, 4.00, 16.0, 40.0, 100 and 140 µg/mL with the mouse plasma diluted with Rexxip HN 100 fold. As a detection reagent, Alexa Fluor (registered trademark) 647 anti-human IgG, Fcγ antibody (Jakckson Immno Research Laboratories, Inc.) was used and the concentration thereof was controlled with Rexxip F to be 10 nM. These reagents prepared and samples for a calibration curve were added to 96-well PCR plates and set together with Gyrolab Bioaffy 200 in Gyrolab xP workstation. As the measurement wizard, 200-3W-002-A (PMT1) was used. The regression analysis was carried out in accordance with the 5-parameter logistic model using Gyrolab Evaluator 3.3.9.175.

The measurement results of concentration is shown in Table 1.

tion reagent, mouse antibody 1A3 labeled using Alexa Fluor (registered trademark) 647 labeling kit was used and the concentration thereof was controlled to be 10 nM with Rexxip F. These reagents and samples for a calibration curve were added to 96-well PCR plates and set in Gyrolab xP workstation. As the measurement wizard, 200-3W-002-A (PMT1) was used. The regression analysis was carried out in accordance with the 4-parameter logistic model (weight: Response) using Gyrolab Evaluator 3.3.7.171. The calibration curve is shown in FIG. 26.

iv) B7-H3-ADC (I)

A method for measuring the concentration in plasma measurement of B7-H3-ADC (I) in a monkey was developed by Gyrolab xP workstation. Validation was obtained. As a capture reagent, B7-H3 C1 domain (Lot number B7 OmJ1, Daiichi Sankyo co., ltd.) labeled with EZ-Link Sulfo-NHS-LC-Biotin (Thermo Fisher Scientific Inc.) was used and the concentration thereof was controlled with 0.1% PS20-containing PBS to be 700 nM. Samples for a calibration curve were prepared by controlling the concentration of

TABLE 1

| | Mean Plasma Concentration (µg/mL) | | | | | | |
|---|---|---|---|---|---|---|---|
| Time (d) | 0.00347 | 0.292 | 1 | 3 | 7 | 14 | 21 |
| Total Ab | 66.9 ± 4.9 | 41.3 ± 1.4 | 27.9 ± 1.4 | 24.3 ± 2.3 | 17.0 ± 1.2 | 10.7 ± 0.5 | 6.66 ± 1.19 |
| HER2-ADC (1) | 73.4 ± 6.6 | 44.8 ± 6.0 | 30.3 ± 1.2 | 23.5 ± 1.7 | 16.9 ± 0.4 | 8.92 ± 0.91 | 5.20 ± 0.98 | ii) HER3-ADC (I)

A method for measuring the concentration in plasma of HER3-ADC (I) in a monkey was developed by Gyrolab xP workstation. Validation was obtained. As a capture reagent, HER3 (Recombinant Human ErbB-3/HER3 Protein, ACRO biosystems) labeled with EZ-Link Sulfo-NHS-LC-Biotin (Thermo Fisher Scientific Inc.) was used and the concentration thereof was controlled to be 700 nM with 0.1% PS20-containing PBS. Samples for a calibration curve were prepared by controlling the concentration of HER3-ADC (I) to be 0, 0.0750, 0.100, 0.250, 0.750, 2.25, 6.75, 20.0, 38.0 and 48.0 µg/mL with the monkey plasma and further diluting them with Polysorbate 20-containing PBS and Rexxip AN (GYROS PROTEIN Technologies) 100 fold. As a detection reagent, mouse antibody 1A3 labeled using Alexa Fluor (registered trademark) 647 labeling kit was used and the concentration thereof was controlled with Rexxip F to be 10 nM. These reagents prepared and samples for a calibration curve were added to 96-well PCR plates and set in Gyrolab xP workstation. As the measurement wizard, 200-3W-002-A (PMT5) was used. The regression analysis was carried out in accordance with the 4-parameter logistic model (weight: Response) using Gyrolab Evaluator 3.3.7.171. The calibration curve is shown in FIG. 25.

iii) TROP2-ADC (I)

A method for measuring the concentration in plasma of TROP2-ADC (I) in a monkey was developed by Gyrolab xP workstation. Validation was obtained. As a capture reagent, new hTrop2 (Lot number V35, Daiichi Sankyo co., ltd.) labeled with EZ-Link Sulfo-NHS-LC-Biotin was used and the concentration thereof was controlled to be 350 nM with 0.1% PS20-containing PBS. Samples for a calibration curve used were those prepared by controlling the concentration of TROP2-ADC (I) to be 0, 0.00750, 0.0100, 0.0250, 0.0750, 0.250, 0.750, 2.50, 7.50 and 10.0 µg/mL with the monkey plasma and the samples were further diluted 10 fold with Rexxip HN (GYROS PROTEIN Technologies). As a detec- B7-H3-ADC (I) to be 0, 0.0750, 0.100, 0.250, 0.750, 2.25, 6.75, 20.0, 38.0 and 48.0 µg/mL with the mouse plasma and further diluting them with Polysorbate 20 containing PBS and Rexxip HN (GYROS PROTEIN Technologies) 50 fold. As a detection reagent, mouse antibody 1A3 labeled using Alexa Fluor (registered trademark) 647 labeling kit was used and the concentration thereof was controlled to be 10 nM with Rexxip F. These reagents and samples for a calibration curve were added to 96-well PCR plates and set in Gyrolab xP workstation. As the measurement wizard, 200-3W-001-A (PMT5) was used. The regression analysis was carried out in accordance with the 4-parameter logistic model (weight: Response) using Gyrolab Evaluator 3.3.7.171. The calibration curve is shown in FIG. 27.

[Example 5] Immunostaining Using Mouse Antibody 1A3 i) Confirmation of Stainability Using Subcutaneously Transplanted Human-Derived Tumor To a highly immunodeficient mouse (NOG mouse), a human-derived tumor is subcutaneously transplanted. After the antibody-drug conjugate according to the present invention is administered, the tumor tissue is taken to prepare paraffin-embedded specimens. Then, stainability of a mouse antibody 1A3 is examined. The tumor tissue is taken from a NOG mouse to which the antibody-drug conjugate according to the present invention is not administered and used as a negative control. Deparaffinization and antigen activation are carried out using Autostainer Link pretreatment system (PT Link, manufactured by DAKO) and an antigen retrieval solution (Target Retrieval Solution Low pH, manufactured by DAKO). The following staining operation is carried out using an automatic staining device (Dako Autostainer Link 48: Manufactured by DAKO). After washing with EnVision FLEX WASH BUFFER (manufactured by DAKO), Peroxidase Block 3% $H_2O_2$ (manufactured by DAKO) is add;

incubation is carried out; and washing is carried out with EnVision FLEX WASH BUFFER. Protein Block serum free (manufactured by DAKO) is added; incubation s carried out; and liquid is removed by air blow. Mouse antibody 1A3 is diluted with REAL Antibody Diluent (manufactured by DAKO) and reacted. After washing with EnVision FLEX WASH BUFFER, EnVision+System-HRP Labelled Polymer Anti-Mouse #K4000 (manufactured by DAKO) is added; incubation is carried out; and then, washing with EnVision FLEX WASH BUFFER is carried out.

DAKO Liquid DAB+Substrate Chromogen System is add and incubation is carried out; and washing with EnVision FLEX WASH BUFFER is carried out. EnVision FLEX Hematoxylin is added and incubation is carried out; and washing with EnVision FLEX WASH BUFFER and ion exchange water is carried out.

It is confirmed that the NOG mouse administered with the antibody-drug conjugate according to the present invention can be satisfactorily stained with mouse antibody 1A3, and that the staining intensity increases with an increase of concentration of mouse antibody 1A3. In addition, it is confirmed that a NOG mouse not administered with the antibody-drug conjugate according to the present invention is not stained with mouse antibody 1A3. Note that, since the NOG mouse is defective in B cells, it is known that the background is not stained with mouse-derived endogenous IgG (Ito M, et al. Blood 100 (9): 3175-3182, 2002).

ii) Confirmation of Specificity of Mouse Antibody 1A3

After mouse antibody 1A3 is mixed with compound (2) or SN-38, the mixture is used for immunostaining. The blending ratio of antibody 1A3: compound (2): SN-38 is defined to be 0.1:0.04:0.03 based on the molecular weights. Staining was carried out in the same manner as in i).

It is confirmed that stainability of mouse antibody 1A3 disappears by mixing it with compound (2). It is also confirmed that stainability of mouse antibody 1A3 does not disappear by mixing it with SN-38.

[Example 6] Preparation of Rabbit Chimeric Antibody i) Design of Rabbit Chimeric Antibody Derived from Mouse Antibody 1A3

A rabbit chimeric antibody derived from mouse antibody 1A3 (hereinafter referred to as "rabbit chimeric antibody 1A3") was designed as follows. The sequence of the rabbit chimeric antibody was designed with reference to IMGT (registered trademark) by connecting the heavy chain constant region IGHG*02 and the light chain constant region IGKC2*01 of a rabbit to respective variable regions of both chains of clone 1A3.

The amino acid sequence of a heavy chain of rabbit chimeric antibody 1A3 is represented by SEQ ID NO: 19. The amino acid consisting of amino acid residues 1 to 19 of SEQ ID NO: 19 represents a signal sequence; the amino acid sequence consisting of amino acid residues 20 to 141 thereof represents a heavy chain variable region, and the amino acid sequence of amino acid residues 142 to 464 thereof represents a heavy chain constant region.

The amino acid sequence of a light chain of rabbit chimeric antibody 1A3 is represented by SEQ ID NO: 20. The amino acid sequence consisting of amino acid residues 1 to 20 of SEQ ID NO: 20 represents a signal sequence; the amino acid sequence consisting of amino acid residues 21 to 127 thereof represents a light chain variable region; and the amino acid sequence consisting of amino acid residues 128 to 233 thereof represents a light chain constant region.

ii) Construction of Antibody Expression Vector pCMA-LK

A fragment (about 5.4 kb) obtained by digesting plasmid pcDNA3.3-TOPO/LacZ (Invitrogen) with restriction enzyme XbaI and PmeI was ligated to a DNA fragment having a nucleotide sequence (SEQ ID NO: 29) encoding the amino acid sequences of a human light chain signal sequence and a human κ chain constant region by use of In-Fusion Advantage PCR cloning kit (CLONTECH) to obtain pcDNA3.3/LK.

pCMA-LK was constructed by removing a neomycin expression unit from pcDNA3.3/LK.

iii) Construction of Rabbit Chimeric Antibody 1A3 Heavy Chain Expression Vector

A DNA fragment having the nucleotide sequence (SEQ ID NO: 30) encoding the amino acid sequence (SEQ ID NO: 19) of a heavy chain of rabbit chimeric antibody 1A3 was synthesized (GENEART). The nucleotide sequence of nucleotide residues 26 to 82 of SEQ ID NO: 30 represents a signal sequence; the nucleotide sequence of nucleotide residues 83 to 448 encodes the amino acid sequence of a heavy chain variable region; and the nucleotide sequence of nucleotide residues 449 to 1417 encodes the amino acid sequence of the constant region.

The DNA fragment synthesized by use of In-Fusion HD PCR cloning kit (CLONTECH) was ligated to the DNA fragment, which was prepared by digesting pCMA-LK with XbaI and PmeI and removing the nucleotide sequence (SEQ ID NO: 29) encoding the amino acid sequences of a light chain signal sequence and a human κ chain constant region to construct a rabbit chimeric antibody 1A3 heavy chain expression vector.

iv) Construction of Rabbit Chimeric Antibody 1A3 Light Chain Expression Vector

A DNA fragment having the nucleotide sequence (SEQ ID NO: 31) encoding the amino acid sequence (SEQ ID NO: 20) of a light chain of rabbit chimeric antibody 1A3 was synthesized (GENEART). The nucleotide sequence of nucleotide residues 26 to 85 of SEQ ID NO: 31 represents a signal sequence; the nucleotide sequence of nucleotide residues 86 to 406 encodes the amino acid sequence of a light chain variable region; and the nucleotide sequence of nucleotide residues 407 to 724 encodes the amino acid sequence of the constant region. A rabbit chimeric antibody 1A3 light chain expression vector was constructed in the same manner as in iii).

v) Production of Rabbit Chimeric Antibody 1A3

FreeStyle 293F cells (Invitrogen) were subcultured in accordance with a manual. FreeStyle 293F cells (Invitrogen) ($2.4 \times 10^9$) during the logarithmic growth phase were seeded in Optimum Growth 5L Flask (Thomson), diluted with FreeStyle293 expression medium (Invitrogen) to prepare $1.88 \times 10^6$ cells/mL. To Opti-Pro SFM culture medium (Invitrogen) (40 mL), 0.48 mg of the rabbit chimeric antibody 1A3 heavy chain expression vector, 0.72 mg of rabbit chimeric antibody 1A3 light chain expression vector and 3.6 mg of polyethyleneimine (Polyscience #24765) were added. The mixture was gently stirred, allowed to stand still for further 5 minutes, and then, added to FreeStyle 293F cells. The mixture was incubated at 37° C., in an 8% $CO_2$ incubator for 4 hours while shaking at a rate of 90 rpm. Thereafter, 1200 mL of EX-CELL VPRO culture medium (SAFC Biosciences), 18 mL of GlutaMAX I (GIBCO) and 60 mL of Yeastolate Ultrafiltrate (GIBCO) were added. The mixture was cultured at 37° C. in an 8% $CO_2$ incubator for 7 days while shaking at a rate of 90 rpm. The resultant culture supernatant was filtered by Disposable Capsule Filter (Advantec #CCS-045-E1H) to obtain a culture supernatant containing rabbit chimeric antibody 1A3.

vi) Purification of Rabbit Chimeric Antibody 1A3

The culture supernatant obtained in v) was purified by a single step of rProtein A affinity chromatography. The culture supernatant was applied to a column (manufactured by GE Healthcare Bioscience) charged with MabSelectSuRe equilibrated with PBS, and then, washed with PBS (in a volume double or more as large as the column volume). Subsequently, elution was made with a 2 M arginine hydrochloride solution (pH4.0) and fractions containing the antibody were collected. The fractions collected were dialyzed (Slide-A-Lyzer Dialysis Cassette, company: Thermo Scientific) to perform PBS buffer replacement. The antibody was concentrated by Centrifugal UF Filter Device VIVASPIN20 (cutoff molecular weight UF10K, company: Sartorius) and the concentration of IgG was controlled to be 2 mg/mL or more. Finally, filtration was made by Minisart-Plus filter (Sartorius) to obtain a sample of purified rabbit chimeric antibody 1A3.

[Example 7] Production of Antibody-Drug Conjugate i) Production (1) of Anti-GPR20 Antibody-Drug Conjugate In accordance with the production method described in International Publication No. WO 2018/135501 and using an anti-GPR20 antibody (antibody comprising a heavy chain consisting of the amino acid sequence consisting of amino acid residues 20 to 472 of SEQ ID NO: 32 and a light chain consisting of the amino acid sequence consisting of amino acid residues 21 to 234 of SEQ ID NO: 33), an anti-GPR20 antibody-drug conjugate, in which a drug-linker represented by the following formula:

[Formula 35]

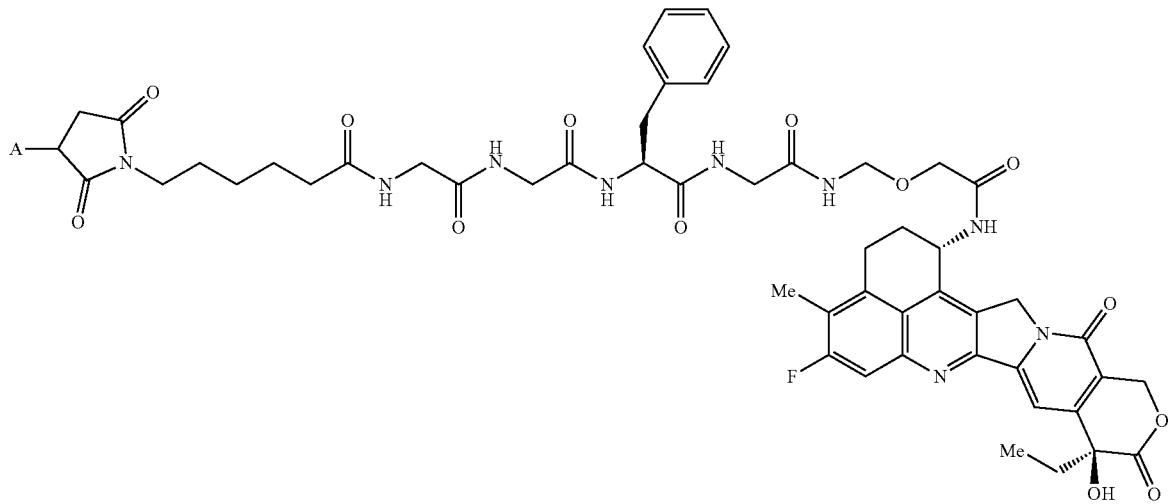

wherein A represents a connection position to the antibody) is conjugated to the anti-GPR20 antibody via a thioether bond (referred to as "GPR20-ADC (I)" in the present invention), was produced.

ii) Production (1) of Anti-CDH6 Antibody-Drug Conjugate

In accordance with the production method described in International Publication No. WO2018/212136 and using an anti-CDH6 antibody (antibody comprising a heavy chain consisting of the amino acid sequence consisting of amino acid residues 20 to 471 of SEQ ID NO: 34 and a light chain consisting of the amino acid sequence consisting of amino acid residues 21 to 233 of SEQ ID NO: 35), an anti-CDH6 antibody-drug conjugate, in which a drug-linker represented by the following formula:

[Formula 36]

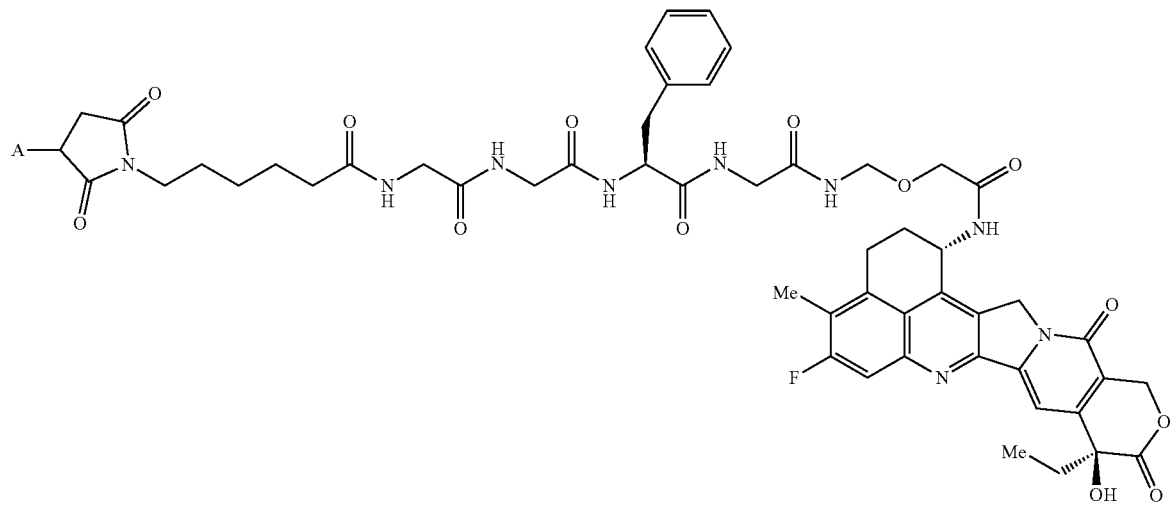

wherein A represents a connection position to the antibody) is conjugated to the anti-CDH6 antibody via a thioether bond (referred to as "CDH6-ADC (I)" in the present invention), was produced.

[Example 8] Immunostaining Using Rabbit Chimeric Antibody 1A3 i) Confirmation of Stainability Using Subcutaneously Transplanted Human-Derived Tumor after Administration of TROP2-ADC (I)

To an immunodeficient mouse (nude mouse), human head and neck cancer cell line FaDu was subcutaneously transplanted. After TROP2-ADC (I) was administered, the tumor tissue was taken to prepare paraffin-embedded specimens. Then, stainability of rabbit chimeric antibody 1A3 was examined. The tumor tissue was taken from a nude mouse to which an anti-TROP2 antibody (an antibody comprising a heavy chain consisting of amino acid sequence of amino acid residues 20 to 470 of SEQ ID NO: 25 and a light chain consisting of amino acid sequence of amino acid residues 21 to 234 of SEQ ID NO: 26, hereinafter referred to as "Anti-TROP2 Ab") and used as a negative control. Deparaffinization and antigen activation were carried out using Autostainer Link pretreatment system (PT Link, manufactured by DAKO) and an antigen retrieval solution (Target Retrieval Solution Low pH, manufactured by DAKO) at 97° C. for 40 minutes. The following staining operation was carried out using an automatic staining device (Dako Autostainer Link 48: manufactured by DAKO) at room temperature. After washing once with EnVision FLEX WASH BUFFER (manufactured by DAKO), REAL Peroxidase-Blocking Solution (manufactured by DAKO) was added; incubation was carried out for 5 minutes; and washing was carried out once with EnVision FLEX WASH BUFFER. Protein Block serum free (manufactured by DAKO) was added; incubation was carried out for 30 minutes; and liquid was removed by air blow. Rabbit chimeric antibody 1A3 was diluted with REAL Antibody Diluent (manufactured by DAKO) to 0.1 μg/mL and reaction was made for 30 minutes. After washing three times with EnVision FLEX WASH BUFFER, EnVision+System-HRP Labelled Polymer Anti-Rabbit (manufactured by DAKO) was added; incubation was carried out for 30 minutes; and then, washing twice with EnVision FLEX WASH BUFFER was carried.

DAKO Liquid DAB+Substrate Chromogen System was added and incubation was carried out for 10 minutes in total; and washing once with EnVision FLEX WASH BUFFER was carried out. EnVision FLEX Hematoxylin was added and incubation was carried out for 5 minutes; and washing with EnVision FLEX WASH BUFFER and ion exchange water was carried out three times in total.

FIG. 35 shows a typical stained image. Rabbit chimeric antibody 1A3 showed satisfactory stainability to the subcutaneous tumor tissue of an animal administered with TROP2-ADC (I); whereas, rabbit chimeric antibody 1A3 did not show stainability to the subcutaneous tumor tissue of an animal administered with an anti-TROP2 Ab.

ii) Confirmation of Stainability Using Subcutaneously Transplanted Human-Derived Tumor after Administration GPR20-ADC (I)

To an immunodeficient mouse (nude mouse), GPR20 overexpressing human gastrointestinal stromal tumor cell line GIST-T1/GPR20 was subcutaneously transplanted. After GPR20-ADC (I) was administered, the tumor tissue was taken to prepare paraffin-embedded specimens. Then, stainability of rabbit chimeric antibody 1A3 was examined. The tumor tissue was taken from a mouse not administered with GPR20-ADC (I) and used as a negative control. Staining was carried out in the same manner as in i).

FIG. 36 shows a typical stained image. Rabbit chimeric antibody 1A3 showed satisfactory stainability to the subcutaneous tumor tissue of an animal administered with GPR20-ADC (I); whereas, rabbit chimeric antibody 1A3 did not show stainability to the subcutaneous tumor tissue of an animal not administered with an GPR20-ADC (I).

[Example 9] Immunostaining Using Mouse Antibody 1A3 i) Confirmation of Stainability Using Subcutaneously Transplanted Human-Derived Tumor after Administration of CDH6-ADC (I)

To a highly immunodeficient mouse (NOG mouse), a human tumor taken from a patient with clear cell renal cell carcinoma was subcutaneously transplanted. After CDH6-ADC (I) was administered, the tumor tissue was taken to prepare paraffin-embedded specimens. Then, stainability of mouse antibody 1A3 was examined. The tumor tissue was taken from an NOG mouse to which CDH6-ADC (I) was not administered and used as a negative control. Deparaffinization and antigen activation were carried out using Autostainer Link pretreatment system (PT Link, manufactured by DAKO) and an antigen retrieval solution (Target Retrieval Solution Low pH, manufactured by DAKO) at 97° C. for 40 minutes. The following staining operation was carried out using an automatic staining device (Dako Autostainer Link 48: manufactured by DAKO) at room temperature. After washing once with EnVision FLEX WASH BUFFER (manufactured by DAKO), Peroxidase Block 3% H₂O₂ (manufactured by DAKO) was added; incubation was carried out for 5 minutes; and washing was carried out once with EnVision FLEX WASH BUFFER. Protein Block serum free (manufactured by DAKO) was added; incubation was carried out for 30 minutes; and liquid was removed by air blow. Mouse antibody 1A3 was diluted with REAL Antibody Diluent (manufactured by DAKO) to fall in the range of 0.03 µg/mL to 0.3 µg/mL and reaction was made for 60 minutes. After washing three times with EnVision FLEX WASH BUFFER, EnVision+System-HRP Labelled Polymer Anti-Mouse #K4000 (manufactured by DAKO) was added; incubation was carried out for 30 minutes; and then, washing with EnVision FLEX WASH BUFFER was carried out twice.

DAKO Liquid DAB+Substrate Chromogen System was added and incubation was carried out for 10 minutes in total; and washing once with EnVision FLEX WASH BUFFER was carried out. EnVision FLEX Hematoxylin was added and incubation was carried out for 5 minutes; and washing with EnVision FLEX WASH BUFFER and ion exchange water was carried out three times in total.

FIG. 37 shows a typical stained image. Mouse antibody 1A3 showed satisfactory stainability to an animal administered with CDH6-ADC (I) and staining intensity increased with an increase of the concentration of mouse antibody 1A3. In contrast, mouse antibody 1A3 did not show stainability to the animal administered with CDH6-ADC (I). Note that, since the NOG mouse is defective in B cells, it is known that the background staining is not observed with mouse-derived endogenous IgG (Ito M, et al. Blood 100 (9): 3175-3182, 2002).

ii) Confirmation of Specificity of Mouse Antibody 1A3

After mouse antibody 1A3 was mixed with compound (2) or SN-38, the mixture was used for immunostaining.

Note that the compound (2) is a compound represented by the following formula:

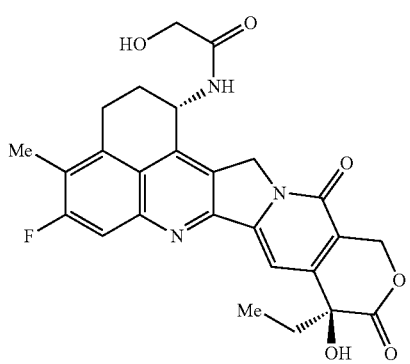

[Formula 37]

SN-38 is a compound represented by the following formula:

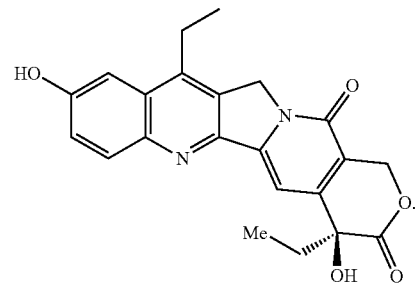

[Formula 38]

The blending ratio of mouse antibody 1A3: compound (2): SN-38 was defined to be 0.1:0.04:0.03 based on the molecular weights. Staining was carried out in the same manner as in i).

FIG. 38 shows a typical stained image. The staining ability of mouse antibody 1A3 disappeared by mixing with the compound (2) but did not disappear by mixing with SN-38. From this, it was demonstrated that mouse antibody 1A3 specifically recognizes the compound (2) in the tissue.

[Example 10] Measurement of Concentration in Plasma in Non-Clinical Study

The method for measuring the concentration in plasma of GPR20-ADC (I) in a mouse was developed by Gyrolab xP workstation (GYROS PROTEIN Technologies). As a capture reagent, mouse antibody 1A3 was labeled with biotin by use of a labeling kit (ChromaLink Biotin Protein Labeling Kit, Solulink) was used and the concentration thereof was controlled to be 700 nM with a 0.1% PS20-containing PBS. Samples for a calibration curve were prepared by controlling the concentration of GPR20-ADC (I) to be 0, 5, 10, 20, 50, 100, 200, 500, 1000, 2000, 5000, 10000 ng/mL with the mouse plasma and diluted with Rexxip AN (GYROS PROTEIN Technologies) up to 10 fold. As a detection reagent, Mouse Anti-(Anti-GPR20 Ab) (herein, "(Anti-GPR20 Ab)" represents an antibody comprising a heavy chain consisting of amino acid sequence consisting of amino acid residues 20 to 472 of SEQ ID NO: 32 and a light chain consisting of amino acid sequence consisting of amino acid residues 21 to 234 of SEQ ID NO: 33) idiotype Ab (71C1) (IBL) was labeled by DyLight650 (registered trademark) labeling kit and put in use, and the concentration thereof was controlled with Rexxip F (GYROS PROTEIN Technologies) to be 10 nM. These reagents and samples for a calibration curve were added to 96-well PCR plates and set at Gyrolab xP workstation. Using Bioaffy200, wizard was measured by 200-3W-002-A (PMT1). Regression analysis was carried out by use of Gyrolab Evaluator 3.3.9.175 in 4-parametric logistic model (weight: Response). The calibration curve is shown in FIG. 39.

[Example 11] Measurement of Plasma-Concentration in Non-Clinical Study

The method for measuring the concentration in plasma of HER2-ADC (I) in a human was developed by using ECL. A High Bind plate (Meso Scale Diagnostics, LLC: MSD) was coated with mouse antibody 1A3 and then washed. After blocking was made with a blocking buffer (BSA and PS20- contining PBS), HER2-ADC (I) was controlled in concentration to be 0, 200, 400, 800, 1600, 3200, 6400, 12800, 20000 and 25600 ng/mL, diluted 1000 fold with an assay diluent and used as samples for a calibration curve. The Biotinylated Mouse Anti-(Anti-HER2) idiotype Ab (13C1) (IBL) labeled with biotin by EZ-Link Sulfo-NHS-LC-LC Biotin (Thermo Fisher Scientific Inc.) and sulfo-tag streptavidin (MSD) were pre-incubated to prepare a detection solution. To the plate, to which the samples for a calibration curve were added, incubated and washed, the detection solution was added, to form a complex. Then, 4×Read Buffer T (MSD) was diluted double with purified water and added to the plate washed. Measurement was made by MSD SECTOR Imager 6000 (control software: MSD Discovery Workbench Version 3.0.18). The regression analysis was made by 4-parametric logistic model (weight: 1/Response$^2$). The calibration curve is shown in FIG. 40.

[Example 12] Confirmation of Chemical Structure to be Recognized by Mouse Antibody 1A3

The chemical structure to be recognized by mouse antibody 1A3 was checked by competitive inhibition with HER2-ADC (I) using Gyrolab xP workstation (GYROS PROTEIN Technologies). As the compound for use in competitive inhibition, compound (1), compound (2), compound (7), compound (8), compound (9), compound (10), compound (11), Topotecan and Rubitecan were selected.

Note that, the compound (1) is a compound represented by the following formula:

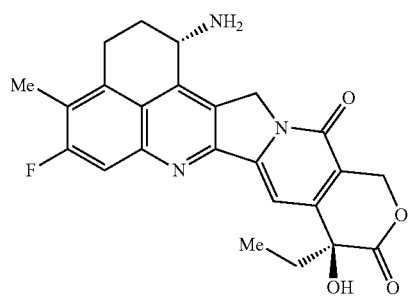

[Formula 39]

The compound (2) is a compound represented by the following formula:

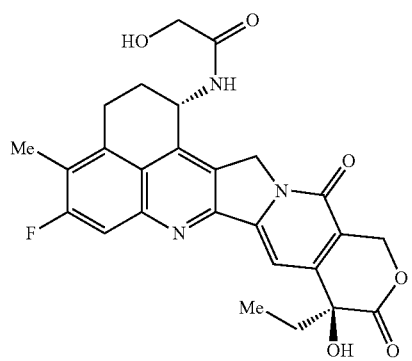

[Formula 40]

The compound (7) is a compound represented by the following formula:

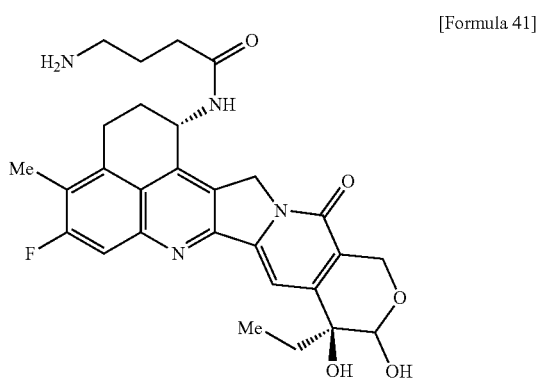 [SMILES: CC[C@]1(O)c2cc3n(c(=O)c2COC1O)Cc1c-3nc2cc(F)c(C)c3c2c1[C@@H](NC(=O)CCCN)CC3]

[Formula 41]

The compound (8) is a compound represented by the following formula:

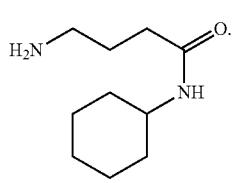

[Formula 42]

The compound (9) is a compound represented by the following formula:

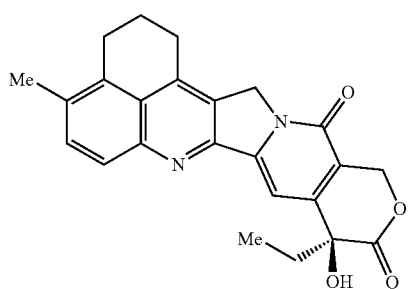

[Formula 43]

(Sugimori M. et al., J Med. Chem. 1994, 3033-3039).

The compound (10) is a compound represented by the following formula:

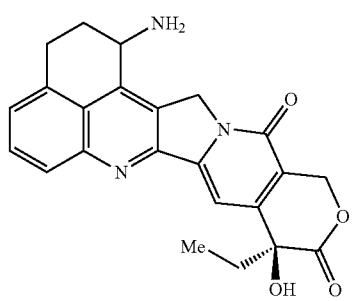

[Formula 44]

(U.S. Pat. No. 5,834,476).

The compound (11) is a compound represented by the following formula:

[Formula 45]

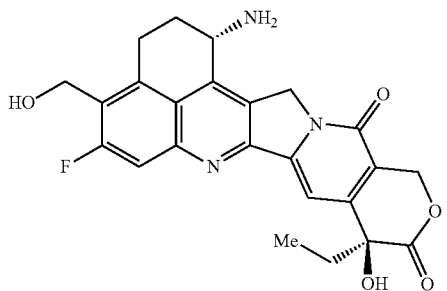

(Atsumi R. et al., Arzneimittel-Forschung 2001, 253-257).

Topotecan is a compound represented by the following formula:

[Formula 46]

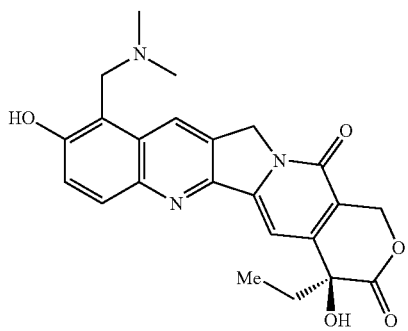

Rubitecan is a compound represented by the following formula:

[Formula 47]

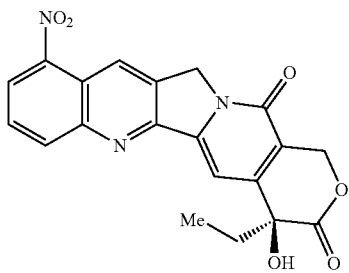

As the capture reagent, mouse antibody 1A3 labeled with biotin by a labeling kit (ChromaLink Biotin Protein LABELING Kit, Solulink) was used. The concentration thereof was controlled to be 700 nM with 0.1% PS20-containing PBS. The compounds for use in competitive inhibition, compound (1), compound (2), compound (7), compound (8), compound (9), compound (10), compound (11), Topotecan and Rubitecan were separately dissolved in DMSO. The solutions each was diluted with 10% or 20% DMSO in Rexxip HN (GYROS PROTEIN Technologies) to prepare 0, 1 and 100 µg/mL dilution solutions. To each of them, the 700 nM mouse antibody 1A3 solution was added in an equal amount. The mixture was stirred and allowed to react at room temperature in a dark place for one hour or more. The concentration of HER2-ADC (I) was controlled with Rexxip HN to be 0, 0.244, 0.977, 3.91, 15.6, 62.5, 250 and 1000 ng/mL. As the detection reagent, Mouse Anti-(Anti-HER2 Ab) idiotype Ab (13C1) (IBL) was labeled by DyLight650 (registered trademark) labeling kit and put in use. The concentration thereof was controlled with Rexxip F (GYROS PROTEIN Technologies) to be 10 nM. The above solution was set at Gyrolab xP workstation and measurement was carried out by use of Gyrolab Bioaffy 200 at 200-3W-002-A (PMT5). The regression analysis was carried out by use of Gyrolab Evaluator 3.4.0.24 in 4-parametric logistic model (weight: Response). The calibration curve of HER2-ADC (I) was prepared per concentration of the competitive inhibition compound. The inhibition rate (%) was calculated by comparing the response at an HER2-ADC (I) concentration of 250 ng/mL to that of the case where no compound was added (concentration 0 ng/mL).

The graph showing the inhibition rate is shown in FIG. 41. Compound (1), compound (2), compound (7) and compound (9) exhibited strong competitive inhibition. In contrast, compound (8), compound (10), compound (11), Topotecan, and Rubitecan did not exhibit competitive inhibition. From the result, it was demonstrated that mouse antibody 1A3 specifically recognizes a chemical structure having the basic skeleton of the compound (1) and a methyl group at position 4.

[Sequence Listing Free Text]
SEQ ID NO: 1—CDRH1
SEQ ID NO: 2—CDRH2
SEQ ID NO: 3—CDRH3
SEQ ID NO: 4—CDRL1
SEQ ID NO: 5—CDRL2
SEQ ID NO: 6—CDRL3
SEQ ID NO: 7—CDRH1
SEQ ID NO: 8—CDRH2
SEQ ID NO: 9—CDRH1
SEQ ID NO: 10—CDRH2
SEQ ID NO: 11—CDRH1
SEQ ID NO: 12—CDRH2
SEQ ID NO: 13—CDRH3
SEQ ID NO: 14—CDRL1
SEQ ID NO: 15—Amino acid sequence of a heavy chain of mouse antibody 1A3
SEQ ID NO: 16—Amino acid sequence of a light chain of mouse antibody 1A3
SEQ ID NO: 17—Nucleotide sequence encoding the amino acid sequence of a heavy chain variable region of mouse antibody 1A3.
SEQ ID NO: 18—Nucleotide sequence encoding the amino acid sequence of a light chain variable region of mouse antibody 1A3
SEQ ID NO: 19—Amino acid sequence of a heavy chain of rabbit chimeric antibody 1A3
SEQ ID NO: 20—Amino acid sequence of a light chain of rabbit chimeric antibody 1A3
SEQ ID NO: 21—Amino acid sequence of a heavy chain of the anti-HER2 antibody
SEQ ID NO: 22—Amino acid sequence of a light chain of the anti-HER2 antibody
SEQ ID NO: 23—Amino acid sequence of a heavy chain of the anti-HER3 antibody
SEQ ID NO: 24—Amino acid sequence of a light chain of the anti-HER3 antibody
SEQ ID NO: 25—Amino acid sequence of a heavy chain of the anti-TROP2 antibody
SEQ ID NO: 26—Amino acid sequence of a light chain of the anti-TROP2 antibody
SEQ ID NO: 27—Amino acid sequence of a heavy chain of the anti-B7-H3 antibody
SEQ ID NO: 28—Amino acid sequence of a light chain of the Anti-B7-H3 antibody SEQ ID NO: 29—Nucleotide sequence encoding the amino acid sequences of a human light chain signal sequence and a human κ chain constant region.

SEQ ID NO: 30—Nucleotide sequence encoding the amino acid sequence of a heavy chain of rabbit chimeric antibody 1A3.

SEQ ID NO: 31—Nucleotide sequence encoding the amino acid sequence of a light chain of rabbit chimeric antibody 1A3.

SEQ ID NO: 32—Amino acid sequence of a heavy chain of the anti-GPR20 antibody

SEQ ID NO: 33—Amino acid sequence of a light chain of the anti-GPR20 antibody

SEQ ID NO: 34—Amino acid sequence of a heavy chain of the anti-CDH6 antibody

SEQ ID NO: 35—Amino acid sequence of a light chain of the anti-CDH6 antibody

The invention claimed is:
1. A protein that recognizes a drug moiety of an antibody-drug conjugate in which a drug represented by the following formula:

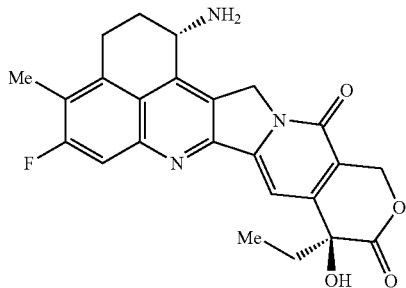 [SMILES: CC[C@@]1(O)C(=O)OCc2c1cc1n(c2=O)Cc2c-1nc1cc(F)c(C)c3c1c2[C@@H](N)CC3]

is conjugated to an antibody via a linker;
wherein the protein is:
a) an antibody comprising a heavy chain comprising CDRH1 consisting of an amino acid sequence represented by SEQ ID NO: 1, CDRH2 consisting of an amino acid sequence represented by SEQ ID NO: 2 and CDRH3 consisting of an amino acid sequence represented by SEQ ID NO: 3, and a light chain comprising CDRL1 consisting of an amino acid sequence represented by SEQ ID NO: 4, CDRL2 consisting of an amino acid sequence represented by SEQ ID NO: 5 and CDRL3 consisting of an amino acid sequence represented by SEQ ID NO: 6;
b) an antibody comprising a heavy chain comprising CDRH1 consisting of an amino acid sequence represented by SEQ ID NO: 7, CDRH2 consisting of an amino acid sequence represented by SEQ ID NO: 8 and CDRH3 consisting of an amino acid sequence represented by SEQ ID NO: 3, and a light chain comprising CDRL1 consisting of an amino acid sequence represented by SEQ ID NO: 4, CDRL2 consisting of an amino acid sequence represented by SEQ ID NO: 5 and CDRL3 consisting of an amino acid sequence represented by SEQ ID NO: 6;
c) an antibody comprising a heavy chain comprising CDRH1 consisting of an amino acid sequence represented by SEQ ID NO: 9, CDRH2 consisting of an amino acid sequence represented by SEQ ID NO: 10 and CDRH3 consisting of an amino acid sequence represented by SEQ ID NO: 3, and a light chain comprising CDRL1 consisting of an amino acid sequence represented by SEQ ID NO: 4, CDRL2 consisting of an amino acid sequence represented by SEQ ID NO: 5 and CDRL3 consisting of an amino acid sequence represented by SEQ ID NO: 6; or
d) an antibody comprising a heavy chain comprising CDRH1 consisting of an amino acid sequence represented by SEQ ID NO: 11, CDRH2 consisting of an amino acid sequence represented by SEQ ID NO: 12 and CDRH3 consisting of an amino acid sequence represented by SEQ ID NO: 13, and a light chain comprising CDRL1 consisting of an amino acid sequence represented by SEQ ID NO: 14, CDRL2 consisting of a tripeptide represented by WAS and CDRL3 consisting of an amino acid sequence represented by SEQ ID NO: 6.

2. The protein according to claim 1, wherein a drug-linker in the antibody-drug conjugate is represented by the following formula:

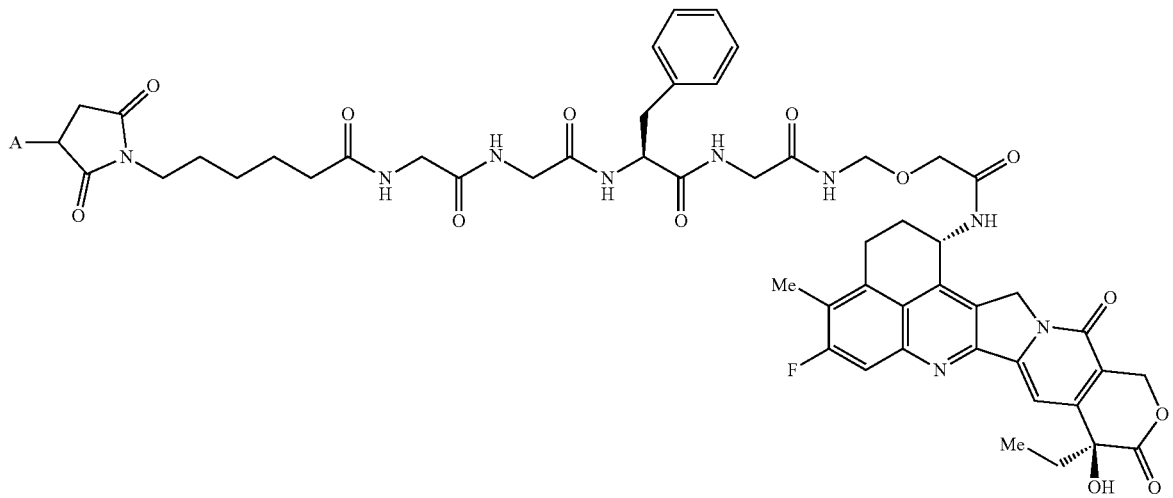

wherein A represents a connecting position to the antibody, and the drug-linker is conjugated to the antibody via a thioether bond.

3. The protein according to claim 1, wherein the drug-linker in the antibody-drug conjugate is represented by the following formula:

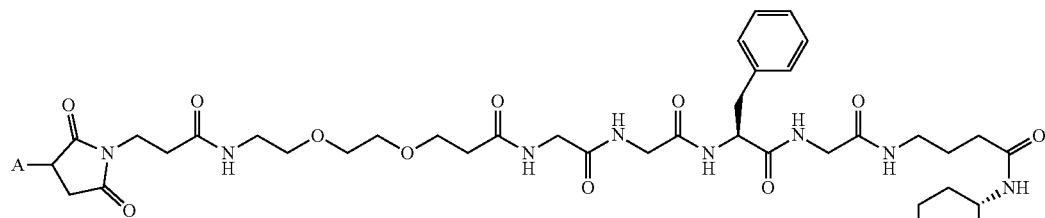

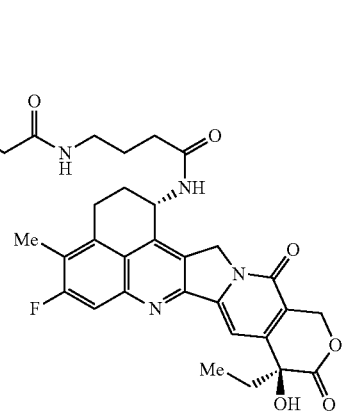

wherein A represents a connecting position to the antibody, and the drug-linker is conjugated to the antibody via a thioether bond.

4. The protein according to claim 1, wherein the drug-linker in the antibody-drug conjugate is represented by the following formula:

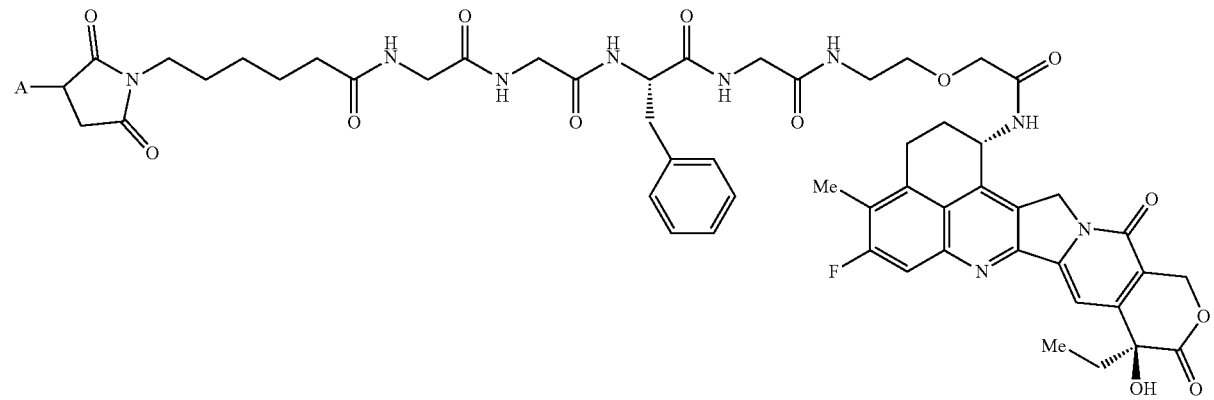

wherein A represents a connecting position to the antibody, and the drug-linker is conjugated to the antibody via a thioether bond.

5. The protein according to claim 1, wherein the antibody-drug conjugate is represented by the following formula:

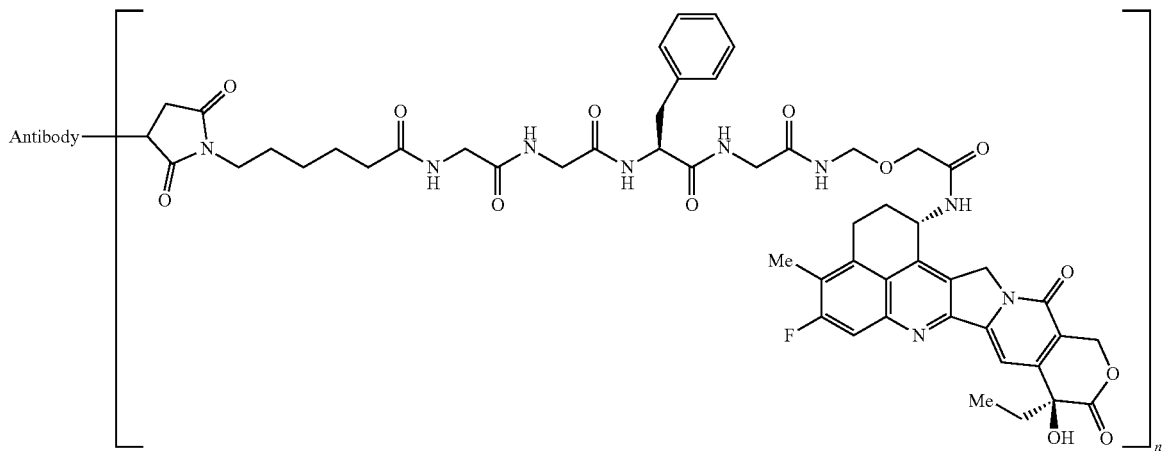

wherein the drug-linker is conjugated to the antibody via a thioether bond and n represents the average number of units of the drug-linker conjugated per antibody molecule.

6. The protein according to claim 1, wherein the antibody-drug conjugate is represented by the following formula:

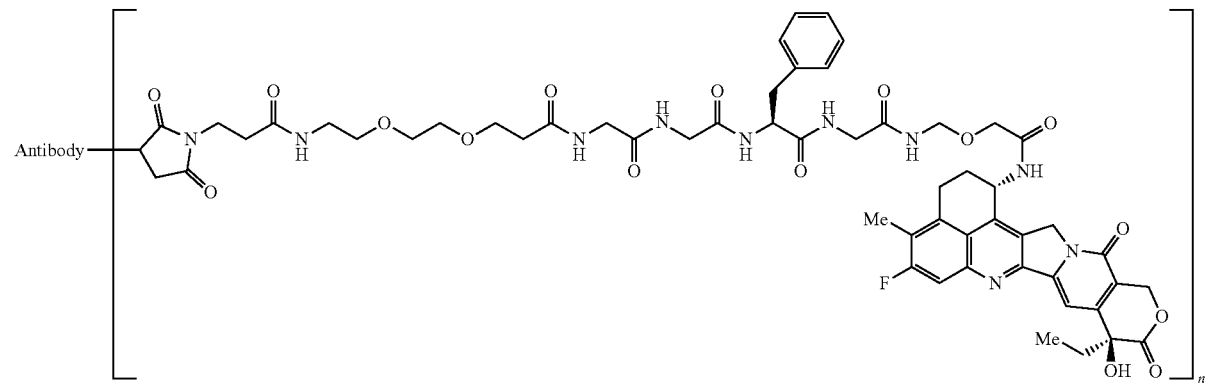

wherein the drug-linker is conjugated to the antibody via a thioether bond and n represents the average number of units of the drug-linker conjugated per antibody molecule.

7. The protein according to claim 1, wherein the antibody-drug conjugate is represented by the following formula:

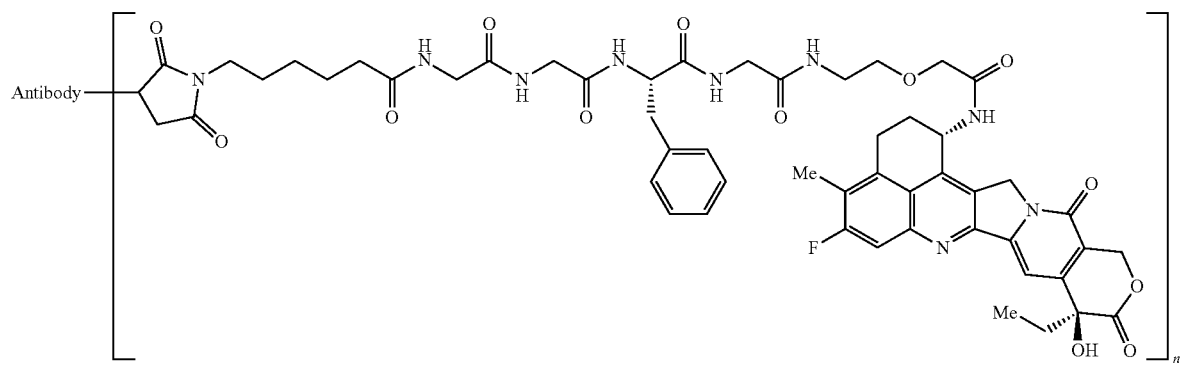

wherein the drug-linker is conjugated to the antibody via a thioether bond and n represents the average number of units of the drug-linker conjugated per antibody molecule.

8. The protein according to claim 1, wherein the average number of units of the drug-linker conjugated per antibody molecule in the antibody-drug conjugate is in the range of from 2 to 8.

9. The protein according to claim 1, wherein the antibody in the antibody-drug conjugate is an anti-HER2 antibody, an anti-HER3 antibody, an anti-TROP2 antibody, an anti-B7-H3 antibody, an anti-GPR20 antibody or anti-CDH6 antibody.

10. The protein according to claim 1, wherein the recognition property of the protein to the antibody-drug conjugate is independent of any difference in the average number of units of the drug-linker conjugated per antibody molecule in the antibody-drug conjugate.

11. The protein according to claim 1, wherein the protein is an antibody comprising a heavy chain comprising a heavy chain variable region consisting of an amino acid sequence consisting of amino acid residues 20 to 141 of SEQ ID NO: 15, and a light chain comprising a light chain variable region consisting of an amino acid sequence consisting of amino acid residues 21 to 127 of SEQ ID NO: 16.

12. The protein according to claim 11, wherein the protein is a mouse antibody.

13. The protein according to claim 11, wherein the protein is an antibody comprising a heavy chain comprising an amino acid sequence consisting of amino acid residues 20 to 477 of SEQ ID NO: 15, and a light chain comprising an amino acid sequence consisting of amino acid residues 21 to 234 of SEQ ID NO: 16.

14. The protein according to claim 11, wherein the protein is a chimeric antibody.

15. The protein according to claim 11, wherein the protein is a rabbit chimeric antibody.

16. The protein according to claim 11, wherein the protein is an antibody comprising a heavy chain comprising an amino acid sequence consisting of amino acid residues 20 to 464 of SEQ ID NO: 19, and a light chain comprising an amino acid sequence consisting of amino acid residues 21 to 233 of SEQ ID NO: 20.

17. A protein that recognizes a drug moiety of an antibody-drug conjugate in which a drug represented by the following formula:

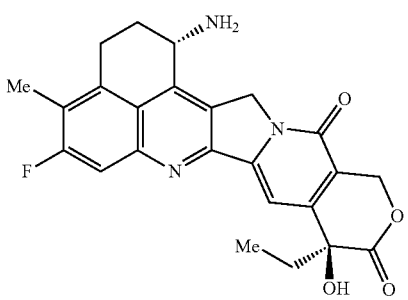 [SMILES: CC[C@@]1(O)C(=O)OCc2c1cc1n(c2=O)Cc2c-1nc1cc(F)c(C)c3c1c2[C@@H](N)CC3]

is conjugated to an antibody via a linker, wherein the protein is an antibody in which a lysine residue at the carboxyl terminus of the heavy chain of the antibody is deleted, and wherein the antibody comprises:
a heavy chain comprising an amino acid sequence consisting of amino acid residues 20 to 477 of SEQ ID NO: 15, and a light chain comprising an amino acid sequence consisting of amino acid residues 21 to 234 of SEQ ID NO: 16, or a heavy chain comprising an amino acid sequence consisting of amino acid residues 20 to 464 of SEQ ID NO: 19, and a light chain comprising an amino acid sequence consisting of amino acid residues 21 to 233 of SEQ ID NO: 20.

18. A protein that recognizes a drug moiety of an antibody-drug conjugate in which a drug represented by the following formula:

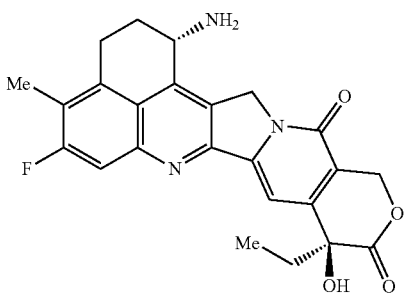 [SMILES: CC[C@@]1(O)C(=O)OCc2c1cc1n(c2=O)Cc2c-1nc1cc(F)c(C)c3c1c2[C@@H](N)CC3]

is conjugated to an antibody via a linker, wherein the protein is an antigen binding fragment of
a) an antibody comprising a heavy chain comprising CDRH1 consisting of an amino acid sequence represented by SEQ ID NO: 1, CDRH2 consisting of an amino acid sequence represented by SEQ ID NO: 2 and CDRH3 consisting of an amino acid sequence represented by SEQ ID NO: 3, and a light chain comprising CDRL1 consisting of an amino acid sequence represented by SEQ ID NO: 4, CDRL2 consisting of an amino acid sequence represented by SEQ ID NO: 5 and CDRL3 consisting of an amino acid sequence represented by SEQ ID NO: 6;
b) an antibody comprising a heavy chain comprising CDRH1 consisting of an amino acid sequence represented by SEQ ID NO: 7, CDRH2 consisting of an amino acid sequence represented by SEQ ID NO: 8 and CDRH3 consisting of an amino acid sequence represented by SEQ ID NO: 3, and a light chain comprising CDRL1 consisting of an amino acid sequence represented by SEQ ID NO: 4, CDRL2 consisting of an amino acid sequence represented by SEQ ID NO: 5 and CDRL3 consisting of an amino acid sequence represented by SEQ ID NO: 6;
c) an antibody comprising a heavy chain comprising CDRH1 consisting of an amino acid sequence represented by SEQ ID NO: 9, CDRH2 consisting of an amino acid sequence represented by SEQ ID NO: 10 and CDRH3 consisting of an amino acid sequence represented by SEQ ID NO: 3, and a light chain comprising CDRL1 consisting of an amino acid sequence represented by SEQ ID NO: 4, CDRL2 consisting of an amino acid sequence represented by SEQ ID NO: 5 and CDRL3 consisting of an amino acid sequence represented by SEQ ID NO: 6; or
d) an antibody comprising a heavy chain comprising CDRH1 consisting of an amino acid sequence represented by SEQ ID NO: 11, CDRH2 consisting of an amino acid sequence represented by SEQ ID NO: 12 and CDRH3 consisting of an amino acid sequence represented by SEQ ID NO: 13, and a light chain comprising CDRL1 consisting of an amino acid sequence represented by SEQ ID NO: 14, CDRL2 consisting of a tripeptide represented by WAS and CDRL3 consisting of an amino acid sequence represented by SEQ ID NO: 6.

19. The protein according to claim 18, wherein the antigen-binding fragment of the antibody is Fab, F(ab')2, Fab' or Fv.

20. A composition comprising the protein according to claim 1.

21. A kit comprising the protein according to claim 1 or a composition comprising the protein according to claim 1.

22. The kit according to claim 21 for quantifying the concentration in plasma of an antibody-drug conjugate and/or a drug released from the antibody-drug conjugate in a mammal to which the antibody-drug conjugate has been administered.

23. The kit according to claim 21 for identifying the tissue distribution of an antibody-drug conjugate and/or a drug released from the antibody-drug conjugate in a mammal to which the antibody-drug conjugate has been administered.

* * * * *